United States Patent
Wang et al.

(10) Patent No.: US 9,096,856 B2
(45) Date of Patent: Aug. 4, 2015

(54) NUCLEOTIDES AND APTAMERS CONTAINING BORONIC ACID GROUPS HAVING BIASED BINDING TO GLYCOSYLATED PROTEINS, AND USES THEREOF

(75) Inventors: Binghe Wang, Marietta, GA (US); Minyong Li, Shandong (CN); Zhen Huang, Marietta, GA (US); Na Lin, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 1319 days.

(21) Appl. No.: 12/669,593

(22) PCT Filed: Jul. 17, 2008

(86) PCT No.: PCT/US2008/070288
§ 371 (c)(1),
(2), (4) Date: May 11, 2010

(87) PCT Pub. No.: WO2009/012363
PCT Pub. Date: Jan. 22, 2009

(65) Prior Publication Data
US 2013/0184160 A1    Jul. 18, 2013

Related U.S. Application Data

(60) Provisional application No. 60/950,681, filed on Jul. 19, 2007.

(51) Int. Cl.
*C12Q 1/68* (2006.01)
*C12N 15/115* (2010.01)
(Continued)

(52) U.S. Cl.
CPC .............. *C12N 15/115* (2013.01); *C07H 19/04* (2013.01); *C07H 21/00* (2013.01); *C07H 23/00* (2013.01);
(Continued)

(58) Field of Classification Search
None
See application file for complete search history.

(56) References Cited

U.S. PATENT DOCUMENTS 4,269,605 A     5/1981  Dean et al.
5,047,519 A *   9/1991  Hobbs et al. ............... 536/27.14
(Continued)

FOREIGN PATENT DOCUMENTS

WO      9805672 A1      2/1998

OTHER PUBLICATIONS

Lin et al., "Design and synthesis of boronic-acid-labeled thymidine triphosphate for incorporation into DNA," Nucl. Acids Res. 2007, 35:1222-1229, published online Jan. 2, 2007.*
(Continued)

*Primary Examiner* — Samuel Woolwine
*Assistant Examiner* — Kaijiang Zhang
(74) *Attorney, Agent, or Firm* — Thomas|Horstemeyer, LLP

(57) ABSTRACT

The present disclosure encompasses oligonucleotide aptamers selectively binding a target glycosylated polypeptide or protein, and having biased affinity for the glycan through a boronic acid linked to a nucleosidic base of a nucleotide(s). The disclosure further encompasses methods for isolating an aptamer(s) selectively binding a target glycosylated polypeptide, where, from a population of randomized oligonucleotides that have at least one nucleotide having a boronic acid label linked to a base, is selected a first subpopulation of aptamers binding to the target glycosylated polypeptide or protein. This subpopulation is then amplified without using boronic acid-modified TTP, and amplification products not binding to a target glycosylated polypeptide or protein are selected. The second subpopulation of aptamers is then amplified using boronic acid-modified TTP to provide a population of boronic acid-modified aptamers capable of selectively binding to a glycosylation site of a target polypeptide or protein. Other aspects of the disclosure encompass methods for the use of the modified aptamers to detect glycosylated species of a polypeptide or protein.

29 Claims, 27 Drawing Sheets

(51) Int. Cl.
    *C07H 19/00*     (2006.01)
    *C07H 23/00*     (2006.01)
    *C40B 10/00*     (2006.01)
    *G01N 33/68*     (2006.01)
    *C07H 19/04*     (2006.01)
    *C07H 21/00*     (2006.01)
    *C12N 15/10*     (2006.01)
    *G01N 33/86*     (2006.01)

(52) U.S. Cl.
    CPC ............ *C12N 15/1048* (2013.01); *G01N 33/68* (2013.01); *G01N 33/6893* (2013.01); *G01N 33/86* (2013.01); *C12N 2310/16* (2013.01); *C12N 2310/33* (2013.01)

(56) References Cited

U.S. PATENT DOCUMENTS 5,270,163 A     12/1993     Gold et al.
5,831,046 A *   11/1998     Stolowitz et al. ............ 536/22.1

OTHER PUBLICATIONS

Wang et al., "Fluorescent Indolylboronic Acids that are Useful Reporters for the Synthesis of Boronolectins," Chem. Biol. Drug Des. 2006, 67:137-144.*

Schwarz et al., Fluorescence Measurements of Benzene, Naphthalene, Anthracene, Pyrene, Fluoranthene, and Benzo[e]pyrene in Water, Anal. Chem. 1976, 48:524-528.*

The Supplementary European Search Report dated Jun. 7, 2013.

Lin, et al., "Design and Synthesis of Boronic-Acid-Labeled Thymidine Triphosphate for Incorporation into DNA", Nucleic Acids Research, Oxford University Press, Surrey, GB, vol. 35, No. 4, Feb. 1, 2007, pp. 1222-1229.

Minyong Li, et al.,"Selecting Aptamers for a Glycoprotein Through the Incorporation of the Boronic Acid Moiety," Journal of the American Chemical Society, vol. 130, No. 38, Sep. 24, 2008, pp. 12636-12638.

* cited by examiner

SEQ ID NO.: 1; Primer 21nt
GCGTAATACGACTCACTATAG

SEQ ID NO.: 2; Primer 1
GCGTAATACGACTCACTATA

SEQ ID NO.: 3; Primer 2
TGTACGTTTCGGCCTTTCGG

SEQ ID NO: 4; Template 1 DNA:
TGTACGTTTCGGCCTTTCGGCCTCATCAGGTTGCCTATAGTGAGTCGTATTACGC SEQ ID NO.: 5; Primer 3
CGCCGCCCCCGCCGCG SEQ ID NO.: 6; Primer 4
CGGCGGCCCGCGGGCG SEQ ID NO.: 7; Template 2 DNA
CGCCGCCCCCGCCGCGNNNNNNNNNNNNNNNNNNNNNNNNNNNNNNNNNNNNNCGCCCG
CGGGCCGCCG SEQ ID NO.: 8; Template 21-nt
GGTTCCACCAGCAACCCGCTA SEQ ID NO.: 9; Primer 14-nt
TAGCGGGTTGCTGG SEQ ID NO.: 10; Template 5
CCTTCGTTGTCTGCCTTCGTNNNNNNNNNNNNNNNNNNNNNNNNNNNNNNNNNNNNNNN
NNNNNNNNNACCCTTCAGAATTCGCACCA SEQ ID NO.: 11; Primer 20.227
CCTTCGTTGTCTGCCTTCGT SEQ ID NO.: 12; Primer 20.226
TGGTGCGAATTCTGAAGGGT SEQ ID NO.: 13; aptamer 85 (114H)
CCTTCGTTGTCTGCCTTCGTAGCGGATCGAATTACGCGTTAACGGCAACCGATAACGGGACC
GATTGCACACCCTTCAGAATTCGCACCA SEQ ID NO.: 14; aptamer 85B n(114O)
CCTTCGTTGTCTGCCTTCGTAGGACCGCAGACATCGACGCAGGGAAATTCCGCAAGTCCAGC
CAAATGCCACCCTTCAGAATTCGCACCA SEQ ID NO.: 15; aptamer 85C (114F)
CCTTCGTTGTCTGCCTTCGTAGTCGACTCTGACGCATGGACGTATCCTGTGCGTATGCATTA
TGAAGCACACCCTTCAGAATTCGCACCA SEQ ID NO.: 16; aptamer 85E (114N)
CCTTCGTTGTCTGCCTTCGTGAGCGGAGTCAGACGCACGCTCGTACCTGTGCGCAAGCACTA
TGACGGACACCCTTCAGAATTCGCACCA

*Fig. 26A*

SEQ ID NO.: 17; aptamer 85F
CCTTCGTTGTCTGCCTTCGTAGCCTTAAGCTCCCTATGATTGGCCGGATCGTAAGTACGTTG
GGATCGAGACCCTTCAGAATTCGCACCA SEQ ID NO.: 18; aptamer 85G
CCTTCGTTGTCTGCCTTCGTACCGGTTCCGATATGAAGCAAAGTCCACAGGCCAATAAGCAG
GAGCGCAGACCCTTCAGAATTCGCACCA SEQ ID NO.: 19; aptamer 85H
CCTTCGTTGTCTGCCTTCGTACCATGGCTGTCAACGGCCGTCCGGTACCGGGCTTGACGAGT
ATCCGGACACCCTTCAGAATTCGCACCA SEQ ID NO.: 20; aptamer 85J
CCTTCGTTGTCTGCCTTCGTATAGGTCTGTGCTGCGCTATCGTGCGCACCTCTTCAGATATG
TCGCACGCACCCTTCAGAATTCGCACCA SEQ ID NO.: 21; aptamer 85K
CCTTCGTTGTCTGCCTTCGTACGGCCGGCTGGTAGCCACGCCGGGCTTGCTTGAGGTCAGCC
TATGGCGCACCCTTCAGAATTCGCACCA SEQ ID NO.: 22; aptamer 85M (114B)
CCTTCGTTGTCTGCCTTCGTGCGCGCATAGACCGAGTGGCATGACGCCTATCTCGTGATAGA
GGACTCCGACCCTTCAGAATTCGCACCA SEQ ID NO.: 23; aptamer 85N
CCTTCGTTGTCTGCCTTCGTATATCTGGACAAGGGAATTCGCAAGCGCGAAGTGAACGCAGG
TAGCTCGCACCCTTCAGAATTCGCACCA SEQ ID NO.: 24; aptamer 85
CCTTCGTTGTCTGCCTTCGTAGCAGTATGGTCCGAAAGATCGGCGCTAAGGCTCGTACTAGG
CGTATGCCACCCTTCAGAATTCGCACCA SEQ ID NO.: 25; aptamer 85P (114M)
CCTTCGTTGTCTGCCTTCGTCCGTGTCCCGCTATGATGCTACTTGCATTCGCGGAATTGAAC
CGTCGCGCACCCTTCAGAATTCGCACCA SEQ ID NO.: 26; aptamer 85Q (114G)
CCTTCGTTGTCTGCCTTCGTAGCCCTTGCACCTATGAGGTATGATCTTCGTTGGACGCAGTT
ACTACGCCACCCTTCAGAATTCGCACCA SEQ ID NO.: 27; aptamer 85R
CCTTCGTTGTCTGCCTTCGTTGGACAACGTCGGACTCGATAGCGTAGACGGAAGCCTGGTCT
GGTCGCGCACCCTTCAGAATTCGCACCA SEQ ID NO.: 28; aptamer 85T (114Q)
CCTTCGTTGTCTGCCTTCGTCAGCTACTGGGCTATCTGGACTTGGCAATCTCGCTTGCAGCA
TTGAGCGCACCCTTCAGAATTCGCACCA SEQ ID NO.: 29; aptamer 76A
CCTTCGTTGTCTGCCTTCGTAGTCGACTCTGACGCATGGACGTATCCTGTGCGTATGCATTA
TGAAGCACACCCTTCAGAATTCGCACCA

*Fig. 26B*

SEQ ID NO.: 30; aptamer 76B
CCTTCGTTGTCTGCCTTCGTAGCGGATCGAATTACGCGTTAACGGCAACCGATAACGGGACC
GATTGCACACCCTTCAGAATTCGCACCA SEQ ID NO.: 31; aptamer 76C (114R)
CCTTCGTTGTCTGCCTTCGTACGAACGCTGACATCGACGGTCGGCAATTCCGCAAGTCCAGC
CTAATGACACCCTTCAGAATTCGCACCA SEQ ID NO.: 32; aptamer 76D (114T)
CCTTCGTTGTCTGCCTTCGTAGCGCTAGGACGTAAGATGCATGCCCTAGATTCGAAGCTGAT
GCCATGAGACCCTTCAGAATTCGCACCA SEQ ID NO.: 33; aptamer 76E
CCTTCGTTGTCTGCCTTCGTACGGCTAACGGAATCAAGCTTAGAGGATAAGCCGATAAGCAC
GATAGCACACCCTTCAGAATTCGCACCA SEQ ID NO.: 34; aptamer 76F
CCTTCGTTGTCTGCCTTCGTTGCAATAAGGTCGGATTGATTGGCCCGAACGTTAGAACCCGG
GGAACGACACCCTTCAGAATTCGCACCA SEQ ID NO.: 35; aptamer 76H
CCTTCGTTGTCTGCCTTCGTAGCGCTAAGAGGGTGCGGATTGAGGCGGATCGCGGGCTTGAC
CGATTGCCACCCTTCAGAATTCGCACCA SEQ ID NO.: 36; aptamer 76I
CCTTCGTTGTCTGCCTTCGTAGCGGCGGGAGGGAGTTAGGCGAGGCGAGCCCGAGCTTAGGC
TTAGGCCGACCCTTCAGAATTCGCACCA SEQ ID NO.: 37; aptamer 87ª (114I)
CCTTCGTTGTCTGCCTTCGTAGGACCGCAGACATCGACGCAGGGAAATTCCGCAAGTCCAGC
CAAATGCCACCCTTCAGAATTCGCACCA SEQ ID NO.: 38; aptamer 87B
CCTTCGTTGTCTGCCTTCGTAGCCTGCTCTGGCGCATGTACGCATCGCGTTCGTATGCAATA
TGACGCATACCCTTCAGAATTCGCACCA SEQ ID NO.: 39; aptamer 87C
CCTTCGTTGTCTGCCTTCGTACAGGGTAGCGCTACGCTAGACTAGGTACGTATCCTGATATG
ACGCTCGCACCCTTCAGAATTCGCACCA SEQ ID NO.: 40; aptamer 87D
CCTTCGTTGTCTGCCTTCGTACGGCGGCTGGAGCAACGCCTGGCATGGGTGCGGTCAGAAGT
ATTGCGCAACCCTTCAGAATTCGCACCA SEQ ID NO.: 41; aptamer 87F
CCTTCGTTGTCTGCCTTCGTAACCGGCGTGAGCGAGTCAGTCGAGGCGAGCTACGAGCTTAG
CTCAGGTCACCCTTCAGAATTCGCACCA SEQ ID NO.: 42; aptamer 87G
CCTTCGTTGTCTGCCTTCGTAACGTCTAACGGTATCAAGCTTAGAGGATACGCTGATCACTA
CCATAGTAACCCTTCAGAATTCGCACCA

*Fig. 26C*

SEQ ID NO.: 43; aptamer 87H
CCTTCGTTGTCTGCCTTCGTAACGGCGGGCTTGATAGTCTCGCAGGCCATACTCGAGCTCTC
GTATGACGACCCTTCAGAATTCGCACCA SEQ ID NO.: 44; aptamer 87I
CCTTCGTTGTCTGCCTTCGTAGTGCTACGACTATGACGCATATCGCTCGATTCGTGGCAGGT
TCTCATACACCCTTCAGAATTCGCACCA SEQ ID NO.: 45; aptamer 87J (114ᵃ)
CCTTCGTTGTCTGCCTTCGTACGCGCGCATAGTCCGAGTAGTATGACGCATATGTGCTACTG
AGTCCTACACCCTTCAGAATTCGCACCA SEQ ID NO.: 46; aptamer 87L
CCTTCGTTGTCTGCCTTCGTACAGATAGCGAGAGCTACGATGCTGCGAATAGAGCGTACGGC
GGGCTTGAACCCTTCAGAATTCGCACCA SEQ ID NO.: 47; aptamer 87M
CCTTCGTTGTCTGCCTTCGTACAGCAGTATCGTGCGAAAGATCGTCGCTATGAGTCCTACAG
TCTTACGCACCCTTCAGAATTCGCACCA SEQ ID NO.: 48; aptamer 87N
CCTTCGTTGTCTGCCTTCGTAGCCGTTGCACGGTATGAGGCATAGACCTACGTATGAGGCTA
ACTTCGGCACCCTTCAGAATTCGCACCA SEQ ID NO.: 49; aptamer 87° (114D)
CCTTCGTTGTCTGCCTTCGTGCTATGTCTGAGCAGTGCGTATGGTACCTCGTATCAGCCATA
TGACGCAAACCCTTCAGAATTCGCACCA SEQ ID NO.: 50; aptamer 87P
CCTTCGTTGTCTGCCTTCGTACAGCTCTATGAGTACGCATCGAGATCAGAACCGCGGGCTTG
AACGTCAGACCCTTCAGAATTCGCACCA SEQ ID NO.: 51; aptamer 87Q (114L)
CCTTCGTTGTCTGCCTTCGTTATGACGCAACTGTGCACAATGCGACTCAGGACGTGTACGAG
CGAGTGTAACCCTTCAGAATTCGCACCA SEQ ID NO.: 52; aptamer 87T (114K)
CCTTCGTTGTCTGCCTTCGTCGTGACCAGGACATATGAGGCATAGCGCTTGACTCTACCGCT
GCTAGCACACCCTTCAGAATTCGCACCA SEQ ID NO.: 53; aptamer 114C
CCTTCGTTGTCTGCCTTCGTTAGACTATCACGGATGGACGTATCCTGTGCGTATGACGCATG
AAGCACTAACCCTTCAGAATTCGCACCA SEQ ID NO.: 54; aptamer 114E
CCTTCGTTGTCTGCCTTCGTATATGACGCATGCCTAGACCTCCCTATGATAGCCTGGATCGT
ACGTACGTACCCTTCAGAATTCGCACCA SEQ ID NO.: 55; aptamer 114I(7A)
CCTTCGTTGTCTGCCTTCGTAGGACCGCAGACATCGACGCAGGGAAATTCCGCAAGTCCAGC
CAAATGCCACCCTTCAGAATTCGCACCA

*Fig. 26D*

SEQ ID NO.: 56; aptamer 114J
CCTTCGTTGTCTGCCTTCGTGAGCAGCGTAGCTCTAAGCCAGACTAGTAACGTATCCTGATA
TGACGCATACCCTTCAGAATTCGCACCA SEQ ID NO.: 57; aptamer 114P
CCTTCGTTGTCTGCCTTCGTTCAGGCTGCTATATGACGCATATCGACAGACGAGTCAGTAGC
TGCACACAACCCTTCAGAATTCGCACCA SEQ ID NO.: 58; aptamer 114S
CCTTCGTTGTCTGCCTTCGGCATCACTACGGTCGAGATACATAGTCGCTATGACGCATCAGT
CTTACGCTACCCTTCAGAATTCGCACCA SEQ ID NO.: 59; aptamer 5A
CCTTCGTTGTCTGCCTTCGTTATCGGTTTGCCATCGACGGTCGGCACTTCCGCTACCATCTG
GCCTAATGACCCTTCAGAATTCGCACCA SEQ ID NO.: 60; aptamer 5B
CCTTCGTTGTCTGCCTTCGTCTAGGCATATCGGTTTGCCATCGTCGAGCACTTCCGCTACGT
AAGATTCCACCCTTCAGAATTCGCACCA SEQ ID NO.: 61; aptamer 5C
CCTTCGTTGTCTGCCTTCGTTTCTACGGTAACCTTATCGGTTTGCCATCGACGGCCGTAATT
CGGCATCGACCCTTCAGAATTCGCACCA SEQ ID NO.: 62; aptamer 5D
CCTTCGTTGTCTGCCTTCGTACTCTAGCCTACGTAATCACGATTACGGATATCGGTTTGCCA
TCGTCATGACCCTTCAGAATTCGCACCA SEQ ID NO.: 63; aptamer 5E
CCTTCGTTGTCTGCCTTCGTATATTCGGCGTAGCCATTAGCTTAGCGATTAGCCTATCGGTT
TGCCATCGACCCTTCAGAATTCGCACCA SEQ ID NO.: 64; aptamer 5F
CCTTCGTTGTCTGCCTTCGTTCCGTGGCCGATTACGGGTCTATCGGTTTGCCATCGTACGAT
GCGGATCAACCCTTCAGAATTCGCACCA SEQ ID NO.: 65; aptamer 5G
CCTTCGTTGTCTGCCTTCGTCGGCATGATCGTACGCTATCGGTTTGCCATCGTACCGCTAGT
TCGGTAGCACCCTTCAGAATTCGCACCA SEQ ID NO.: 66; aptamer 5H
CCTTCGTTGTCTGCCTTCGTTAACCTGGCGATGCGACCGTGATGCCGTATCGGTTTGCCATC
GATACGCCACCCTTCAGAATTCGCACCA SEQ ID NO.: 67; aptamer 5I
CCTTCGTTGTCTGCCTTCGTTAAACTTCTAAACCTGCCGGATACTCTATATCGGTTTGCCAT
CGATTAACACCCTTCAGAATTCGCACCA SEQ ID NO.: 68; aptamer 5J
CCTTCGTTGTCTGCCTTCGTTATCGATTAGCGGACGATTAGGCCATGAGCGATATCGGTTTG
CCATCGCGACCCTTCAGAATTCGCACCA SEQ ID NO.: 69; PSA Aptamer Core
TATCGGTTTGCCATCG

*Fig. 26E*

NUCLEOTIDES AND APTAMERS CONTAINING BORONIC ACID GROUPS HAVING BIASED BINDING TO GLYCOSYLATED PROTEINS, AND USES THEREOF

CROSS-REFERENCE TO RELATED APPLICATION

This application claims priority to the PCT application entitled "NUCLEOTIDES AND APTAMERS CONTAINING BORONIC ACID GROUPS HAVING BIASED BINDING TO GLYCOSYLATED PROTEINS, AND USES THEREOF," having serial number PCT/US2008/070288, filed on Jul. 17, 2008. This application also claims priority to and benefit of U.S. Provisional Patent Application No. 60/950,681, filed on Jul. 19, 2007, which is incorporated by reference in its entirety.

STATEMENT REGARDING FEDERALLY SPONSORED RESEARCH OR DEVELOPMENT

This invention was made with government support under Grant Nos.: CA123329, CA113917, DK55062, CA88343, and NO1-CO-27184 awarded by the National Institutes of Health of the United States Government. The government has certain rights in the invention.

FIELD OF THE DISCLOSURE

The present disclosure relates to nucleotides, aptamers incorporating boronic acids, the manufacture of nucleotides and aptamers incorporating boronic acids, where the aptamers have enhanced affinity and specificity for glycosylated proteins. The disclosure further relates to methods of selectively detecting glycosylated species of proteins using aptamers incorporating boronic acids.

BACKGROUND

Post-/co-translational modifications including phosphorylation, methylation, acylation, ubiquitination, SUMOlyation, and glycosylation play critical roles in determining the functions and fates of proteins (Walsh, C., ed. *Posttranslational Modification of Proteins: Expanding Nature's Inventory.* 2006, Roberts & Co: Englewood, Colo.). Among these modifications, glycosylation results in significant structural diversity and complexity of protein products. Usually, for the purpose of correlating glycosylation states with pathological changes, it is not a question of whether there is glycosylation, but rather the glycosylation pattern that marks protein function or different pathological states, including malignancy. For example, the glycosylation patterns of prostate specific antigen (PSA) from cancer cells in culture (Peracaula et al., *Glycobiol.,* 2003. 13: 457-470) and prostate cancer patient's tissue and serum (Tabares et al., *Glycobiology,* 2006. 16(2): 132-145; Tabares et al., *Clin. Biochem.,* 2007, 40: 343-350) are different from that of the normal prostate. Human pancreatic RNase 1, a glycoprotein secreted mostly by pancreatic cells, has completely different oligosaccharide chains when produced from pancreatic tumor cells, and deviation from the normal glycosylation pattern on fibrinogen, a protein critical to blood coagulation, can lead to coagulation disorders (Cohn et al., *Pediatrics,* 2006. 118: 514-521; Langer et al., *J. Biol. Chem.,* 1988. 263: 15056-15063; Gilman et al., *J. Biol. Chem.,* 1984. 259: 3248-3253; Hamano et al., *Blood,* 2004. 103: 3045-3050; Mirshahi et al., *Thromb. Res.,* 1987. 48: 279-289; Ridgway et al., *Br. J. Haematol.,* 1997. 99: 562-569; Rybarczyk et al., *Cancer Res.,* 2000. 60: 2033-2039; Sugo et al., *Blood,* 1999. 94: 3806-3813). Pregnancy-related human chorionic gonadotropin (hCG) can provide biomarkers for cancer, Down syndrome, and pregnancy failure depending on its glycosylation patterns (Wang et al., *Curr. Org. Chem.,* 2002. 6: 1285-1317; Gao et al., *Org. Lett.,* 2003. 5: 4615-4618); and specific glycosylation patterns of haptoglobin (Hp) and alpha-fetoprotein (AFP) have a much higher degree of correlation with cancer than the total Hp/AFP levels (Yang et al., *Chem. Biol.,* 2004. 11: 439-448).

Since certain glycoforms of these proteins are directly disease related, the ability to analyze and differentiate variations of glycosylation patterns in a given glycoprotein would be of value for the development of new diagnostics and biomedical research tools. Currently available analytical tools used for glycomics analysis include such as mass spectrometry, chromatography, especially capillary electrophoresis, antibody-based approaches, lectin profiling, and the like. However, there remains a need for techniques suitable for the rapid and accurate detection of protein glycosylation variations. Mass spectrometry and chromatography methods are time-consuming. Lectin profiling is useful for broad category glycan characterizations, but it only focuses on the glycan portion and does not give any indication as to the identity of the protein in question. As a result, purified or partially purified glycoproteins are usually needed for lectin-based characterizations in detail. Furthermore, cross-reactivity and low affinity are issues that may impede the application of lectins for highly specific characterizations. In addition, there are only about forty readily available lectins, which cannot satisfy the need for highly specific recognitions of various glycosylation patterns.

Molecules that can recognize a target glycoprotein with high affinity and specificity should preferably recognize both the glycan and the protein portions to be useful for glycoform-specific detection. However, antibodies and aptamer selection for the development of molecules of high specificity and affinity for glycoproteins do not have the intrinsic ability to specifically focus on the glycosylation sites in its native form, and allow for the ready differentiation of glycosylation variations.

Aptamer selection is a very powerful method for the development of custom-made nucleic acid-based high affinity "binders" (aptamers) for molecules of interest. Since the beginning of this field, a large number of aptamers have been reported for various applications with some in clinical trials or approved for clinical use. As powerful as the method is, aptamer selection has limited intrinsic ability to selectively focus on certain substructures of a large biomacromolecule. Therefore, methods for selection of aptamers that can recognize a glycoprotein and be able to differentiate its glycosylation patterns will be advantageous for the development of novel types of diagnostics and therapeutics as well as analytical tools for biomedical research.

SUMMARY

The boronic acid moiety is a versatile functional group useful in carbohydrate recognition, glycoprotein pull-down, inhibition of hydrolytic enzymes, and boron neutron capture therapy. The incorporation of the boronic acid group into DNA as disclosed herein leads to molecules of various biological functions. In an embodiment, boronic acid-label has been linked through a 14-atom tether to thymidine triphosphate (B-TTP) and the modified nucleotide was effectively incorporated into DNA by enzymatic polymerization. In an embodiment, the synthesis of B-TTP was achieved using the Huisgen cycloaddition, although other conjugation methods are possible. DNA polymerase effectively recognizes the boronic acid-labeled DNA as the template for DNA polymerization, which allows PCR amplification of boronic acid-labeled DNA.

The incorporation of the boronic acid moiety into nucleic acid provides new aptamers directed against carbohydrates, glycoproteins, and glycolipids with specific focus on differentiating the carbohydrate portion. Boronic acid-aptamers with high specificity and affinity for certain carbohydrates and adjacent structures are suitable as tools for the rapid analysis of glycosylation patterns of proteins, peptides, and lipids.

One aspect of the present disclosure, therefore, encompasses modified mono-, di-, or triphosphorylated nucleotide monomers having a ribose or deoxyribose sugar moiety, and a nucleosidic base, where the base is modified by being linked, optionally through a tether, with a boronic acid. It is contemplated that the boronic acid group may also be a fluorescent boronic acid that may also function as a label that allows detection of a modified nucleotide, or an oligonucleotide aptamer into which it has been incorporated.

Another aspect of the disclosure provides oligonucleotide aptamers comprising at least one modified nucleotide monomer having a ribose or deoxyribose sugar moiety, and a nucleosidic base (base) selected from adenine, cytosine, guanine, thymine, hypoxanthine, uracil, and the like, where the base is modified by being linked, optionally through a tether, with a boronic acid. The aptamers of the present disclosure are selected to have selective affinity for a target polypeptide or protein, and a glycosylation chain thereon. The aptamers of the present disclosure, therefore, selectively bind glycosylation sites of target polypeptides, where the glycosylation sites typically comprise a region of the polypeptide and a region of an attached glycan.

Yet another aspect of the disclosure encompasses methods for isolating an aptamer having selective affinity for a target polypeptide and a glycan thereon, comprising: from a population of randomized oligonucleotides, where each oligonucleotide includes at least one nucleotide having a boronic acid label linked to a base thereon, selecting a first subpopulation of aptamers binding to a target glycosylated polypeptide or protein; amplifying the first subpopulation of aptamers without using boronic acid-modified TTP, and selecting from the amplification products thereof a second subpopulation of aptamers not binding to a glycosylated species of the target polypeptide or protein; amplifying the second subpopulation of aptamers using boronic acid-modified TTP, and thus providing a population of boronic acid-modified aptamers capable of selectively binding to a glycosylation site of a target polypeptide or protein. The counter-selection step of the aptamer selection methods of the disclosure, by eliminating the boronic-acid modification to the thymidine bases that otherwise drives the binding of aptamers to the glycan, selects out those aptamers that can bind to the target polypeptide or protein, but not to the glycan. Additional counter-selection steps may also be used, such as selecting against blank beads, deglycosylated protein, or cross-reacting non-targeted (glyco)proteins.

The aptamer selection methods may further comprise inserting a population of aptamers into a vector and isolating clones thereof; identifying a plurality of aptamer clones, where the aptamers have sequences differing from each other; determining the dissociation constants of the individual aptamers and the target glycosylated polypeptide or protein; comparing the dissociation constants of the aptamers to the dissociation constants of a control aptamer not having a boronic acid thereon; and selecting one or more aptamers having a lower dissociation constant than the control. The selected aptamers can have enhanced selective affinity for a glycosylated site of the target glycosylated polypeptide compared to control aptamers having identical nucleotide sequences to those of the selected aptamers, but not having a boronic acid group thereon.

Another aspect of the disclosure provides methods of selectively detecting the glycosylation status of a target polypeptide, comprising: providing a subject target polypeptide or protein; contacting the target polypeptide with an aptamer population capable of selectively binding a glycosylation site of the target polypeptide or protein under conditions whereupon, if the glycosylation site is present on the target polypeptide the aptamer will bind thereto; isolating the bound aptamers from unbound aptamers; and detecting the population of bound aptamers, thereby detecting the presence of the glycosylation site on the target polypeptide. In one embodiment of this aspect of the disclosure the subject target polypeptide is selected from the group consisting of an isolated polypeptide or a fragment thereof, a polypeptide of a cell or tissue of an animal or plant, and a cultured cell.

BRIEF DESCRIPTION OF THE DRAWINGS

Many aspects of the disclosure can be better understood with reference to the following figures.

See the text and examples for a more detailed description of the figures.

FIGS. 26A-26F illustrate the sequences of primers and templates used in the methods of the disclosure, and the aptamers identified by the methods of the disclosure.

DETAILED DESCRIPTION

Figure 1A:
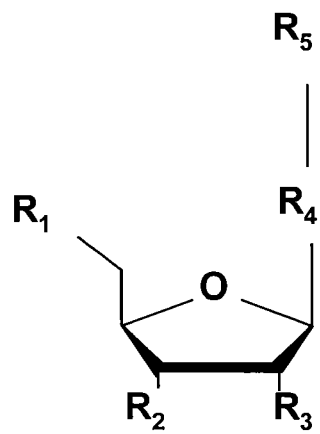
FIG. 1A illustrates an embodiment of the general structure of a modified nucleotide incorporating a boronic acid.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those skilled in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The term "aptamer" as described herein refers to an isolated nucleic acid molecule that binds with high specificity and affinity to a target molecule, such as a protein, polypeptide, lipid, glycoprotein, glycolipid, glycopeptide, saccharide, or polysaccharide. An aptamer is a three-dimensional structure held in certain conformation(s) that provide intermolecular contacts to specifically bind its given target. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not entirely dependent on a linear base sequence (a non-coding sequence), but rather a particular secondary/tertiary/quaternary structure. Any coding potential that an aptamer may possess is generally entirely fortuitous and does not contribute to the binding of an aptamer to its cognate target.

Aptamers must also be differentiated from the naturally occurring nucleic acid sequences that bind to certain proteins. These latter sequences generally are naturally occurring sequences embedded within the genome of the organism that bind to a specialized sub-group of proteins or polypeptides, or their derivatives, that are involved in the transcription, translation, and transportation of naturally occurring nucleic acids, i.e., protein-binding nucleic acids. Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can be selected to bind virtually any protein (not just nucleic acid-binding proteins) as well as almost any target of interest including small molecules, carbohydrates, peptides, etc. For most targets, even proteins, a naturally occurring nucleic acid sequence to which it binds does not exist. For those targets that do have such a sequence, i.e., nucleic acid-binding proteins, such sequences will differ from aptamers as a result of the relatively low binding affinity used in nature as compared to tightly binding aptamers. Aptamers are capable of specifically binding to selected targets and modulating the target's activity or binding interactions, e.g., through binding, aptamers may block their target's ability to function. The functional property of specific binding to a target is an inherent property an aptamer.

A typical aptamer is 6-35 kDa in size (20-100 nucleotides), binds its target with micromolar to sub-nanomolar affinity, and may discriminate against closely related targets (e.g., aptamers may selectively bind related proteins from the same gene family). Aptamers are capable of using intermolecular interactions such as hydrogen bonding, electrostatic complementarities, hydrophobic contacts, and steric exclusion to bind with a specific target. In the present disclosure, aptamers also employ boronic acid-Lewis base/nucleophile (such as hydroxyl groups, diols, and amino groups) interactions for binding. Aptamers have a number of desirable characteristics for use as therapeutics and diagnostics including high specificity and affinity, low immunogenicity, biological efficacy, and excellent pharmacokinetic properties.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL's ENCYCLOPEDIA OF PRACTICAL ORGANIC CHEMISTRY 5.sup.TH ED., Longman Scientific and Technical Ltd., Essex, 1991, pp. 809-816; and Heller, Acc. Chem. Res. 23: 128 (1990).

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present disclosure contain between about one and about twenty five carbon atoms (e.g., methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino", and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se, and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH═CH—O—$CH_3$, —Si($CH_3$)$_3$, —$CH_2$—CH═N—O$CH_3$, and —CH═CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R, —C(O)R', —CO2R', —CONR'R", —OC(O)NR'R", —NR"C(O)R', —NR'—C(O)NR"R"", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')q-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)r-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R'")d-, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C1-C6)alkyl.

As used herein, the term "heteroatom" includes oxygen (O), nitrogen (N), sulfur (S), phosphorus (P), silicon (Si), and selenium (Se).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "carboxyalkyl" as used herein refers to a group having the general formula —$(CH_2)_n$COOH, where n is 1-18.

The term "activated alkyne," as used herein, refers to a chemical moiety that selectively reacts with an alkyne reactive group, such as an azido moiety or an phosphine moiety, on another molecule to form a covalent chemical bond between the activated alkyne group and the alkyne reactive group. Examples of alkyne-reactive groups include azides. "Alkyne-reactive" can also refer to a molecule that contains a chemical moiety that selectively reacts with an alkyne group. As used herein activated alkyne encompasses any terminal alkynes or cyclooctynes (dipolarophiles) that will react with 1,3-dipoles such as azides in a facile fashion.

The term "azide reactive," as used herein, refers to a chemical moiety that selectively reacts with an azido modified group on another molecule to form a covalent chemical bond between the azido modified group and the azide reactive group. Examples of azide-reactive groups include alkynes and phosphines (e.g., triaryl phosphine). "Azide-reactive" can also refer to a molecule that contains a chemical moiety that selectively reacts with an azido group.

The term "click chemistry," as used herein, refers to the Huisgen cycloaddition or the 2,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

The term "cycloaddition" as used herein refers to a chemical reaction in which two or more π-electron systems (e.g., unsaturated molecules or unsaturated parts of the same molecule) combine to form a cyclic product in which there is a net reduction of the bond multiplicity. In a cycloaddition, the π-electrons are used to form new sigma bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 2,3-dipolar cycloadditions, occur between a 1,3-dipole and a dipolarophile and are typically used for the construction of five-membered heterocyclic rings.

The term "isolated", when used herein in reference to a nucleic acid polymer, means a nucleic acid polymer, which by virtue of its origin or manipulation is separated from at least some of the components with which it is naturally associated or with which it is associated when initially obtained. By "isolated", it is alternatively or additionally meant that the nucleic acid polymer of interest is produced or synthesized by the hand of man.

The term "linker" or "tether" as used herein, refers to a single covalent bond or a series of stable covalent bonds incorporating 1-30 nonhydrogen atoms selected from the group consisting of C, N, O, S and P. In addition, the linker may covalently attach a carrier molecule or solid support or a boronic acid moiety to the present azido or activated alkyne modified nucleotides or nucleic acid polymers. Exemplary linking members include a moiety that includes —C(O)NH—, —C(O)O—, —NH—, —S—, —O—, and the like.

The term "reactive group" as used herein refers to a group that is capable of reacting with another chemical group to form a covalent bond, i.e., is covalently reactive under suitable reaction conditions, and generally represents a point of attachment for another substance. As used herein, reactive groups refer to chemical moieties generally found in biological systems and that react under normal biological conditions, these are herein distinguished from the chemical handle, defined above, the azido and activated alkyne moieties of the present disclosure. As referred to herein the reactive group is a moiety, such as carboxylic acid or succinimidyl ester, that is capable of chemically reacting with a functional group on a different compound to form a covalent linkage. Reactive groups generally include nucleophiles, electrophiles and photoactivatable groups.

The term "reporter molecule" refers to any moiety capable of being attached to a carrier molecule or solid support, such as a modified nucleotide or nucleic acid polymer, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

The term "sample" as used herein refers to any material that may contain an analyte for detection or quantification or a modified nucleotide or nucleic acid polymer. The analyte may include a reactive group, e.g., a group through which a compound of the disclosure can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present disclosure can include groups that are activated or capable of activation to allow selected one or more compounds described herein to be bound to the solid support.

Figure 24:
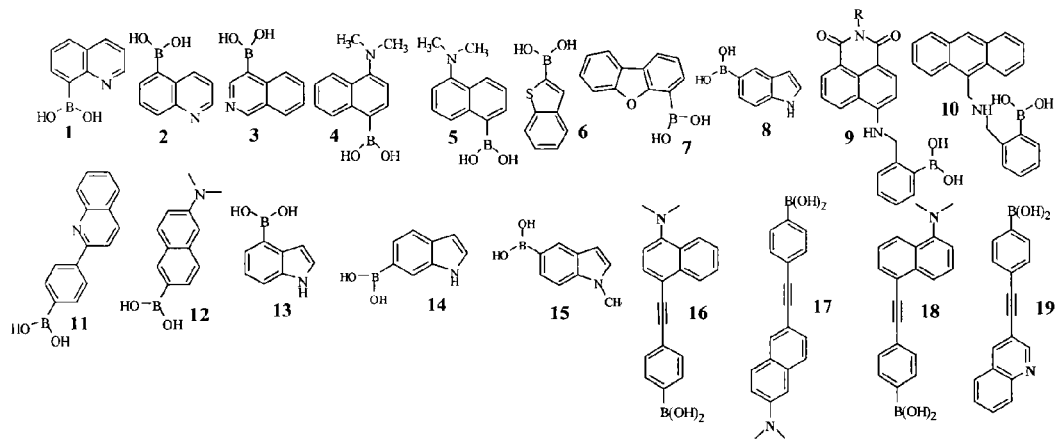
FIG. 24 illustrates fluorescent boronic acid compounds that respond to the binding of a diol with significant fluorescence intensity changes.
Figure 25:
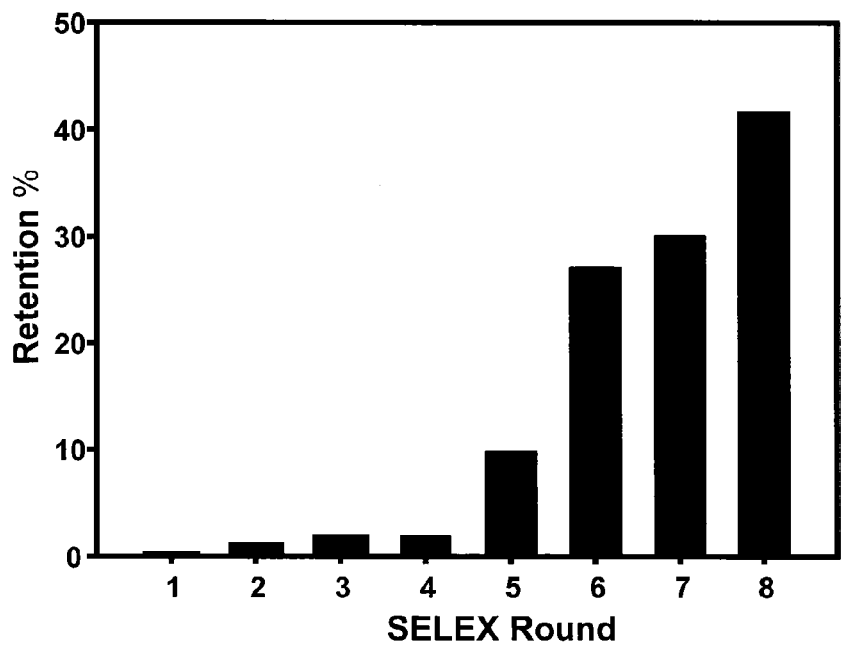
FIG. 25 illustrates the retention of radiolabeled aptamers on the PSA-immobilized beads during SELEX selection.

The term "boronic acid" as used herein refers to an alkyl or aryl substituted boronic acid containing a boron-carbon chemical bond. Boronic acid groups that may be used in the compositions of the present disclosure include, but are not limited to, arylboronic acids such as phenylboronic acids, naphthalenylboronic acids, quinolinylboronic acids, pyridinylboronic acids, furanylboronic acids, thiophenylboronic acids, indolylboronic acids, 1,8-naphthalimide-based boronic acids, and α-amidoalkylboronic acids. In addition, the boronic acid group can include, but is not limited to, fluorescent boronic acid groups as shown in FIG. 24, for example. In particular, the boronic acid group can include phenylboronic acid, naphthalenylboronic acid, quinolin-4- ylboronic acid, quinolin-5-ylboronic acid, quinolin-8-ylboronic acid, pyridinylboronic acid, furan-2-ylboronic acid, and thiophen-2-ylboronic acid.

Many cell surface and secretory proteins produced by eukaryotic cells are modified with one or more oligosaccharide groups. This modification referred to as "glycosylation," can dramatically affect the physical properties of proteins and can also be important in protein stability, secretion, and subcellular localization. Proper glycosylation can be essential for biological activity. In fact, some genes from eukaryotic organisms, when expressed in bacteria (e.g., E. coli) which lack certain cellular processes for glycosylating proteins, yield proteins that are recovered with little or no activity by virtue of their lack of glycosylation.

Glycosylation occurs at specific locations along the polypeptide backbone and is usually of two types: O-linked oligosaccharides are attached to serine or threonine residues while N-linked oligosaccharides are attached to asparagine residues when they are part of the sequence Asn-X-Ser/Thr, where X can be any amino acid except proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

The term "glycosylation site" as used herein refers to a location on a polypeptide that has a glycan chain attached thereto. The "site" may be an amino acid side-chain, or a plurality of side-chains (either contiguous in the amino acid sequence or in cooperative vicinity to one another to define a specific site associated with at least one glycosylation chain). The term "glycosylation site" as used herein further refers to a combination of a region of a polypeptide, and a region of a glycan chain attached to the polypeptide. Both regions may be recognized as binding, or affinity, sites by an aptamer having a specific affinity for the glycosylated species of the peptide. In particular, an aptamer having a boronic acid group(s) will have enhanced affinity for the glycosylation chain compared to an aptamer having the same nucleotide sequence but not having a boronic acid group thereon. Both aptamers will have affinity for the region of the polypeptide that is included in the glycosylation site.

As used herein, the terms "oligonucleotide" and "polynucleotide" generally refer to any polyribonucleotide or polydeoxyribonucleotide that may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above. Typically, aptamers are single-stranded oligonucleotides comprising between about 7 to about 100 nucleotides.

As used herein, the term polynucleotide includes DNAs or RNAs as described above that may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases such as, but not limited to, thymidine or uracil having a boronic acid group thereon are polynucleotides as the term is used herein.

The term "vector" as used herein means a DNA molecule serving as a vehicle capable of stably carrying exogeneous nucleic acid into host cells. A vector should be replicapable, have a system for introducing itself into a host cell, and possess selectable markers.

It will be appreciated that a great variety of modifications have been made to DNA and RNA that serve many useful purposes known to those skilled in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide.

A "nucleotide", "nucleotide monomer" and a "nucleotide moiety" refer to a sub-unit of a nucleic acid (whether DNA or RNA, or an analogue thereof) which includes, but is not limited to, a phosphate ester group, a sugar group and a nitrogen-containing base (alternatively referred to as a nucleoside), as well as analogs of such sub-units. Other groups (e.g., protecting groups) can be attached to the sugar group and nitrogen containing base group including, but not limited to, a boronic acid group according to the present disclosure, a radioactive or fluorescent substituent, a dye and the like.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangeable in many instances. One skilled in the art would have the understanding that additional modifications to a nucleoside may be necessary, and one skilled in the art has such knowledge.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

It will be appreciated that, as used herein, the terms "nucleotide" and "nucleoside" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its derivatives, inosine and its derivatives, alkylated purines or pyrimidines, acylated purines or pyrimidines thiolated purines or pyrimidines, selenium-modified nucleosidic bases, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature.

Common analogs include, but are not limited to, 1-methyladenine; 2-methyladenine; N6-methyladenine; N6-isopentyladenine; 2-methylthio-N6-isopentyladenine; N,N-dimethyladenine; 8-bromoadenine; 2-thiocytosine; 3-methylcytosine; 5-methylcytosine; 5-ethylcytosine; 4-acetylcytosine; 1-methylguanine; 2-methylguanine; 7-methylguanine; 2,2-dimethylguanine; 8-bromoguanine; 8-chloroguanine; 8-aminoguanine; 8-methylguanine; 8-thioguanine; 5-fluorouracil; 5-bromouracil; 5-chlorouracil; 5-iodouracil; 5-ethyluracil; 5-propyluracil; 5-methoxyuracil; 5-hydroxymethyluracil; 5-(carboxyhydroxymethyl)uracil; 5-(methylaminomethyl)uracil; 5-(carboxymethylaminomethyl)-uracil; 2-thiouracil; 5-methyl-2-thiouracil; 5-(2-bromovinyl)uracil; uracil-5-oxyacetic acid; uracil-5-oxyacetic acid methyl ester; pseudouracil; 1-methylpseudouracil; queosine; inosine; 1-methylinosine; hypoxanthine; xanthine; 2-aminopurine; 6-hydroxyaminopurine; 6-thiopurine, and 2,6-diaminopurine.

The term "randomized oligonucleotide aptamer" as used herein refers to a population of oligonucleotides wherein, at the same nucleotide position in each sequence, the nucleotide is adenine, guanine, cytosine or thymine.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "target" as used herein refers to a glycopolypeptide or glycoprotein, for which it is desired to detect or analyze the glycosylation status thereof. The target glycopolypeptide or protein for use in the methods herein disclosed may be an isolated glycopolypeptide or glycoprotein, a glycopolypeptide or protein immobilized on a solid support or in free solution. Alternatively, the target glycopolypeptide or protein may be on a cell surface, the cell being isolated from a plant or animal host, a cultured cell or a cell or population of cells in a tissue of a plant or animal.

The term "polypeptide" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

The term "conservative substitutions" as used herein refers to modifications of a polypeptide that involve the substitution of one or more amino acids for amino acids having similar biochemical properties that do not result in change or loss of a biological or biochemical function of the polypeptide. These "conservative substitutions" are likely to have minimal impact on the activity of the resultant protein. Amino acids that may be substituted for an original amino acid in a protein, and which are generally regarded as conservative substitutions are (original residue: conservative substitution): Ala: ser; Arg: lys; Asn: gln, his; Asp: glu; Cys: ser; Gln: asn; Glu: asp; Gly: pro; His: asn, gln; Ile: leu, val; Leu: ile, val; Lys: arg, gln; Met: leu, ile; Phe: met, leu, tyr; Ser: thr; Thr: ser; Trp: tyr; Tyr: trp, phe; Val: ile, leu. One or more conservative changes, or up to ten conservative changes, can be made in a polypeptide without changing a biochemical function of the polypeptide. For example, one or more conservative changes can be made in a Vstat40 or Vstat120 polypeptide without changing its ability to bind to CD36.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

Also, as used herein, the term "polypeptide" when used herein is similarly intended to refer to derivatives, analogues and functional mimetics thereof. For example, derivatives can include chemical modifications of the polypeptide such as alkylation, acylation, carbamylation, iodination, or any modification which derivatizes the polypeptide, including glycosylation and variations in the glycan chains thereof. Analogues can include modified amino acids, for example, hydroxyproline or carboxyglutamate, and can include amino acids that are not linked by peptide bonds. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

Discussion

The embodiments of the present disclosure encompass nucleotide monomers, oligonucleotides, and aptamers incorporating nucleotides modified as disclosed herein. The present disclosure further encompasses methods of preparation of each, methods of preparing specific types of aptamers, methods of preparing and identifying and selecting aptamers that have specific affinity for a glycoprotein (although the compositions and methods of the disclosure may also be applied to other target glycosylated biomolecular species such as, but not limited to, glycolipids, carbohydrates, and other glycoproducts), methods of preparing and identifying aptamers that have specific affinity for glycosylation sites and glycosylation states of target polypeptides, methods of biasing the identification of aptamers toward carbohydrate recognition, and the like.

Embodiments of the nucleotide monomers encompassed include a boronic acid group or moiety. Embodiments of oligonucleotides and aptamers may include one or more nucleotide monomers, where the nucleotide monomer includes a boronic acid group. Incorporation of a boronic acid moiety into one or more nucleotides of a polynucleotide (e.g., a DNA, DNA aptamers, an RNA, RNA aptamers, oligonucleotides, and the like) allow the oligonucleotide to recognize and bind to glycan chains, glycosylation sites and/or changes in the glycosylation status of a target biomolecule (e.g., carbohydrates, glycoproteins, glycopeptides, and glycolipids) by virtue of the strong binding between boronic acid and the glycans of the target biomolecule. In particular, the aptamers encompassed by the present disclosure are able not only to selectively recognize a glycoprotein, but also to distinguish differences in the glycosylation status of the glycoprotein.

There are several general approaches possible for conjugating a boronic acid moiety to a nucleotide monomer. "Click" chemistry, which uses chemistry orthogonal to all the other functional groups present, is one such approach. For example, the Huisgen cycloaddition may be used, which requires the presence of an azido group on one side and a terminal alkyne on the other (see, for example, FIG. 2). As a specific embodiment, the azido group was put on the boronic acid side and the alkynyl group on the modified thymidine (or its triphosphate) (see, for example, FIG. 3, compound 10). In another embodiment, the azido group is placed on the modified thymidine and the alkynyl group is placed on the boronic acid side.

The present disclosure provides methods for the preparation of aptamers that can recognize and/or be used to detect biomolecules having glycosylation sites, and/or recognize and/or detect changes in the glycosylation status of a biomolecule. In one embodiment of the disclosure, fibrinogen (a glycoprotein) was the target polypeptide and used to develop aptamers that can detect glycosylated fibrinogen at low concentrations (e.g., at nM concentrations). In another embodiment of the present disclosure, prostate specific antigen (PSA), a prostate cancer marker, was used to develop aptamers that can recognize glycosylation differences in prostate specific antigen. Additional details are provided in the specific examples below.

Embodiments of the present disclosure further encompass aptamers incorporating boronic acid groups, including boronic acids having fluorescent properties that may change upon binding. The latter embodiments of the present disclosure provide for aptamers and methods of detecting when the aptamer interacts with a biomolecule having a sugar group or multiple hydroxyl groups.

The nucleotide monomers of the present disclosure may each include a boronic acid group bonded (directly, or indirectly via a linking group) to the nucleosidic base (base) of the nucleotide monomer. The modified or labeled nucleotide monomers according to the present disclosure have an affinity for a glycan chain of a biomolecule due to the boronic acid affinity for the diol and/or hydroxyl group(s) of the oligosaccharide chain. The nucleotide monomers of the disclosure can include, but are not limited to, monomers such as those shown in FIGS. 1A, 1B, 21, and 27. One embodiment of the boronic acid labeled nucleotide monomer according to the present disclosure is shown in FIG. 1B as structure B-TTP (12).

The boronic acid group that may be conjugated to a nucleosidic base according to the present disclosure may be, but is not limited to, arylboronic acids such as phenylboronic acids, naphthalenylboronic acids, quinolinylboronic acids, pyridinylboronic acids, furanylboronic acids, thiophenylboronic acids, indolylboronic acids, 1,8-naphthalimide-based boronic acids, and α-amidoalkylboronic acids. In addition, the boronic acid group can be a fluorescent boronic acid group such as, but not limited to, those structures illustrated in FIG. 24. In particular, the boronic acid group can include phenylboronic acid, naphthalenylboronic acid, quinolin-4-ylboronic acid, quinolin-5-ylboronic acid, quinolin-8-ylboronic acid, pyridinylboronic acid, furan-2-ylboronic acid, and thiophen-2-ylboronic acid.

The boronic acid attached to a nucleotide according to the present disclosure may be linked to the nucleosidic base (base) thereof by a linking group, or tether, selected from the group of, but not limited to, an alkyl group, an alkylene group, an aryl or heteroaryl group, a cycloalkyl group, an alkoxy group, an aryloxy or heteroaryloxy group, an arylalkyl or heteroarylalkyl group, an arylalkyloxyl or heteroarylalkyloxyl group, or a combination thereof.

Figure 1B:
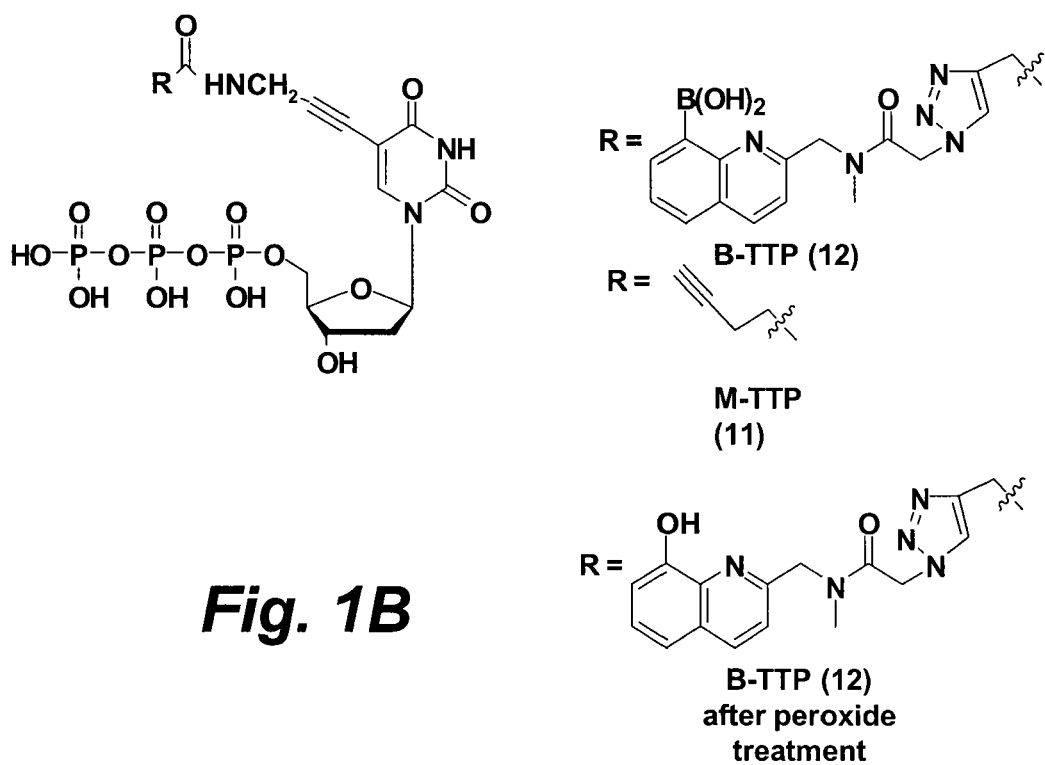
FIG. 1B illustrates the chemical structures of M-TTP (11) B-TTP (12), and peroxide treated B-TTP.

Referring now to the generalized nucleotide structure as illustrated in FIG. 1A, each of $R_1$ and $R_2$ may be, but is not limited to, a phosphate ester group (e.g., mono-, di-, or triphosphate ester group), thiophosphate (phosphorothioate), boranophosphate, and boranothophorothioate. Only one of $R_1$ and $R_2$ can be a phosphate group. $R_3$ can be, but is not limited to, H, and OH. In one embodiment, one or more of $R_1$, $R_2$, and $R_3$ can be a protecting group or other group used to enhance the preparation of the oligonucleotide. Advantageously, $R_2$ and $R_3$ are HO— and H—, respectively.

The base $R_5$ can be a naturally occurring purine or pyrimidine base, e.g., adenine (A), thymine (T), cytosine (C), guanine (G), hypoxanthine, or uracil (U), but also modified purine and pyrimidine bases and other heterocyclic bases which have been modified (these moieties are sometimes referred to herein, collectively, as "purine and pyrimidine bases and analogs thereof"). In one particular embodiment of the disclosure, the base is thymine (see Examples 1 and 2).

The modified nucleotides according to the present disclosure may be incorporated into oligonucleotides to generate libraries of randomized sequences. It is necessary, therefore, to select from such heterogeneous libraries the oligonucleotides or aptamers with the desired specific affinities for a target glycosylated polypeptide or protein. Accordingly, the Systematic Evolution of Ligands by Exponential Enrichment (SELEX) approach for aptamer selection (Science 1990, 249: 505; *J. Mol. Biol.* 1991, 222: 739, U.S. Pat. No. 5,270,163, each of which are incorporated herein by reference) was used, as shown schematically in FIG. 20, to identify desired aptamers from a pool or library of oligonucleotides, the desired aptamers having biased affinity for glycan, and most preferably for distinct glycosylation sites of a target polypeptide or protein. The aptamers manufactured and selected according to the disclosure, therefore, have selective affinity to a region of the target glycopolypeptide, thereby conferring on the aptamer specificity for the glycopolypeptide itself, and to a region of the glycan attached to the polypeptide. By being selected for the dual affinities, the isolated aptamer(s) will specifically recognize a glycosylated form of the target glycopolypeptide, and not just the polypeptide itself, or a glycan chain alone. In general, the SELEX method includes contacting a mixture of oligonucleotides, each oligonucleotide preferably including a segment of randomized sequence, with the target polypeptide (e.g., PSA or fibrinogen) under conditions favorable for binding, partitioning unbound oligonucleotides from those oligonucleotides that have bound to target molecules, dissociating the oligonucleotide-target pairs. The oligonucleotides dissociated from the oligonucleotides-target pairs may be amplified to yield a ligand-enriched mixture of oligonucleotides, then repeating the steps of binding, partitioning, dissociating and amplifying through as many cycles as desired (e.g., 2 to 20, 4 to 20, or 13 to 14).

In a counter-selection step, the aptamers are amplified using dTTP so that the amplified products do not include a boronic acid label. These unlabeled aptamers are then counter-selected using glycosylated target polypeptide or protein, such as fibrinogen. Consequently, the unbound aptamers from this third counter-selection step are those that have biased affinity for the glycan of the target polypeptide or protein only when they include a boronic acid label. Counter-selection, using a deglycosylated target polypeptide will eliminate those aptamers selectively binding to sites on the polypeptide alone. Counter-selection, using micro-beads alone will partition out those aptamers binding to the beads themselves.

The selection process of the present disclosure is not limited in the nature of the target polypeptide or protein. It is contemplated that the selection methods herein disclosed may also be applied to glycoprotein targets including, but not limited to, prostate specific antigen (PSA), mucin, human carcinoembryonic antigen, human pancreatic RNase 1, tumor-associated glycoproteins (TAG-72), CA 125, major histocompatibility complex (MHC), human chorionic gonadotropin (hCG), alpha-fetoprotein (AFP), haptoglobin (Hp), antibodies, hormones, and human glycoproteins 96 (a tumor-rejection protein) and the like.

The aptamer selection process gravitates toward strong sugar (glycosylation portion) recognition in glycoproteins. As described herein, boronic acids are known to interact strongly with diol-containing compounds and simple Lewis bases and nucleophiles such as a hydroxyl group. These are commonly found on carbohydrates. Such interactions can be used for carbohydrate recognition. While not wishing to be limited to any one theory, the incorporation of a boronic acid moiety into an oligonucleotide aptamer, on account of the significant affinity of the boronic acid for saccharides, and in particular diol and hydroxyl groups thereof, enables the selection process to isolate those aptamers binding to a carbohydrate sub-structure. This therefore allows for recognition of the glycoprotein and the ability to recognize differences in glycosylation states of the polypeptide.

Example 1 below describes the chemistry, and the methods thereof, whereby a boronic acid moiety was linked to the 5'-position of thymidine-5'-triphosphate resulting in B-TTP (12), as shown in FIG. 1B. Modification at this position is known to have minimal effect on polymerase-catalyzed incorporation. The 5-position boronic acid-labeled thymidine-5'-triphosphate (B-TTP) can be successfully incorporated into DNA using DNA polymerases and the synthesized boronic acid-modified DNA (B-DNA) can serve as templates for further amplification, as described in Example 6.

In the SELEX selection process as described in Example 10 below, fibrinogen was immobilized to magnetic beads using amidation chemistry. It is contemplated, however, that the target polypeptide or protein may be bound to any suitable solid support that will allow separation of the target and bound aptamer from the remaining unbound aptamer pool. Alternatively, the target polypeptide or protein may be conjugated to a group that allows for the separation of bound and unbound aptamer. For example, it is contemplated that the target protein could be conjugated to a biotin group, and the polypeptide could then be isolated from the unbound, non-specific aptamer using streptavidin bound to magnetic beads. In addition, the target polypeptide could be precipitated with a specific antibody, leaving unbound aptamer in suspension. In the example described in the present disclosure, a library of DNA oligonucleotides each containing 50 randomized positions was first amplified by PCR. The incorporation of boronic acid-modified nucleotide (B-TTP) was performed in the last round of polymerase reaction using a single primer. Accordingly, there was minimal exposure of the boronic acid moiety to the high temperature cycles necessary for PCR, even though the boronic acid moiety is stable under PCR conditions. Finally, the boronic acid labeled single stranded DNA library was exposed to fibrinogen-immobilized beads. Aptamers bound to immobilized fibrinogen were recovered and re-amplified.

After selection and counter selection (counter-selection against blank beads and using all natural dNTPs), the fibrinogen-specific enriched DNA library was cloned into *E. coli* using the TOPO TA CLONING™ Kit for sequencing (Sigma, St. Louis, Mo.). Colonies were randomly selected for sequence analysis, and several of the aptamers were selected for further analysis. The selection could be based, at least in part, upon the appearance of the sequences in both pre-counter-selection and post-counter-selection pools.

Dissociation constants of the aptamers, which can be determined using equilibrium filtration, provided the degree to which the aptamers bind specifically to fibrinogen. The dissociation constants obtained for the aptamers could then be compared to one or more controls to determine the strength of the association. For example, the aptamers may have a $K_d$ at the nanomolar level (e.g., about 6 nanomolar).

Synthesis and Properties of Boronic Acid Labeled Aptamers

A boronic acid moiety can be covalently linked to a nucleoside triphosphate that is then used in DNA polymerization and amplification reactions. The 5'-position modification of deoxyuridine can be tolerated by polymerases and reverse transcriptases, although whether the attachment of a boronic acid moiety interfered with these reactions was not apparent. The strong Lewis acidity of the boronic acid moiety can lead to tight interactions with Lewis bases commonly found on nucleic acids and enzymes. These interactions are, therefore, distinguishable from the attachments of other organic functional groups at the 5'-position of deoxyuridine, by possibly including impeded incorporation and amplification, added secondary structures in the DNA products, enzyme binding and inhibition, and even inter-strand interactions.

For minimal interference of the polymerase reaction, a long and somewhat linear linker or tether was used. The Huisgen cycloaddition, which has been extensively used in "click chemistry" (performed with and without microwave irradiation) was selected for the coupling of the boronic acid moiety with the nucleoside, although it is contemplated that other suitable schemes may also be used as appropriate for the particular boronic acid or nucleosidic base selected. B-TTP (compound (12), as shown in FIG. 1B), was designed as an exemplary monomeric building block for DNA polymerization. An 8-quinoline boronic acid analog was selected because of its affinity for various sugars, and its water solubility. Successful incorporation of this large arylboronic acid into an oligonucleotide indicated that other smaller arylboronic acid analogs would possibly have minimal difficulty being incorporated. A quinoline boronic acid analog with an azido group and a 5-modified deoxyuridine analog with an alkyne group were also desirable. The synthesis of the quinoline boronic acid followed the procedures described in Example 1 below, and is schematically illustrated as Scheme 1 in FIG. 2.

Figure 2:
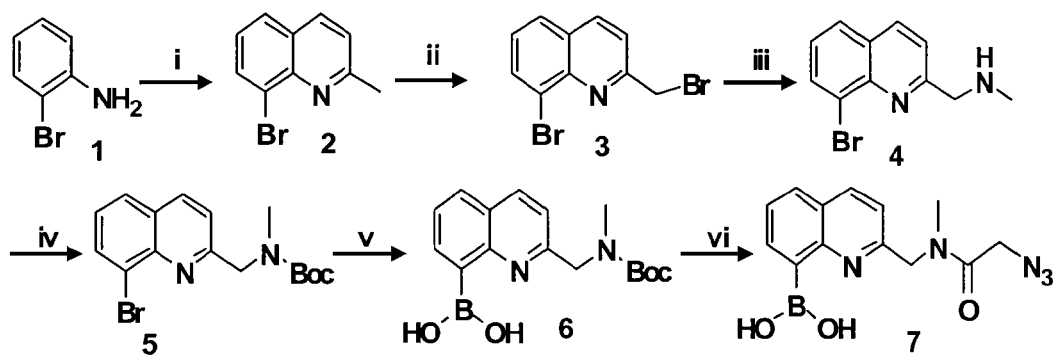
FIG. 2 illustrates Scheme 1 for the synthesis of quinoline boronic acid. Reagents used in the steps of the Scheme 1 are as follows: Step (i) crotonaldehyde, 6 N HCl, reflux, 56%; Step (ii) NBS, AIBN, $CCl_4$, 39%; Step (iii) $MeNH_2$ (40%, wt), THF, 96%; Step (iv) $(Boc)_2O$, TEA, methanol, 97%; Step (v) $Pd(dppf)Cl_2$, bis(neopentyl glycolato)diboron, KOAc, DMSO, 90%; and Step (vi) TFA; DCM, azido acetic acid, CDI, iPrNEt, 68%.

Therefore, the synthesis of the quinoline boronic acid building block according to the methods of the present disclosure and described in detail in Example 1 below, started with commercial available 2-bromoaniline (1) (for the chemical structures, refer to FIG. 2), which was converted to 2-methylquinoline (2) by refluxing with crotonaldehyde in 6N HCl. Bromination at methyl group gives compound (3), which was reacted with 40% methylamine aqueous solution in THF to yield (4). The amino group was first protected with Boc before borylation under the catalysis of dichloro-(bis-diphenylphospino)ferrocenyl)-palladium [Pd(dppf)Cl$_2$] to give compound (6). Deprotection by TFA followed by amide formation with azido acetic acid generated the quinoline boronic acid (7), as shown in FIG. 2.

Figure 3:
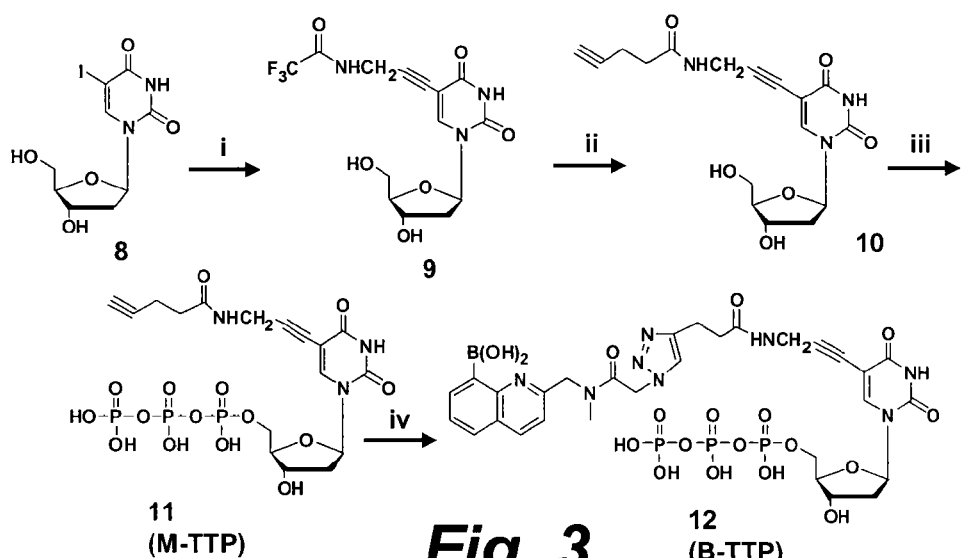
FIG. 3 illustrates Scheme 2 for the synthesis of B-TTP (compound (12)). Reagents used in the steps of the Scheme 2 are as follows: Step (i) N-propynyltrifluoroacetamide, $Pd(PPh_3)_4$, CuI, $Et_3N$, DMF, 67%; Step (ii) ammonium hydroxide, MeOH; then pentynoic acid, PyBop, DMF; Step (iii) Proton sponge, $POCl_3$ trimethylphosphate, bis-tri-n-butylammonium pyrophosphate, tri-n-butylamine; and Step (iv) (7), sodium ascorbate, $CuSO_4$, $EtOH/H_2O$/t-butyl alcohol (3:2:5).

For the synthesis of the final B-TTP (compound (12)), shown as Scheme 2 illustrated in FIG. 3, there are two possible general approaches. The first one is to attach the boronic acid before triphosphorylation. The second one is to triphosphorylate before the attachment of the boronic acid moiety. In both approaches, the synthesis starts with 5-iodo-2'-deoxyuridine (8). An alkyne side chain may then be attached to the 5-position. Deprotection of the amino group and introduction of a terminal alkyne group results in the intermediate (10).

The boronic acid was attached to nucleoside (10) after preparing the triphosphate (11). The subsequent Huisgen cycloaddition allowed for the tethering the quinoline boronic acid moiety to give (12). The final product was purified by a DEAE-Sephadex A-25 followed by reversed-phase C18 HPLC. Thermal stability studies using NMR under PCR conditions demonstrated that the boronic acid moiety did not present additional stability problems.

Since a goal of the synthetic chemistry was the synthesis of a boronic acid-labeled nucleotide that could be incorporated into DNA, a primer extension reaction using B-TTP (12) was conducted using oligonucleotide Template 21-nt (SEQ ID NO.: 8) and Primer 14-nt (SEQ ID NO.: 9), as described in Example 5. More detailed examination of the ability of B-TTP to be incorporated was conducted through the extension of a Primer 1 (SEQ ID NO.: 2) on the oligonucleotide Template 1 (SEQ ID NO.: 4). This longer template had three adjacent A's in the sequence allowing for the incorporation of three T's, or labeled T's bearing a boronic acid group. The time-dependent incorporation of B-TTP compared with natural TTP using a $^{32}$P-labeled primer was also studied. Gel electrophoresis results showed that the full-length DNA was obtained from primer extension reactions, as described in Example 3 and shown in FIG. 5, which was confirmed by mass spectrometry.

Figure 7:
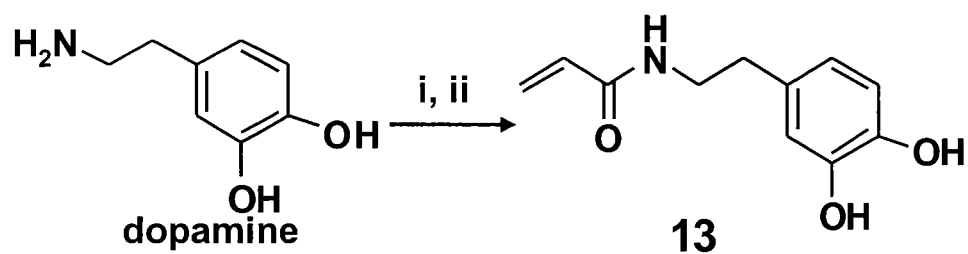
FIG. 7 illustrates Scheme 3 for the synthesis of catechol-modified acrylamide (13). Steps: (i) triethylamine, TMSCl; acryloyl chloride; (ii) trifluoroacetic acid, dichloromethane.
Figure 8:
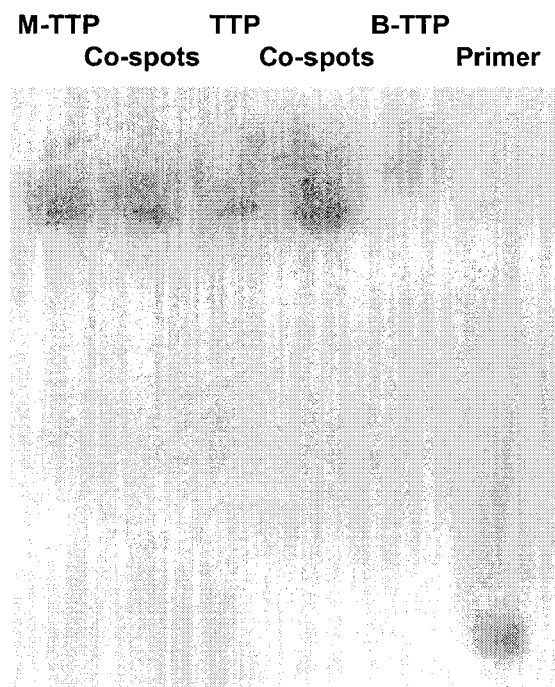
FIG. 8 illustrates gel-shifting experiments of full length natural and boronic acid-labeled DNA using a 19% catechol-modified acrylamide and 1% N-[2-(3,4-dihydroxyphenyl)-ethyl]-acrylamide gel. Lane loadings were as follows: Lane 1, M-TTP derived DNA; lane 3, TTP derived DNA; lane 5, B-TTP derived DNA; lane 6, primer; lane 2, M-TTP and TTP derived DNA co-loaded; and lane 4, TTP and B-TTP derived DNA co-loaded.

To allow for quick confirmation of boronic acid incorporation into DNA using electrophoresis, a gel-shift method was also developed by using a low percentage of acrylamide (1%) modified with catechol, which was synthesized as shown in Scheme 3, FIG. 7 and described in Example 4. Because catechol is known to form a tight complex with a boronic acid moiety, such gels were expected to exert extra retention power for boronic acid-containing DNA and, therefore, allow their separation from natural DNA of the same length and composition. FIG. 8 illustrates the successful application of such a catechol-embedded acrylamide gel and its ability to differentiate the boronic acid-labeled DNA from that of the natural one. Specifically, when analyzed on the catechol-modified acrylamide gel, only the natural and non-boronic acid modified DNA (using M-TTP (11)) showed the same retention. The DNA labeled with boronic acid through the incorporation of B-TTP (12) moved more slowly compared with the other two, as expected based on the known interaction between boronic acid and catechol. This was confirmed by co-loading these two different samples on the same lane (FIG. 8, tracks 2 and 4).

Boronic acid-labeled DNA can serve as a template for further polymerization and amplification. To demonstrate the recognition of boronic acid-labeled full-length DNA as templates by the Klenow fragment, two 20-nucleotide primers (Primers 2 and 3, SEQ ID NOs.: 3 and 5 respectively) were synthesized and analyzed in FIG. 9. The polymerase reactions using the boronic acid-labeled DNA as the template and with M-TTP (11), TTP, or B-TTP (12) and the other three dNTPs as the monomers, were carried out first with Primer 2 (SEQ ID NO.: 3), which is complementary to the 3'-terminus of the oligonucleotide Template 1 (SEQ ID NO.: 4).

Figure 9:
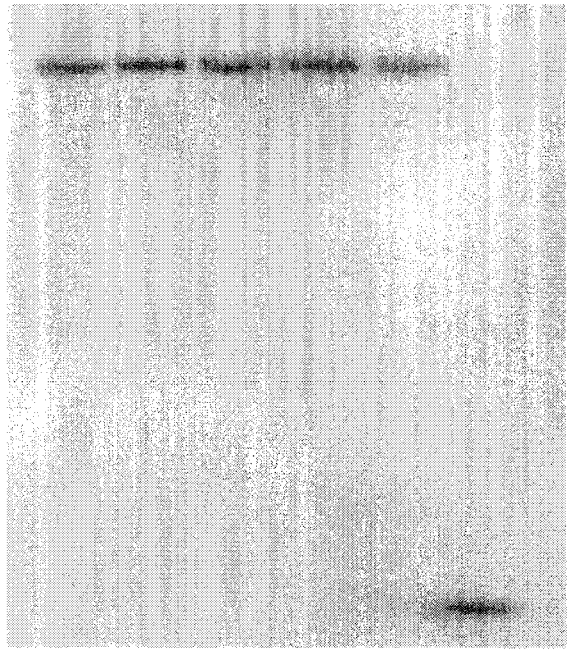
FIG. 9 illustrates the results of primer extension using the full-length DNA and boronic acid-labeled DNA as template. Reactions were performed with 5 µM Primer 1 (SEQ ID NO.: 2) and oligonucleotide Template 1 (SEQ ID NO.: 4). After centrifugation-filtration, the reaction was performed with radio-labeled 5'-$^{32}$P-Primer 2 (SEQ ID NO.: 3). Co-spot 1: polymerization using M-TTP and TTP-derived DNA as templates, and Co-spot 2: polymerization using B-TTP and TTP-derived DNA as templates.

After primer extension, the full-length DNA obtained was purified by membrane filtration to remove the labeled and non-labeled dNTPs. Then further polymerization was conducted using natural dNTPs and 5'-$^{32}$P-labeled Primer 3 (SEQ ID NO.: 5). Gel electrophoresis of the DNA products showed no noticeable differences between using natural and labeled full-length DNA as templates, as shown in FIG. 9, indicating that all full-length DNA templates generated using M-TTP, TTP and B-TTP in the first primer extension were efficiently recognized with a similar efficiency by the polymerase.

Figure 10:
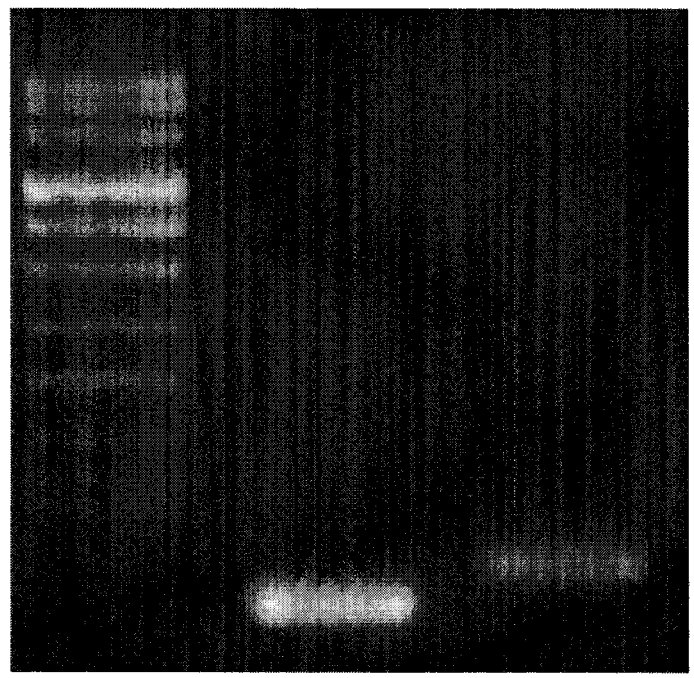
FIG. 10 illustrates the result of a primer extension using the full-length DNA and boronic acid-labeled DNA as template. Each 50 µl reaction was performed with 1.2 µM of primers 3 and 4 (SEQ ID NOs.: 5 and 6 respectively) and oligonucleotide Template 2 (SEQ ID NO.: 7), 0.25 mM of each dNTP, 0.25 mM of labeled-TTP (B-TTP), and 3.5 units of High Fidelity DNA polymerase (Roche, Indianapolis, Ind.) under conditions of 1 cycle at 94° C. for 2 min, 30 cycles at 94° C. for 20 s, 59° C. for 30 s, 72° C. for 1 min, and 1 cycle at 72° C. for 7 min. Lane 1: Marker; lane 2: DNA synthesized using dNTPs; and lane 3: DNA synthesized using B-TTP and the other three dNTPs.

To confirm the general feasibility of incorporating the boronic acid labeled TTP (B-TTP) into DNA, similar studies using a different template were carried out (Primers 3 (SEQ ID NO.: 5), Primer 6 (SEQ ID NO.: 4) with Template 2 (SEQ ID NO.: 7). The results again demonstrated the synthesis of the full-length DNA using B-TTP. Furthermore, using an agarose gel run with an extended time run, the boronic acid-labeled DNA was differentiated from the non-labeled DNA, which is consistent with the increased molecular weight of the boronic acid-labeled DNA, as shown in FIG. 10. Boronic acid also has a pKa of about 9 and is mostly charge-neutral under the electrophoresis conditions (buffer pH 8.3).

Carbohydrate Substructure-Specific DNA Aptamer Selection

Carbohydrate substructure-specific DNA aptamer selection according to the present disclosure allows the recognition of a glycoprotein and differences in its glycosylation state. It is also contemplated that the methods and compositions of the present disclosure are applicable in the selection of RNA aptamers and for the recognition of other glycosylated products such as glycolipids.

Figure 20:
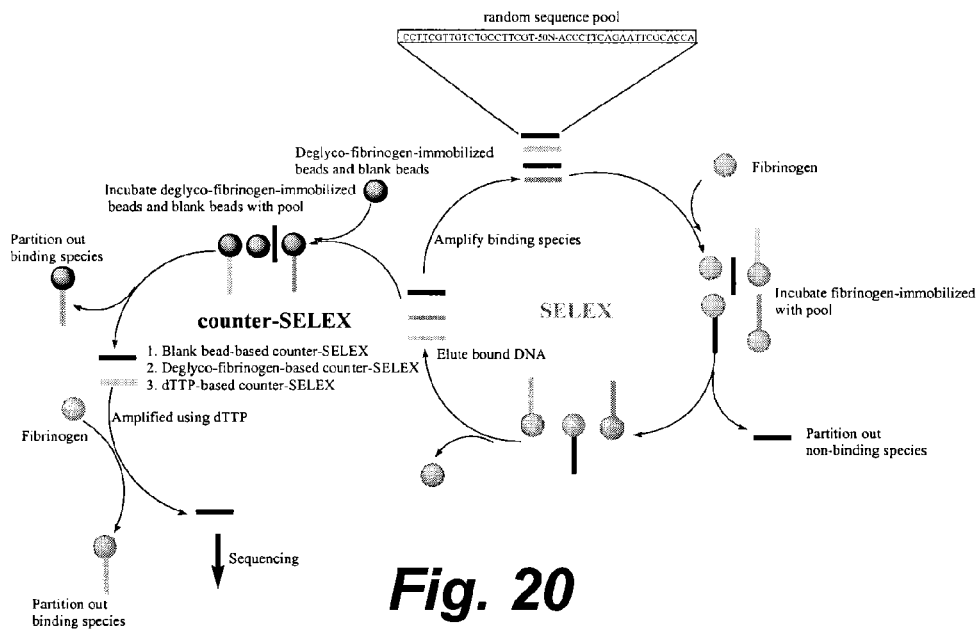
FIG. 20 illustrates Scheme 4 for the SELEX selection of DNA aptamers specific for a glycosylation site of fibrinogen.

The Systematic Evolution of Ligands by Exponential Enrichment (SELEX) approach for aptamer selection (*Science* 1990, 249, 505; *J. Mol. Biol.* 1991, 222, 739) was used. The SELEX approach to aptamer selection according to the present disclosure is shown in FIG. 20. It involves the synthesis of a DNA oligonucleotide library where the oligonucleotides have invariant sequences at each end. The sequence of the middle portion of each oligonucleotide is randomized to create the combinatorial library. The theoretical number of 40-mer combinations is about $1.2 \times 10^{24}$, although in the Examples of the present disclosure a library of about $10^{14}$ unique sequences was used.

The library, after PCR amplification, can be exposed to target polypeptides or proteins immobilized on beads. Those oligonucleotides that have affinity for the target ligand will remain bound to the bead and get enriched. Non-binding oligonucleotides are partitioned and washed away with buffer. Release of the bound DNAs using strong eluting conditions will separate the beads from the aptamers, which can be PCR amplified. This process constitutes one round of selection. Repetition of this procedure allows for the enrichment of aptamers that have high affinities for the target ligand. When necessary, counter selection can be used to eliminate unwanted cross-reactivity. In a counter selection step, the counter selection ligand can be immobilized to the beads so as to remove those aptamers with cross-reactivity with the counter selection ligand. The result of the selection procedures of the present disclosure are aptamers biased to an affinity for a glycan chain of a specific target polypeptide. In this approach, $K_d$ values for aptamer-target binding (in some cases it is the $IC_{50}$) in the concentration range of low nM to pM are achievable.

In one example of aptamer selection, fibrinogen was immobilized to magnetic beads using amidation chemistry. A library of aptamer oligonucleotides containing 50 randomized positions was then amplified by PCR. The incorporation of boronic acid-modified nucleotide (B-TTP) was performed in the last round of polymerase reaction using a single primer. This single stranded DNA library was then exposed to fibrinogen-immobilized beads. DNA bound to immobilized fibrinogen was isolated and re-amplified. Radioactive dATP was used to incorporate a radio-tracer for binding detection.

Figure 11:
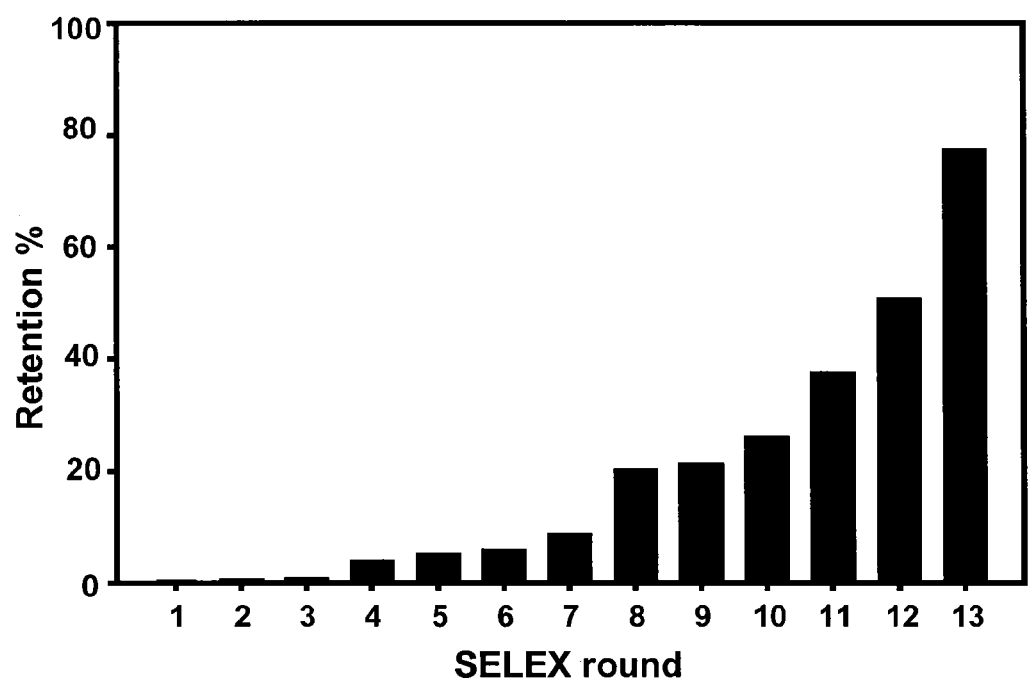
FIG. 11 illustrates retention of radioactive DNA on fibrinogen-immobilized beads over 13 rounds of selection.

Throughout the process, the percentage of radioactivity retained by immobilized fibrinogen was monitored as shown in FIG. 11. After the $4^{th}$ round of selection, there was significant enrichment of radioactivity in the fibrinogen-bound fraction, as shown in FIG. 11. After the $8^{th}$ round, there was over 20% of radioactivity retention by the immobilized fibrinogen. After the $13^{th}$ round, nearly 80% of the radioactivity was retained by immobilized fibrinogen, indicating a high percentage of specific binders for the target glycoprotein.

To minimize the selection of non-specific binders and those that would only bind to the protein portion of the glycoprotein, several counter-selection steps were built into the process. After the $6^{th}$ round, the library was counter-selected against blank beads alone. The aim was to remove those aptamers that had non-specific binding to the bead matrix. In addition, many aptamers without boronic acid incorporation may bind to fibrinogen. However, without the "pull" of the boronic acid moiety toward carbohydrates, such aptamers may randomly bind to various parts of fibrinogen without focusing on the glycosylation site, which would be undesirable. Therefore, to "select out" this pool that had no intrinsic preference for carbohydrates, and after the $13^{th}$ round, the library was amplified using all natural dNTPs (without B-TTP) and the amplification products were incubated with immobilized fibrinogen. In this step, the only material collected was whatever remained unbound to the immobilized fibrinogen. Aptamers that could bind to fibrinogen without involving boronic acid interactions, and therefore did not have an intrinsic preference for carbohydrates, were eliminated. Such a counter selection step also allowed elimination of those aptamers that may have boronic acid incorporated, but do not depend on them for binding. Such aptamers probably would not have an intrinsic preference for carbohydrates either.

After selection and counter selection, the enriched DNA library for each selection was cloned into *E. coli*. Several hundred of colonies appeared after overnight incubation of the transformed *E. coli*. Twenty colonies were randomly selected for sequence analysis. The sequences of aptamers thus selected as having a bias for a glycan chain of fibrinogen are shown in FIG. 26A-F as SEQ ID NOs.: 13-58. Among the 20 colonies, the aptamer sequences of which were selected against glycosylated fibrinogen, three sequences, 85A (SEQ ID NO.: 13), 85B (SEQ ID NO.: 14), and 85C (SEQ ID NO.: 15), appeared in both pre-counter-selection and post-counter-selection pools, and were selected for further analysis.

Figure 19A:
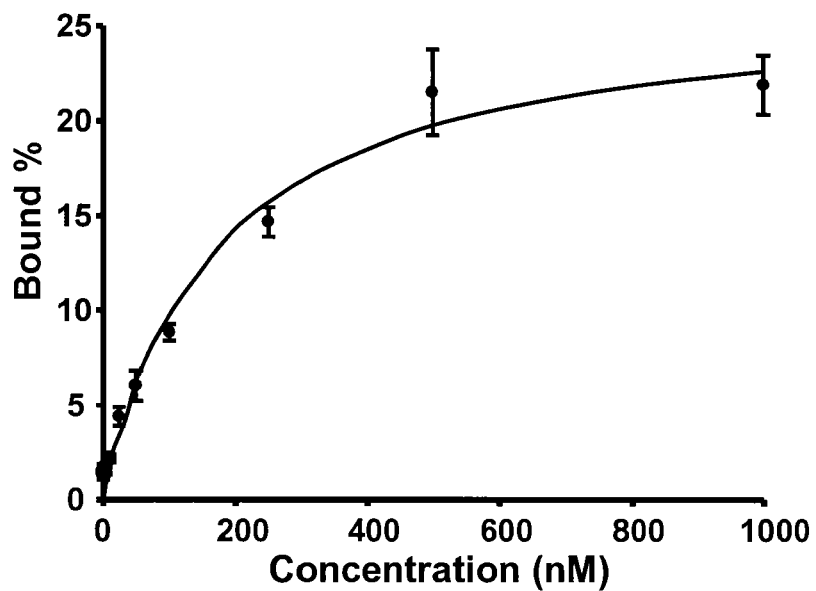
FIG. 19A is a binding curve of peroxidated B-TTP-labeled 85A aptamer with fibrinogen.
Figure 19B:
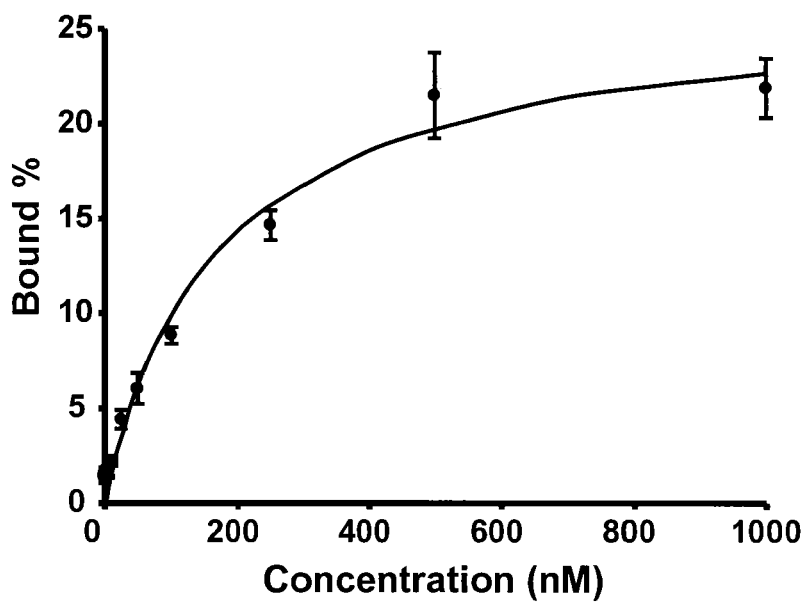
FIG. 19B is a binding curve of peroxidated TTP-85A aptamer with fibrinogen.

Also prepared was DNA using a modified TTP (M-TTP (11), FIG. 1) as a control but which included a side chain that was not the boronic acid moiety. The M-TTP version of aptamer 85A showed a $K_d$ value (138 nM), which is 20 fold higher than that of the corresponding B-TTP-labeled aptamer. As an additional control study, B-TTP aptamer was treated with 30% hydrogen peroxide for 5 min at room temperature to remove the boronic acid group. The resulting aptamer showed a much higher $K_d$ value (173 nM) than did the B-TTP aptamer (FIG. 19A). Control experiments showed that the same hydrogen peroxide treatment of TTP aptamer resulted in no significant change in its $K_d$ (139 nM) indicating DNA was stable under the hydrogen peroxide treatment conditions (FIG. 19B).

With the decreased affinity of the TTP and M-TTP aptamers, the percentage of radioactivity of these two aptamers bound to fibrinogen is also much lower. For example, in the binding study between B-TTP aptamer with fibrinogen, at saturation about 60% of the radioactivity was retained on fibrinogen. In contrast, TTP and M-TTP aptamers showed only 25% and 20% radioactivity retention, respectively. Such results indicate that without boronic acid, there is a higher percentage of aptamer that does not adapt the needed conformation for proper binding to fibrinogen.

The involvement of the boronic acid functional group in binding indicates that the aptamer binds to fibrinogen through at least some interactions with the carbohydrate sub-structure. To further examine this, deglycosylated fibrinogen was prepared according to the protocol of Weber (*Anal. Biochem.* 1981, 118, 131; *Biochem. J.* 2003, 376, 339). Also, fibrinogen was treated with periodate, which cleaves diol structures on carbohydrates and therefore, changes the structural features of the carbohydrate portion of the glycoprotein. As shown, for example, in FIGS. 14A-15B and 17A-18B, significantly reduced binding affinity for these aptamers was observed with deglycosylated and periodate-treated fibrinogen. For example, with deglycosylated fibrinogen, B-TTP aptamer 85A showed a 60-fold lower affinity with a $K_d$ of 390 nM. On the other hand, the TTP aptamer of 85A showed a $K_d$ of 60 nM and the M-TTP aptamer 148 nM. With periodate-treated fibrinogen, the B-TTP aptamer 85A aptamer showed about 10-fold lower affinity than their binding with unmodified fibrinogen with $K_d$ of 70 nM. Such results suggest that the sugar portion is indeed intimately involved in the binding. Also, the aptamer binds to fibrinogen even after sugar modification. This indicates that the aptamers also recognize the protein portion of fibrinogen, which is very much desirable since aptamers that only bind to the sugar portion would not have limited diagnostic value for the specific recognition of an intact glycoprotein due to possible interference by other carbohydrates.

After the 13$^{th}$ round of counter-selection, the pool was counter selected against immobilized deglycosylated fibrinogen in one more round. The solution portion which should have aptamers that rely on recognition of the carbohydrate portion for tight binding was collected. Twenty colonies were picked after cloning the pool into *E. coli*. Out of these 20, 16 sequences also appeared in the previous batch selected without this last counter selection step. The aptamers from both selections are SEQ ID NOs.: 13-58, shown in FIG. 26.

Though the binding constants of B-TTP aptamers changed very significantly when the carbohydrate portion of fibrinogen was modified, the change in binding affinity for TTP aptamers was much less significant. TTP aptamers do not have the boronic acid functional group to provide strong interactions with the carbohydrate moiety. Therefore, changes in carbohydrate structures, whether it is their removal or oxidation, are not expected to significantly affect TTP aptamer binding. Such results indicate that the structure of the non-carbohydrate portion did not change much to affect TTP aptamer binding.

Fluorescent Aptamers

The present disclosure further encompasses incorporating fluorescent boronic acids that change fluorescent properties upon sugar binding. Such boronic acid-nucleotide conjugates are useful for the preparation of boronic acid-modified aptamers for detection and/or recognition of carbohydrate-containing molecules such as glycoproteins, glycolipids, glycopeptides, aminoglycosides, and carbohydrates.

Figure 22:
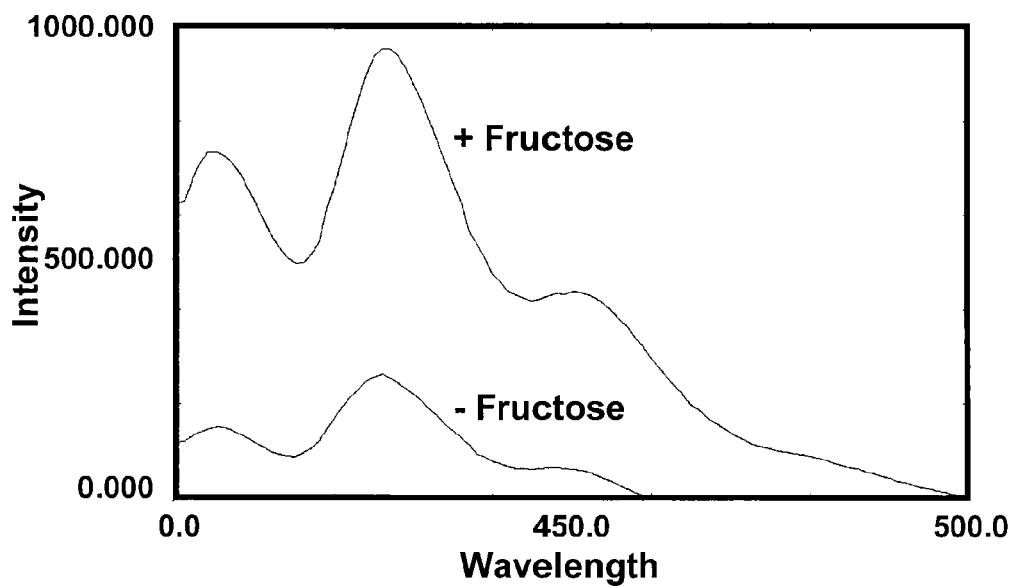
FIG. 22 is a graph illustrating fluorescence intensity changes of compound (4) of Scheme 5 after binding with fructose.
Figure 23:
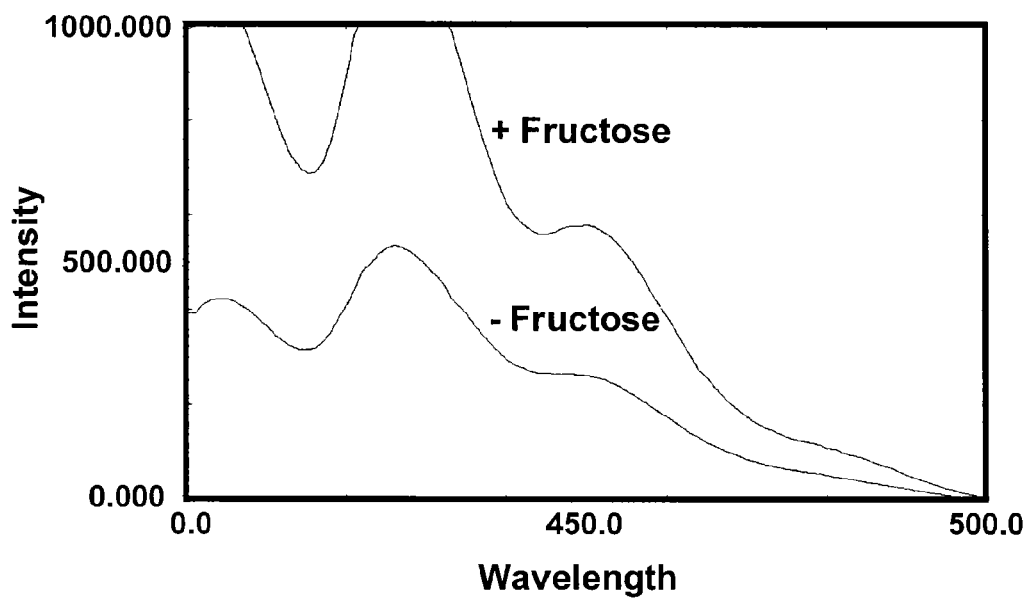
FIG. 23 is a graph illustrating fluorescence intensity changes of compound (6) of Scheme 5 after binding with fructose.

Some boronic acids that show significant changes in fluorescent properties upon binding to saccharides are illustrated in FIG. 24, including 8-quinolineboronic acid (6), 5-quinolineboronic acid (7), isoquinolineboronic acid (8), 4-dimethylaminonaphthaleneboronic acid (9), 5-dimethylaminonaphthaleneboronic acid (10), 2-thiopheneboronic acid (11), dibenzofuran-boronic acid, indoleboronic acids (e.g., 12), amidoboronic acids (e.g. 13) naphthalimide-based boronic acid (14). FIGS. 22 and 23 show two typical examples of such fluorescent property changes by these reporter compounds.

Synthesis of Naphthalimide-based Long-wavelength Boronic Acid Modified TTP (N-TTP)

Figure 27:
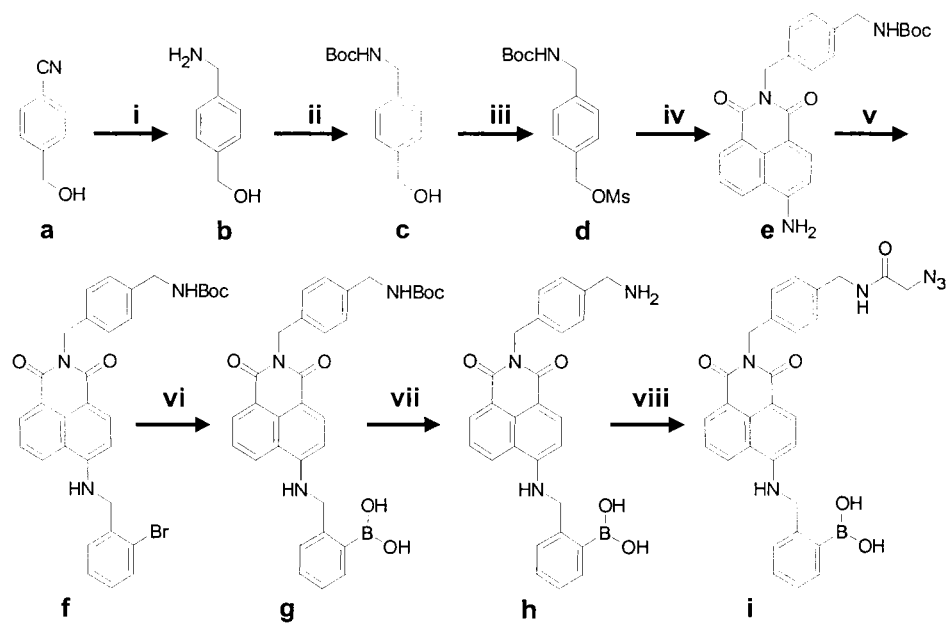
FIG. 27 illustrates a scheme for the synthesis of 4-(2-dihydroxylboryl-benzyl)amino-N-(4'-azidoacetyl-aminomethylbenzyl)-1,8-naphthalimide. Steps: (i), LiAlH$_4$, tetrahydrofuran reflux, 98%; (ii), di-t-butyl dicarbonate, triethylamine, tetrahydrofuran, 94%; iii), MsCl, triethylamine, tetrahydrofuran, 96%; (iv), sodium methoxide, 4-amino-napthalimide, dimethylformamide, 90%; (v), NaH, 2-bromo-benzyl bromide, dimethylformamide, 40%; (vi), Bis(neopentyl glycolatodiboron, PdCl$_2$ (dppf), potassium acetate, dimethyl sulfoxide, 45%; (vii) trifluoroacetic acid, methylene dichloride; and (viii) azidoacetic acid, EDCl, HOBt, dimethylformamide, 37%.
Figure 28:
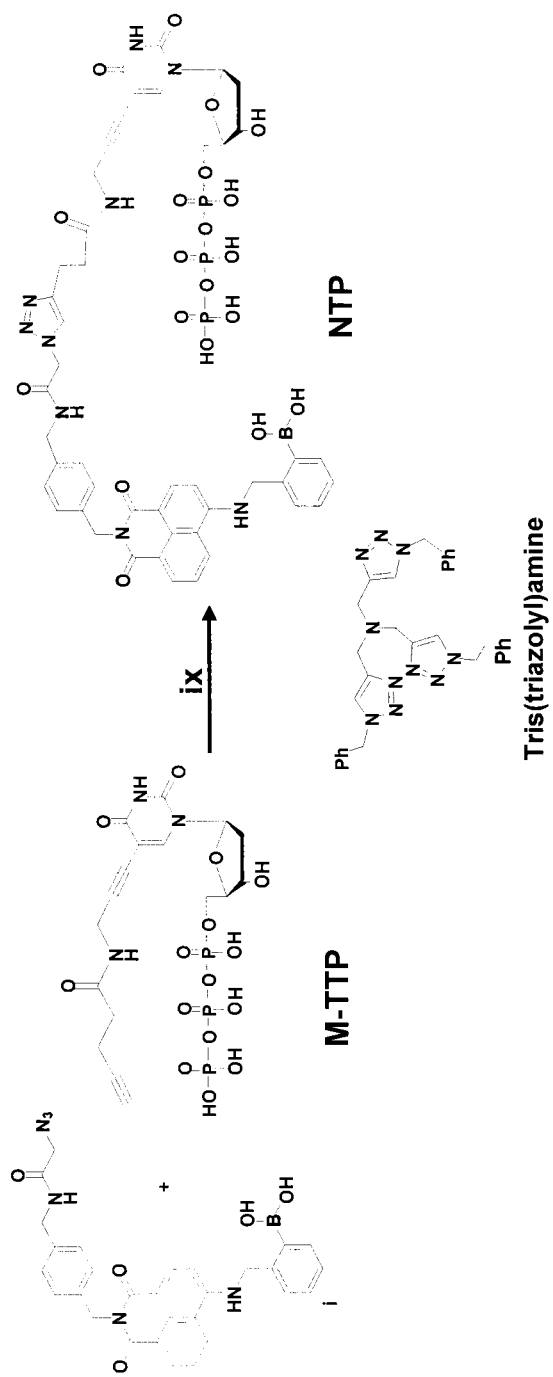
FIG. 28 illustrates a scheme for the linking of 4-(2-dihydroxylboryl-benzyl)amino-N-(4'-azidoacetyl-aminomethylbenzyl)-1,8-naphthalimide and M-TTP to generate N-TTP. Step (ix): 0.1 equiv CuBr, 0.1 equiv tris(triazolyl)amine, ethanol/water (1:1).

The long-wavelength fluorescent N-TTP resembles B-TTP with the exception that group $R_5$ is napthalimide-based boronic acid (as shown in FIG. 28). Synthesis of the boronic acid moiety starts from NaBH$_4$ reduction of 4-(hydroxymethyl)benzonitrile into 4-aminomethylbenzyl alcohol (b of FIG. 27) followed by Boc- protection of the —NH$_2$ group and mesylation of the —OH group. Alkylation of 4-amino-1,8-naphthalimide with (4-Boc-aminomethylbenzyl)methansulfonate and 2-bromobenzyl bromide sequentially yields the aromatic bromide (f), which is subjected to Pd catalyzed borylation in a subsequent step. The obtained fluorescent boronic acid is deprotected of its Boc- group by using TFA and then coupled with azidoacetic acid by using EDCl and HOBt.

Tethering of the synthesized naphthalimide-based boronic acid with M-TTP was accomplished using the click chemistry as described in the synthesis of B-TTP. In one kind of click chemistry, Cu(I)-catalyzed alkyne-azide cycloaddition developed by Sharpless (Kolb et al. *Angew. Chem.*, Int. Ed. 2001, 40: 2004; Wang, et al.; *J. Am. Chem. Soc.*, 2003, 125: 3192-3193) has been proven to be a very efficient way of linking a large fluorophore group to biomolecules. In the coupling step as shown in Scheme 2, FIG. 28, tris(triazolyl)amine was added as a Cu ligand to accelerate the reaction rate and also to protect the boronic acid unit from metal-catalyzed degradation.

Figure 21:
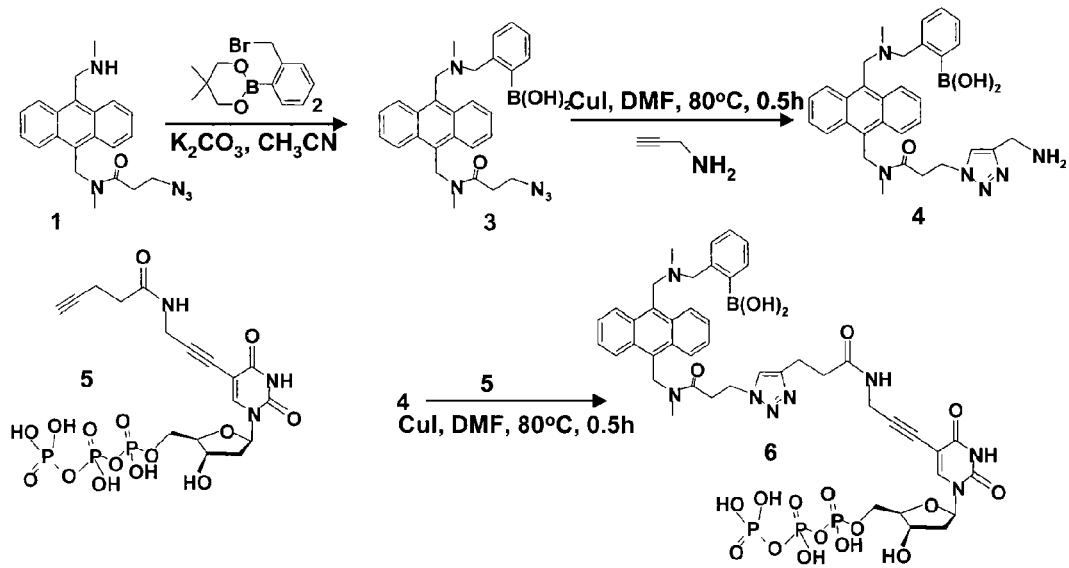
FIG. 21 illustrates Scheme 5 for the synthesis of an anthracene-boronic acid (4) and anthracene-boronic acid-labeled deoxyuridine-5'-triphosphate (6).

A specific example of the preparation of one such fluorescent compound is shown in Schematic 5 shown in FIG. 21. Anthracene boronic acid compounds such as (3) shown in FIG. 21 change fluorescent properties upon sugar binding. To determine whether conjugates of such boronic acid fluorescent reporters with amines or deoxyuridine-5'-triphosphate would still retain their ability to change fluorescence properties upon sugar binding, we synthesized compounds (4) and (6) (Scheme 5, FIG. 21). Both compounds (4) and (6) changed fluorescent properties upon sugar binding, as shown in FIGS. 22 and 23. Such results confirmed the suitability of similar fluorescent boronic acids for incorporation into DNA for the development of boronic acid-modified DNA aptamer, which would change fluorescent properties upon sugar binding.

Targeting of Glycosylated Prostate Specific Antigen (PSA)

PSA is a glycoprotein secreted by prostate epithelial cells, and belongs to the family of serine proteases. It has a molecular weight of about 28.4 kDa with 237 amino acid residues and five interchain disulphide bonds. PSA contains approximately 8% carbohydrate in the form of an N-linked oligosaccharide side chain attached at residue Asn 45. It is a well recognized biomarker for prostate carcinoma.

Initial screening for prostate cancer is typically based on the level of PSA, with 4 ng/mL being the threshold level for recommending further testing. However, this PSA test has a high false negative and high false positive rate. One reason for this is that simple inflammation and benign tumors can also cause elevated levels of PSA. It has been shown that PSA of non-cancerous origin has different glycosylation patterns compared with patterns of glycosylation of PSA derived from cancer cell lines (LNCaP), and that from prostate cancer patient's serum and tissues.

The embodiments of the present disclosure, therefore, encompass boronic acid modified aptamers that can both recognize PSA and differentiate its various glycosylation patterns, thereby providing an accurate and reliable method of prostate cancer diagnosis. Aptamers selected as having a bias for a glycosylated species of PSA and selected by the methods of the present disclosure in those having the sequences SEQ ID NOs.: 59-68, as shown in FIGS. 26A-26F. The degree of selectivity of the boronic acid-containing aptamers, as reflected in the aptamer's $K_d$, avoids cross-reactivity and false positive problems.

The normal PSA serum range is between about 2.5-25 ng/mL, and the commonly accepted threshold for recommending further evaluation is 4 ng/mL. Given the five-fold difference between the threshold and the upper limit of the normal PSA range, a five-fold selectivity should be the lower limit for an aptamer to give useful results. In addition, PSA level can rise to over 50 ng/mL in prostate cancer patients (an extremely abnormal high number), which increases the selectivity need by another 2-fold (raising this need to 10-fold). For added confidence, an additional five-fold over the lower limit, which would give a 50-fold selectivity, may be used. Therefore, a 50-fold selectivity of the aptamer for two different glycoforms of PSA would be sufficient to give a low percentage of false negative due to cross reactivity. For practical considerations, a 50-fold selectivity that takes into consideration having 50 ng/mL of entirely non-target PSA glycoforms as the upper limit, would be desirable.

One aspect of the present disclosure, therefore, encompasses a nucleotide monomer having the formula shown in FIG. 1A, where $R_1$ is a monophosphate ester, a diphosphate ester, or a triphosphate ester; $R_2$ and $R_3$ are individually H—, or OH—; $R_4$ is a base selected from the group consisting of adenine, cytosine, guanine, thymine, hypoxanthine, and uracil; and $R_5$ is a boronic acid wherein $R_5$ is a boronic acid other than unsubstituted phenylboronic acid having the structure:

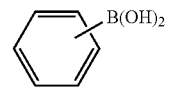

In one embodiment of the disclosure, the nucleotide monomer may further comprise a tether linking $R_4$ and $R_5$.

In one embodiment of this aspect of the disclosure, $R_4$ is thymine, $R_2$ is OH—, and $R_3$ is H—.

In other embodiments of the disclosure, $R_5$ is a boronic acid that may be selected from the group consisting of, but not limited to, a phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

In one embodiment of the disclosure, the nucleotide monomer has the formula shown in FIG. 3 (compound (12)).

In yet other embodiments of the disclosure, $R_5$ may be a fluorescent boronic acid that may be one of, but not limited to, the structures illustrated in FIG. 24.

Another aspect of the present disclosure encompasses an aptamer having selective affinity for a glycosylated polypeptide, the aptamers comprising at least one nucleotide monomer having the formula shown in FIG. 1A, where $R_1$ is a monophosphate ester; $R_2$ and $R_3$ are individually H—, or OH—; $R_4$ is a base selected from the group consisting of adenine, cytosine, guanine, thymine, hypoxanthine, and uracil; $R_5$ is a boronic acid, and the aptamer has selective affinity for a target polypeptide and a glycosylation chain thereon.

In embodiments of this aspect of the disclosure, the aptamer may selectively bind to a glycosylation site of the target polypeptide or protein. In some embodiments of the disclosure, the glycosylation site comprises a region of a glycan chain and a region of the polypeptide.

In the embodiments of this aspect of the disclosure, the aptamer may have enhanced selective affinity for a glycosylated site of the target polypeptide compared to a second aptamer that has an identical nucleotide sequence to that of the first aptamer, but does not have a boronic acid group thereon.

In embodiments the aptamers of the disclosure, the nucleotide monomer may further comprise a tether linking $R_4$ and $R_5$.

In one embodiment of the disclosure, $R_4$ is thymine, $R_2$ is OH, and $R_3$ is H.

In the embodiments of the aptamers of this aspect of the disclosure, $R_5$ is a boronic acid that may be selected from the group consisting of: a phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

In one embodiment of the aptamers of the disclosure, the nucleotide monomer may have the formula shown in FIG. 3 (compound (12)).

In other embodiments of the aptamers of the disclosure, the boronic acid may be a fluorescent boronic acid, where the fluorescent boronic acid may be selected from the group consisting of, but not limited to, the structures illustrated in FIG. 24.

Yet another aspect of the present disclosure encompasses methods of isolating an aptamer, where the aptamer can selectively bind to a glycosylation site of a target polypeptide or protein, comprising: from a population of randomized oligonucleotides, wherein each oligonucleotide includes at least one nucleotide having a boronic acid label linked to a base thereon, selecting a first subpopulation of aptamers binding to a target glyocsylated polypeptide or protein; amplifying the first subpopulation of aptamers without using boronic acid-modified TTP, and selecting from the amplification products thereof a second subpopulation of aptamers not binding to a glycosylated species of the target polypeptide or protein; and amplifying the second subpopulation of aptamers using boronic acid-modified TTP, thereby providing a population of boronic acid-modified aptamers capable of selectively binding to a glycosylation site of a target polypeptide or protein.

In embodiments of the methods of this aspect of the disclosure, the method may further comprise a counter-selection step, wherein the counter-selection step comprises identifying aptamers capable of selectively binding to a solid support not having a target polypeptide bound thereto, a deglycosylated target polypeptide or protein, or a cross-reacting non-targeted polypeptide or proteins.

In one embodiment of this aspect of the disclosure, step (a) may further comprise: (a) amplifying a library of randomized oligonucleotides, where each oligonucleotide includes at least one nucleotide having a boronic acid label linked to a base thereon; (b) contacting the library with a glycosylated target polypeptide or protein under conditions whereby a subpopulation of the library of aptamers selectively binds to a glycosylation site of the target polypeptide; (c) isolating target polypeptides or proteins having the subpopulation of aptamers bound thereto, and eluting the subpopulation of aptamers from the target polypeptide; (d) amplifying the eluted subpopulation of aptamers; and (e) repeating steps (b)-(d), thereby isolating a population of aptamers from the amplified library from step (a), wherein the aptamers are capable of binding a glycosylation site of the target polypeptide, and where the method may further comprise repeating (b)-(e) where the target polypeptide is not glycosylated, thereby selectively removing from the population of aptamers those aptamers binding only to the polypeptide and not to the glycosylation site thereof.

In yet another embodiment of this aspect of the disclosure, the method may further comprise: (i) inserting a population of aptamers isolated in step (e) into a vector, and isolating clones thereof; (ii) identifying a plurality of aptamer clones, wherein the aptamers have sequences differing from each other; (iii) determining the dissociation constants of the individual aptamers and the target glycosylated polypeptide; (iv) comparing the dissociation constants of the aptamer sequences to the dissociation constants of a control aptamer not having a boronic acid thereon; and (v) selecting one or more aptamers having a lower dissociation constant than the control, whereby the selected aptamers have enhanced selective affinity for a glycosylated site of the target polypeptide compared to control aptamers having an identical nucleotide sequence to that of the selected aptamers but not having a boronic acid group thereon.

In one embodiment of the disclosure, the target polypeptide can be immobilized on a solid support.

In the embodiments of this aspect of the disclosure, the at least one nucleotide may have a boronic acid label modified base thereon having the formula shown in FIG. 1A, where $R_1$ is a monobasic ester; $R_2$ and $R_3$ are individually H, or OH; wherein $R_4$ is a base selected from the group consisting of: adenine, cytosine, guanine, thymine, hypoxanthine and uracil; $R_5$ is a boronic acid, and the aptamer can selectively bind a glycosylated species of a target polypeptide.

In one embodiment of the disclosure, $R_1$ is $-PO_4-$, $R_4$ is thymine, $R_2$ is OH, and $R_3$ is H, and $R_5$ is a boronic acid.

In embodiments of the disclosure, the at least one nucleotide may have a boronic acid label modified base thereon further comprises a tether linking $R_4$ and $R_5$.

In other embodiments of the disclosure, $R_5$ may be a boronic acid such as, but not limited to, a phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

In one embodiment, the at least one nucleotide having a boronic acid label modified base thereon has the formula shown in FIG. 3 (compound (12)).

In yet other embodiments of this aspect of the disclosure, the at least one nucleotide may have a boronic acid label modified base thereon comprising a fluorescent boronic acid selected from, but not limited to, the group illustrated in FIG. 24.

Still yet another aspect of the present disclosure encompasses methods of detecting a glycosylated species of a target polypeptide or protein, comprising: providing a target polypeptide; contacting the target polypeptide or protein with a first aptamer comprising at least one nucleotide having a boronic acid label linked to a base thereon, wherein the first aptamer has enhanced selective affinity for a glycosylated site of the target polypeptide compared to a second aptamer having an identical nucleotide sequence to that of the first aptamer but not having a boronic acid group thereon; providing conditions suitable for selective binding of the first aptamer to the glycosylated site of the target polypeptide; and detecting a population of bound first aptamers, thereby indicating the presence of the glycosylation site of the target polypeptide.

In embodiments of this aspect of the disclosure, the first aptamer may comprise at least one nucleotide monomer having the formula shown in FIG. 1A, where $R_1$ is a monophosphate ester; $R_2$ and $R_3$ are individually H, or OH; $R_4$ is a base selected from the group consisting of: adenine, cytosine, guanine, thymine, hypoxanthine, and uracil; $R_5$ is a boronic acid, and where the aptamer has selective affinity for a target polypeptide and a glycosylation chain thereon.

In these embodiments of the disclosure, the glycosylation site of the target polypeptide may comprise a region of a glycosylation chain and a region of the polypeptide.

In embodiments of the methods of this aspect of the disclosure, the nucleotide monomer may further comprise a tether linking $R_4$ and $R_5$.

In one embodiment, $R_4$ is thymine, $R_2$ is OH, and $R_3$ is H. In other embodiments, $R_5$ is a boronic acid such as, but not limited to, a phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

In one embodiment encompassed by this aspect of the disclosure, the nucleotide monomer may have the formula shown in FIG. 3 (compound (12)).

In other embodiments of this aspect of the disclosure, the boronic acid may be a fluorescent boronic acid, and the fluorescent boronic acid may be one of, but not limited to, the structures illustrated in FIG. 24.

In yet other embodiments of the disclosure, the target polypeptide or protein may be selected from the group consisting of: an isolated polypeptide or protein, or a fragment thereof, a polypeptide in or on a cell, a tissue of an animal or plant, or a cultured cell.

In certain embodiments, the target polypeptide or protein can be Prostate Serum Antigen (PSA), or fibrinogen. In one embodiment, the first aptamer may selectively bind to high pI PSA, low pI PSA, or both high and low pI PSA.

In these embodiments of the method of this aspect of the disclosure, the first aptamer may have, but is not limited to, a nucleotide sequence selected from SEQ ID NOS.: 59-68.

In one embodiment of the disclosure, the first aptamer can selectively bind to a glycosylated species of fibrinogen, and may have, but is not limited to, a sequence selected from SEQ ID NOs.: 13-58.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

Example 1

Synthesis of the Boronic Acid-labeled Thymidine Triphosphate (B-TTP)
Materials: For all reactions analytical grade solvents were used. Anhydrous solvents were used for all moisture-sensitive reactions. NMR data was collected on a Varian Unity 300 MHz or a Bruker 400 MHz spectrophotometer. The chemical shifts are relative to trimethylsilane as an internal standard for $^1$H, the deuterated solvent used for $^{13}$C, and 85% $H_3PO_4$ as an external reference for $^{31}$P. Mass spectra were recorded on a Waters Micromass LC-Q-TOF microspectrometer. The structures of the intermediates and final products, and schematics of their syntheses are shown in FIGS. 1-3.
(a) 8-Bromo-2-methylquinoline (2)

To the solution of 2-bromoaniline (5.0 g, 29.1 mmol) in 6 N hydrochloric acid (15 mL) under reflux was added crotonaldehyde (2.2409 g, 32.0 mmol) drop wise. After refluxing for 8 h, the reaction mixture was cooled down and washed with 20 mL of ether, followed by the addition of zinc chloride (3.95 g). The reaction mixture was stirred for 30 min at room temperature and an additional 15 min at 0° C. to yield a yellow precipitate. The solid was collected and washed with 3N cold hydrochloric acid, and then suspended in 2-propanol (20 mL) and stirred for 5 min at room temperature. The solid was filtered and washed with 2-propanol until the washing became colorless, and then washed with 20 mL of ether and dried with air. The solid was suspended in 15 mL of cold water followed by the addition of 5 mL of concentrated ammonium hydroxide. The mixture was vigorously shaken and then extracted with ether (3×20 mL). After drying over magnesium sulfate and concentration, a dark solid product was obtained, which was purified by chromatography (ethyl acetate/hexanes 10:90) to give a white solid product. (3.62 g, 56%) $^1$H NMR (400 MHz, CDCl$_3$) δ8.02 (2H, t, J=8.4 Hz), 7.73 (1H, d, J=8 Hz), 7.33 (2H, t, J=8), 2.82 (3H, s); $^{13}$C NMR (75 MHz, CDCl$_3$) δ160.2, 144.7, 136.4, 132.8, 127.6, 127.3, 125.9, 124.0, 122.7, 25.6; EIMS, m/z 221/223 M/M+2; Analysis calculated for $C_{10}H_8BrN$: C, 54.08; H, 3.63; N, 6.31. Found: C, 54.25; H, 3.41; N, 5.89.
(b) 8-Bromo-2-bromomethylquinoline (3)

To a solution of (2) (2.5477 g, 11.47 mmol) in carbon tetrachloride (40 mL) was added n-bromosuccinimide (NBS) (2.2461 g, 12.62 mmol) and 20 mg of azobisisobutyronitrile (AIBN). The mixture was refluxed overnight under regular light, and then filtered to remove the solid. Evaporation of the solvent gave a yellow solid product, which was purified by chromatography (hexanes/dichloromethane 80:20) to yield a white solid (1.33 g, 39%). $^1$H NMR (400 MHz, CDCl$_3$) δ8.16 (1H, d, J=8.4 Hz), 8.05 (1H, d, J=7.2 Hz), 7.78 (1H, d, J=7.6 Hz), 7.65 (1H, d, J=8.4 Hz), 7.41 (1H, t, J=7.6 Hz), 4.78 (3H, s); $^{13}$C NMR (100 MHz, CDCl$_3$) δ158.3, 144.7, 138.0, 133.9, 128.9, 127.7, 127.6, 125.1, 122.4, 34.6; EIMS, m/z 299/300/301 (M/M+1/M+2); Analysis calculated for $C_{10}H_7Br_2N$: C, 39.91; H, 2.34; N, 4.65. Found: C, 40.13; H, 2.281; N, 4.34.
(c) (8-Bromo-quinolin-2-ylmethyl)-methylamine (4)

To a solution of (3) (1 g, 3.32 mmol) in tetrahydrofuran (5 mL) was added methylamine (10.5 mL, 40% aqueous solution). The solution was stirred for 30 min and then extracted with EtOAc (30 mL). The organic phase was washed with deionized water (2×20 mL), dried over anhydrous magnesium sulfate and concentrated to give a red oily product, which was purified by column chromatography (methanol/dichloromethane 1:99) to yield a yellow solid (0.8 g, 96%). $^1$H NMR (400 MHz CDCl$_3$) δ8.09 (1H, d, J=8.4 Hz), 8.02 (1H, d, J=7.2 Hz), 7.77 (1H, d, J=8 Hz), 7.49 (1H, d, J=8.4 Hz), 7.36 (1H, t, J=8.0 Hz), 4.12 (2H, s), 2.58 (3H, s); FABMS, m/z 251/253 (M+H/M+2+H); Anal. Calculated for $C_{11}H_{11}BrN_2$: C, 52.61; H, 4.42; N, 11.16. Found: C, 52.17; H, 4.46; N, 11.10.
(d) (8-Bromo-quinolin-2-ylmethyl)-methylcarbamic acid tert-butyl ester (5)

To a solution of (4) (0.7501 g, 2.99 mmol) in methanol was added (Boc)$_2$O (1.4992 g, 6.87 mmol) and triethylamine (2.1 mL, 14.9 mmol). The mixture was stirred at room temperature for 2 h, and then concentrated in vacuo to remove all of the solvent. The residue was dissolved in dichloromethane (20 mL) and then washed with deionized water (2×10 mL) and brine (10 mL). The organic solution was dried over magnesium sulfate and concentrated to give yellow oil. Purification by chromatography (hexanes/EtOAc 10:90) yielded a light yellow oily product. $^1$H NMR (400 MHz CDCl$_3$) δ8.16 (1H, t, J=8.4 Hz), 8.06 (1H, d, J=6.9 Hz), 7.80 (1H, d, J=7.8 Hz), 7.41 (2H, m), 4.81 (2H, s), 3.03 (3H, d, J=11.7 Hz), 1.4-1.6 (9H); $^{13}$C NMR (100 MHz, CDCl$_3$) δ160.0, 144.9, 137.5, 133.4, 128.7, 127.7, 126.9, 124.9, 120.7, 119.8, 80.1, 55.5, 35.2, 28.7; ESIMS, m/z 351/353 (M/(M+2), 100); Analysis calculated for $C_{16}H_{19}BrN_2O_2$: C, 54.71; H, 5.45; N, 7.98. Found: C, 54.97; H, 5.62; N, 7.75.

(e) 2-[(tert-butoxycarbonyl-methyl-amino)-methyl]-quinoline-8-boronic acid (6)

To a flask charged with (5) (0.4440 g, 1.26 mmol), bis(neopentyl glycolato) diboron (0.3427 g, 1.52 mmol), Pd(dppf)$_2$Cl$_2$ (0.0310 g, 0.038 mmol) and potassium acetate (0.3722 g, 3.79 mmol) in a nitrogen atmosphere was added anhydrous dimethylsolfoxide (10 mL). The mixture was stirred at 80° C. overnight. After cooling down, the reaction mixture was poured into dichloromethane (20 mL) and washed with deionized water (4×30 mL). The organic solution was dried over magnesium sulfate and concentrated to give dark oil. Purification by column chromatography (methanol/dichloromethane, 1:99) yielded a yellow oily product (0.3313 g, 82%). $^1$H NMR (400 MHz CDCl$_3$) δ8.45 (1H, d, J=5.4 Hz), 8.14 (1H, d, J=6.6 Hz), 7.97 (1H, d, J=8.1 Hz), 7.623 (1H, t, J=7.5 Hz), 7.49 (1H, d, J=8.4 Hz), 4.80 (2H, d, J=6.0 Hz), 3.09 (3H, d, J=4.2 Hz), 1.3-1.5 (9H); $^{13}$C NMR (100 MHz, CDCl$_3$) δ157.3, 156.8, 156.2, 150.3, 139.4, 137.4, 129.7, 127.2, 126.6, 119.1, 118.9, 80.5, 74.7, 34.7, 27.4, 23.9; ESIMS, m/z 315, M−1.

(f) Compound (7)

To a solution of (6) (0.226 g, 0.72 mmol) in dichloromethane (20 mL) was added trifluoroacetic acid (5 mL). The solution was stirred for 1 h, and then concentrated in vacuo to give yellow oil, which was then dissolved in dry tetrahydrofuran (10 mL). To this mixture was added azido acetic acid (79 mg, 0.79 mmol), N,N'-carbonyldiimidazole (CDI) (174 mg, 1.07 mmol), and i-PrNEt (0.25 mL, 1.43 mmol) at 0° C. The mixture was stirred overnight at r.t. and then concentrated to almost dryness. Purification by silica gel column (dichloromethane/methanol, 100:1) yielded a yellow solid (0.160 g, 68%). $^1$H NMR (400 MHz CDCl$_3$) δ8.45 (1H, d, J=5.4 Hz), 8.14 (1H, d, J=6.6 Hz), 7.97 (1H, d, J=8.1 Hz), 7.623 (1H, t, J=7.5 Hz), 7.49 (1H, d, J=8.4 Hz), 4.80 (2H, d, J=6.0 Hz), 4.30 (2H, d, J=5.5 Hz), 3.09 (3H, d). ESIMS, m/z 300, M+1.

(g) 5-[3-(Trifluoroacetamido)-propynyl]-2'-deoxyuridine (9)

5-Iodo-2'-deoxyuridine (8) (0.35 g, 1.0 mmol) was dissolved in degassed anhydrous dimethylformamide (10 mL). Copper (I) iodide (0.038 g, 0.2 mmol) was added and the reaction mixture was stirred under nitrogen in the dark by wrapping the reaction flask with aluminum foil for 30 min. Triethylamine (0.3 mL, 2.0 mmol) was added to the reaction mixture, followed by N-propynyltrifluoroacetamide (0.45 g, 2.97 mmol) and tetrakis(triphenylphosphine) palladium (0) (0.11 g, 0.10 mmol). The reaction mixture was stirred overnight with an aluminum foil wrap at room temperature. Then solvent was removed and the residue was purified with a silica gel column (methanol/dichloromethane 1:20) to give a light yellow solid (0.25 g, 67%). $^1$H NMR (300 MHz, CD$_3$OD) δ8.4 (1H, s), 6.22 (1H, t), 4.39 (1H, m), 4.26 (2H, s), 3.82 (1H, m), 3.74 (2H, m), 2.38-2.20 (2H, m). ESIMS (m/z): 378 (M+1).

(h) Compound (10)

To compound (9) (0.25 g, 0.66 mmol) dissolved in methanol was added ammonium hydroxide. The mixture was stirred overnight followed by solvent removal. The residue was dried under vacuum and then dissolved in dimethylformamide. Pentynoic acid (68 mg, 0.69 mmol) and benzotriazol-1-yl-oxytripyrrolidinophosphonium hexafluorophosphate (PyBop) (0.99 mmol) were added under ice-bath cooling. The mixture was stirred overnight at room temperature. Then solvent was evaporated and the residue was purified by silica gel chromatography (methanol/dichloromethane 1:15) to give the product (quantity and yield) (155 mg, 65%). $^1$H NMR (100 MHz CD$_3$OD): δ8.29 (1H, s), 6.22 (1H, t), 4.39 (1H, m), 4.14 (2H, s), 3.90 (1H, m), 3.74 (2H, m), 2.41 (4H, m), 2.26 (3H, m). $^{13}$C NMR (100 MHz, CD$_3$OD) δ170.8, 162.0, 148.2, 142.7, 97.2, 87.2, 86.5, 84.3, 80.9, 72.5, 69.4, 67.7, 59.9, 39.0, 33.1, 27.7, 12.8. ESIMS (m/z): 362 (M+1).

(i) Compound (11)

Compound (10) (0.15 g, 0.4 mmol) was dried in vacuo over phosphorous pentoxide overnight and then dissolved in anhydrous trimethylphosphate (0.6 mL) under nitrogen. Proton sponge (also dried overnight over phosphorous pentoxide) (0.102 g, 0.48 mmol) was added to the solution in one portion. Then the reaction mixture was cooled in an ice-bath and POCl$_3$ was added drop wise via a syringe with stirring. The reaction mixture was stirred on ice for 2 h and then a mixture of 0.98 g of bis-tri-n-butylammonium pyrophosphate (dissolved in dimethylformamide 1.6 mL) and 0.6 mL tri-n-butylamine was added in one portion. The mixture was stirred at room temperature for 10 min and then triethylammonium bicarbonate solution (0.1 M, pH 8, 10 mL) was added. The reaction mixture was stirred at room temperature for an additional hour and purified with a DEAE-Sephadex A-25 column using a linear gradient of ammonium bicarbonate (0-0.6 M) followed by freeze drying to give the final product as a white powder (84 mg, 35%). $^1$H NMR (100 MHz, D$_2$O): δ8.21 (1H, s), 6.33 (1H, t), 4.68 (1H, m), 4.26 (5H, m), 2.57 (4H, m), 2.45 (3H, m). $^{13}$C NMR (100 MHz, D$_2$O) δ174.1, 164.2, 150.1, 144.5, 98.7, 89.4, 85.5, 85.2, 83.0, 73.1, 70.1, 69.7, 65.0, 38.5, 33.9, 29.2, 14.0; $^{31}$P NMR (161 MHz, D$_2$O): δ−10.04 (γP, d), −11.30 (αP, d), −22.96 (βP, t). ESIMS (m/z): 601 (M), 521 (M−80).

(j) Compound (12) (B-TTP)

The azide compound (7) (0.014 g, 0.046 mmol) and triphosphate compound (11) (0.009 g, 0.015 mmol) were suspended in 150 μl of a mixture of ethanol/water/t-butyl alcohol (3:2:5). To this mixture were added 5 μL of 1.12 M sodium ascorbate aqueous solution and 5 μL of 0.54 M copper sulfate aqueous solution. The mixture was stirred at room temperature overnight and then filtered to remove the unreacted azide compound. The filtrate was purified by a DEAE-Sephadex A-25 column. Fractions were collected by monitoring the UV absorbance at 289 nm. The combined fractions were lyophilize to yield a white powder product (3 mg, 20%). $^1$H NMR (100 MHz CD$_3$OD): δ8.52 (1H, m), 8.11 (1H, m), 7.88 (1H, m), 7.68 (1H, s), 7.54 (2H, m), 7.15 (1H, m), 5.94 (1H, dt), 5.60 (2H, d), 5.01 (2H, d), 4.43 (1H, m), 4.06 (3H, m), 3.99 (2H, m), 3.23 (2H, s), 2.98 (3H, d), 2.54 (2H, d), 2.18 (2H, m). 1.69 (2H, m), 1.21 (2H, m). $^{31}$P NMR (161 MHz, D$_2$O): δ−9.65 (γP, d), −10.76 (αP, d), −22.36 (βP, t); ESIMS, m/z 864/784, M−2H$_2$O/M−2H$_2$O−80.

The stability of the boronic acid-modified-TTP has been studied at 94° C. for 2 hr. No degradation was observed based on NMR and MS.

(k) N-[2-(3,4-Dihydroxy-phenyl)-ethyl]acrylamide (13)

To a suspension of dopamine hydrochloride (3 g, 16 mmol) in dichloromethane (35 mL) was added triethylamine (6.7 mL). The mixture was stirred for 1 h then trimethylchlorosilane was added. After 4 h, additional triethylamine (2.5 mL) was added followed by acryloyl chloride in a dropwise fashion with an ice-bath cooling. After stirring the reaction for 12 h, the white precipitate was filtered, collected, and re-dissolved in 30 mL dichloromethane followed by the addition of 10% tetrafluoroacetic acid/dichloromethane. The reaction mixture was stirred over night at room temperature. The white precipitate product was filtered and collected (2.01 g, 64%). $^1$H NMR (100 MHz CDCl$_3$) 6.69 (2H, m), 6.53 (1H, dd), 6.20

(1H, d), 6.18 (1H, d), 5.62 (1H, t, J=6.0 Hz), 3.4 (2H, m), 2.66 (2H, t, J=7.8 Hz). $^{13}$C NMR (100 MHz, CDCl$_3$) δ166.71, 144.87, 143.41, 130.71, 130.57, 125.10, 119.61, 115.10, 114.98, 41.00, 34.47.

Example 2

$^{32}$P Labeling of the Primers

A mixture of 10 μL of primer DNA (100 μM), 2.0 μL of ×10 T4 polynucleotide kinase buffer, 3.0 μL of water, 3.0 μL of T4 polynucleotide kinase (10,000 units/mL, Biolabs. Inc.) and 2.0 μL of γ-$^{32}$P-ATP (from Perkin/Elmer) was incubated for 1 hr at 37° C. followed by heating in a water-bath at 100° C. for 5 min to denature the T4 polynucleotide kinase. The phosphorylated DNA was precipitated with 2.2 μL of 3 M sodium chloride solution and 66.6 μL of ethanol. The mixture was chilled at −20° C. for 15 min and centrifuged at 14,000 rpm for 15 min. The supernatant was discarded and the pellet was re-dissolved in 8 μL of water (to obtain approximately 100 μM DNA solution, assuming an 80% recovery yield), and stored at −20° C.

Example 3

DNA Primer Extension and Time-course Study of Incorporation of B-TTP (12) into DNA Primer Extensions Primer extensions were performed with 5'-$^{32}$P-labeled Primer 21-nt (SEQ ID NO.: 1, shown in FIG. 26) (5 μM), and the oligonucleotide Template 1 (SEQ ID NO.: 4) (5 μM), Klenow (0.04 units/μL); and dNTPs (0.4 mM each). The reaction mixture was incubated at 37° C. Aliquots (5 μL) of the solution were taken at 0.5 min, 2 min, 5 min, 15 min and 60 min and were put into an ice-bath to stop the reaction following the addition of 5 μL of denaturing dye solution (8 M urea) into each aliquot. These samples were analyzed later by electrophoresis and autoradiography, the results of which are illustrated in FIG. 5.

Figure 5:
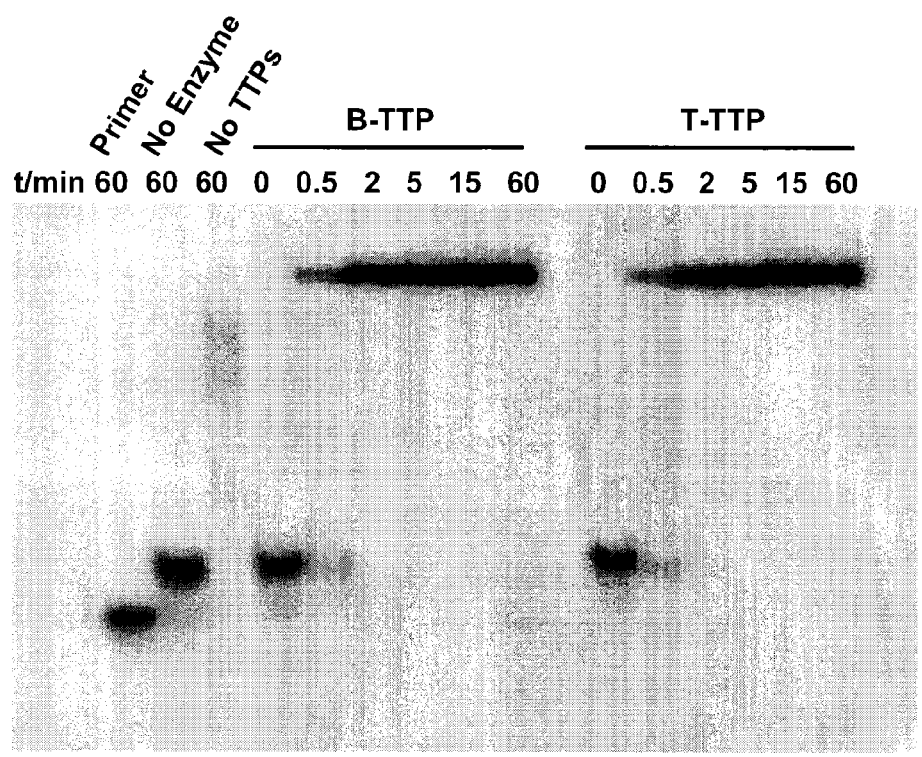
FIG. 5 illustrates the result of a time-dependent primer extension experiment using B-TTP and TTP. Electrophoresis was conducted on 19% acrylamide gel.
Figure 6:
FIG. 6 illustrates the results of primer extension using B-TTP and analyzed on a 15% acrylamide gel. Lane loadings were as follows: Lane 1 (from left): M-TTP-DNA, Lane 2: co-spot of M-TTP-DNA and TTP-DNA; Lane 3: TTP-DNA, Lane 4: co-spot of B-TTP-DNA, and TTP-DNA, Lane 5 B-TTP-DNA, lane 6: primer.

As shown in FIG. 5, there was no noticeable difference in the rate of incorporation of natural TTP and B-TTP. For example, at 0.5 min, neither the B-TTP nor the natural TTP was incorporated significantly. From time 0 to 15 min, there was time-dependent incorporation in both cases. At 15 min, both reactions reached maximal incorporation. Control reactions with only the primer, without enzyme, and without added TTP or labeled TTP showed no full-length DNA formation. The smear in the third lane (FIG. 5) without TTP was from mismatch pairing and incomplete reaction. All these indicate that the boronic acid labeled base, B-TTP (12), was recognized by the Klenow fragment at approximately the same level as natural TTP. B-TTP DNA and TTP-DNA were not well-separated when using 19% acrylamide gel (FIG. 5), but were well resolved when using 15% acrylamide gel, as shown in FIG. 6.

Example 4

Preparation of the Polyacrylamide Gel Containing Catechol

19% acrylamide gels modified with 1% catechol:urea (12.6 g), N-[2-(3,4-dihydroxy-phenyl)-ethyl]-acrylamide (0.16 g), a 40% acrylamide solution (24 mL), 5×TBE (Tris-borate-EDTA made from 108 g Tris base, 55 g boric acid, 9.3 g Na$_4$EDTA in 1 L of water) (6 mL) and water (6 mL) were mixed and heated in a microwave for 30 seconds. After cooling, 20 μL of TEMED (N,N,N-tetramethylethylenediamine) and 150 μL of APS (ammonium persulfate) were added before loading this solution into a gel cast.

Example 5

Primer Extension Using Boronic Acid-labeled DNA as Templates

Primer 1 (SEQ ID NO.: 2) and oligonucleotide Template 1 (SEQ ID NO.: 4) (5 μM), Klenow (0.04 units/μL), UP (0.4 mM), B-TTP (0.4 mM) or M-TTP (0.4 mM), and three other dNTPs (0.4 mM each) were incubated at 37° C. for an hour. The prepared DNAs were purified by membrane filtration for 15 min at 14,000 rpm, using Microcon centrifugal filter YM-3 from Millipore Corporation, to remove the labeled and non-labeled dNTPs and other low molecular weigh molecules. 5'-$^{32}$P-labeled Primer 2 (SEQ ID NO.: 3) was then added to the DNAs prepared using Primer 1, individually, and the mixtures were heated for 2 min at 95° C. The mixtures were cooled to room temperature over 10 min. The second run of the polymerizations on the labeled and non-labeled DNA templates was performed under the conditions of four dNTPs (0.4 mM each) and Klenow (0.04 units/μL) at 37° C. for an hour. The resulted samples were analyzed by electrophoresis and autoradiography.

Figure 4:
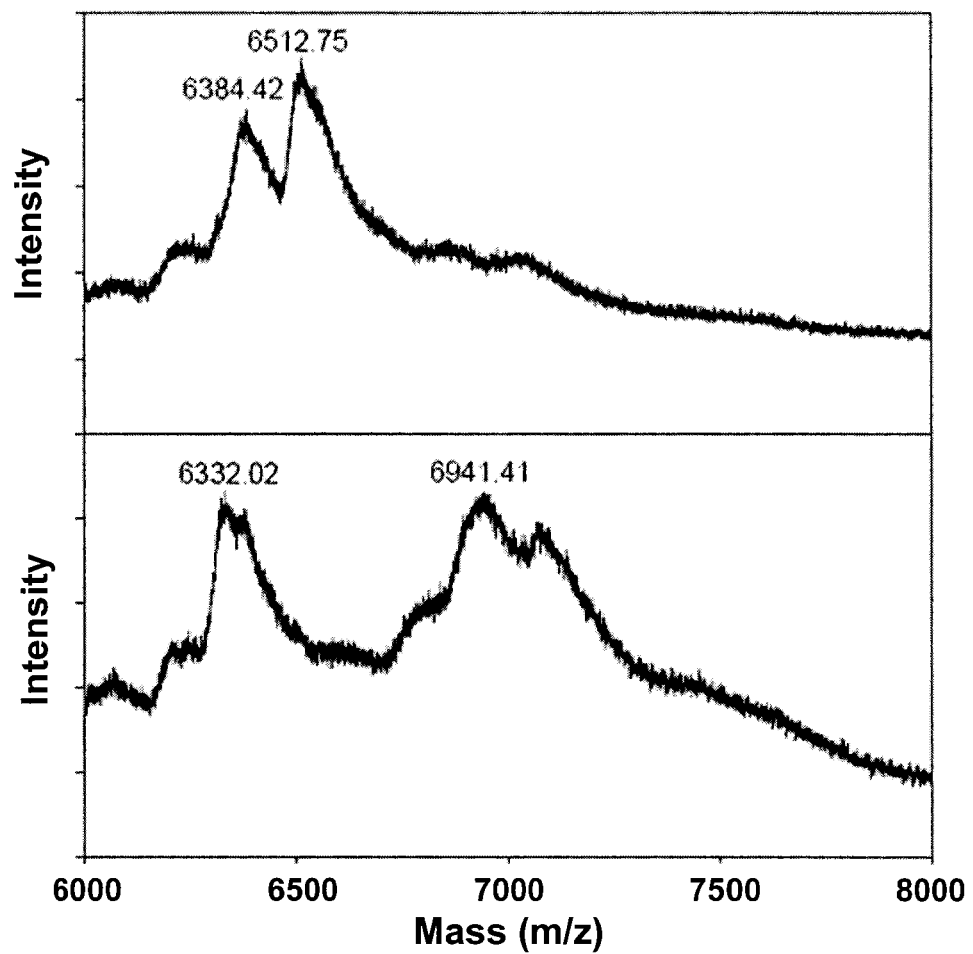
FIG. 4 illustrates the MALDI-TOF mass spectrometric analysis of primer extension products on the 21-nt template (SEQ ID NO.: 8) using TTP (top, showing a mixture of template and TTP product), and B-TTP (bottom: showing a mixture of template and B-TTP product). The mass difference of 418.6 (bottom) reflects the incorporation of the boronic acid labeled thymidine moiety.

The primer extension reaction using natural TTP yielded a DNA product with molecular weight of about 6512 Da as determined using MALDI mass spectrometry (calculated molecular weight: 6518.2 Da) (see FIG. 4). The same reaction using B-TTP yielded a DNA product with a molecular weight of about 6941 Da (calculated molecular weight: 6930.2 Da). Such results demonstrated the successful incorporation of the boronic acid-labeled thymidine unit.

Example 6

Incorporation of B-TTP into DNA by PCR

Each 50 μl reaction was performed with 1.2 μM of Primer 3 (SEQ ID NO: 5) and Primer 4 (SEQ ID NO.: 6), and oligonucleotide Template 2 (SEQ ID NO.: 7), 0.25 mM of each dNTPs, 0.25 mM of labeled-TTP (B-TTP), and 3.5 units of High Fidelity DNA polymerase (Roche, Indianapolis, Ind.) under conditions of 1 cycle at 94° C. for 2 min, 30 cycles at 94° C. for 20 s, 59° C. for 30 s, 72° C. for 1 min, and 1 cycle at 72° C. for 7 min. Ten microliters of each amplification product was separated by gel electrophoresis on 1.5% agarose, stained with ethidium bromide, and visualized under UV light.

Example 7

Immobilization of Beads

25 μL of BioMag Carboxyl beads (Bangs Laboratories, Inc. Fishers, Ind.) were washed four times with 0.5 mL of coupling buffer (0.01M K$_2$HPO$_4$, 0.15 M NaCl at pH 5.5). The supernatant was aspirated to leave the beads as a wet cake on the container wall. 0.5 mL of coupling agent (20 mg EDCl in 20 mL of water) was added to beads and the mixture was shaken briefly for 30 min. Fifty mg of fibrinogen in 22 mL of coupling buffer was added and the mixture was shaken overnight. The beads were separated by magnetic separator and washed by 5 mL of wash buffer (0.01M Tris, 0.15 M NaCl, 0.1% w/v BSA, 0.1% NaN$_3$ and 0.001 EDTA at pH 7.4) three times. The immobilized beads were stored at 2-8° C. as a suspension in wash buffer. During this phase, the immobilization efficiency was monitored by the Kaiser test (Kaiser et al., *Anal. Biochem.* 1970, 34, 595-598).

Example 8

Deglycosylation of Fibrinogen

The carbohydrate moiety in fibrinogen was cleaved by trifluoromethanesulfonic acid (TFMS)-mediated chemical deglycosylation strategies (Edge et al., *Anal. Biochem.* 1981, 118, 131-137; Edge A. S., *Biochem. J.* 2003, 376, 339-350, incorporated herein by reference in its entirety). To 100 mg of pre-cooled fibrinogen in an absolute dry reaction vial was added 1.5 mL of the pre-cooled TFMS, the vial was then sealed and gently shaken for 2-5 min until the protein was completely dissolved. The vial was then incubated on ice for additional 25 min with occasional shaking. 400 µL of a 0.2% bromophenol blue solution as an indicator was added into the reaction vial and the resulting mixture was gently shaken. Then a total of approximately 30 mL of pre-cooled 60% pyridine was added immediately until the solution color changed from red to blue. The deglycosylated protein was then purified by Sephadex G-25 medium (GE Healthcare) and the elution was dried by a vacuum-freeze evaporator.

Example 9

Periodation of Fibrinogen

Sodium acetate (100 mL, 10 mM) was added to a solution of 100 mg of fibrinogen in 100 mL of 0.2 mM sodium periodate. The mixture was incubated for 30 min on ice-bath. 10 mL of 10 mM glycerol was then added, and the mixture was incubated for 30 min at room temperature to consume the excess periodate. The resulting fibrinogen was purified by IWT TMD-8 ion-exchange resin (Sigma-Aldrich) and concentrated using a vacuum-freeze evaporator (lypholizer or freeze dryer). (See, *J. Biol. Chem.* 1964, 239, 567; *J. Biol. Chem.* 1962, 237, 1021, incorporated herein by reference in its entirety).

Example 10

SELEX Selection of Aptamers

Oligonucleotide Template 5 (SEQ ID NO.: 10) containing 50 randomized positions and complementary at its ends to Primer 20.227 (SEQ ID NO.: 11) and Primer 20.226 (SEQ ID NO.: 12) were synthesized. The starting dsDNA library was constructed by a 25-round PCR amplification using Taq polymerase from DNA template in the presence of four standard nucleotides (dNTPs) by Effendorf thermal cycler. The PCR product was then concentrated by a YM-30 spin column (Millipore). The ssDNA pool was then prepared by one-round PCR using the above dsDNA product using [$\alpha$-$^{32}$P] dATP, dATP, dCTP, dGTP and B-TTP. The DNA pool was incubated with the fribrinogen-immobilized BioMag carboxyl beads for one hour in binding buffer (300 mM NaCl, 5 mM MgCl$_2$, 20 mM Tris-HCl at pH 7.6). The incubated beads were then separated by using a magnetic separator and washed by buffer for six times and then fibrinogen-containing (10 µg/mL) binding buffer for three times. Aliquots (20 µL) were taken from every washing, and radioactivity in each aliquot was determined using a Beckman LS 6500 liquid scintillation counter. The fractions from the fibrinogen washings were combined, extracted with phenol, precipitated in ethanol, and amplified by PCR for the next round of SELEX using the same protocol, as shown in Scheme 4, FIG. 20.

Example 11

Molecular Cloning and Sequencing

Clones of the ssDNA pool were prepared after 13 rounds of SELEX selection as described in Example 10. An aliquot of the ssDNA solution was PCR amplified. The PCR reagent mix and cycling conditions were similar to those described above and only 20 PCR cycles were performed. Final extension was carried out for 15 min at 72° C. The PCR product was ligated into the pCR4-TOPO vector (Sigma, St. Louis, Mo.) at room temperature for 30 min. This ligation product was transformed into One Shot TOP10 Chemically Competent *E. coli* on ice for 30 min and heat-shocked at 42° C. for 30 sec and the transformation liquid was spread on a pre-warmed LB plate and incubated overnight at 37° C. Hundreds of colonies were raised. Forty colonies were picked up at random and individually cultured overnight in LB medium containing 100 µg/mL ampicillin. Plasmids from these colonies were isolated and purified using the PURELINK™ HQ Mini Plasmid Purification Kit (Sigma, St. Louis, Mo.), and sequenced using the T3 promoter primer.

Example 12

Binding Assays

Dissociation constants in solution were determined by equilibrium filtration (Jenison et al., *Science* 1994, 263, 1425-1429; Huang & Szostak, *RNA* 2003, 9: 1456-1463, incorporated herein by reference in their entireties). Using this technique, the bound and unbound ligand (DNA) partition between the two portions separated by a membrane. DNA was first amplified into dsDNA using two primers by PCR (25 cycles of 0.5 min at 94° C., 0.5 min at 46° C., and 0.5 min at 72° C., followed by 5 min at 72° C.). The dsDNA product was then split into ssDNA using one primer and $\alpha$-$^{32}$P-dATP by one-round PCR. The $^{32}$P-labeled ssDNA ligand (10 nM) and the protein (1-1000 nM) in the 100 µL of binding buffer were incubated for 15 min at 25° C. prior to loading into the Microcon YM-100 unit (Millipore, Billerica, Mass.). The solution was centrifuged at 13,000 g for 10 sec to saturate the membrane, and the filtrate was transferred back to the unit. The solution was centrifuged for another 20 sec, and the filtrate (about 10 µL) was collected. Aliquots (10 µL) were taken from both the remaining solution and the filtrate, and radioactivity in each aliquot was determined by Beckman LS 6500 liquid scintillation counter. All binding assays were duplicated. The equilibrium dissociation constants ($K_d$) of the ligand-protein interaction were obtained by fitting the dependence of bound fractions of specific binding on the concentration of the aptamers to the equation $Y=B \max X/(K_d+X)$, using the SigmaPlot program.

Figure 12A:
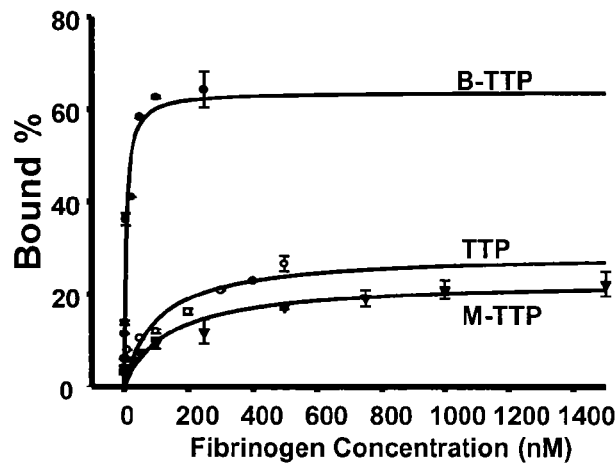
FIGS. 12A-12C are binding curves of B-TTP-labeled aptamer 85A (SEQ ID NO.: 13), TTP-labeled 85A, M-TTP-labeled 85A with fibrinogen (FIG. 12A), deglycosylated fibrinogen (FIG. 12B) and periodated fibrinogen (FIG. 12C).
Figure 12B:
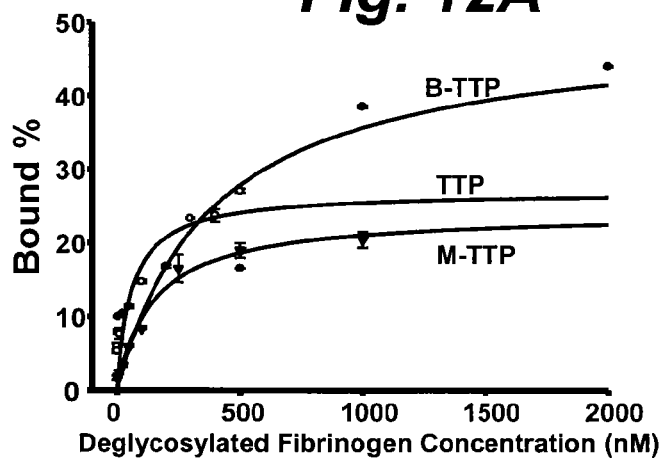
Figure 12C:
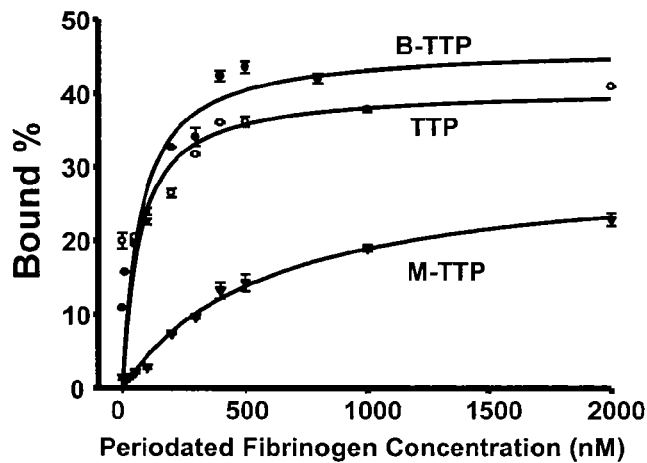
Figure 13A:
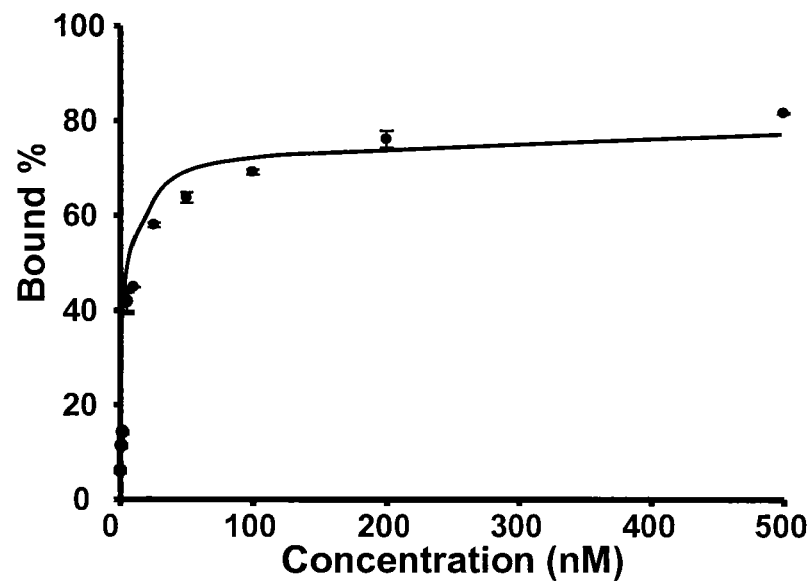
FIG. 13A is a binding curve of B-TTP-labeled aptamer 85B (SEQ ID NO.: 14) with fibrinogen.
Figure 13B:
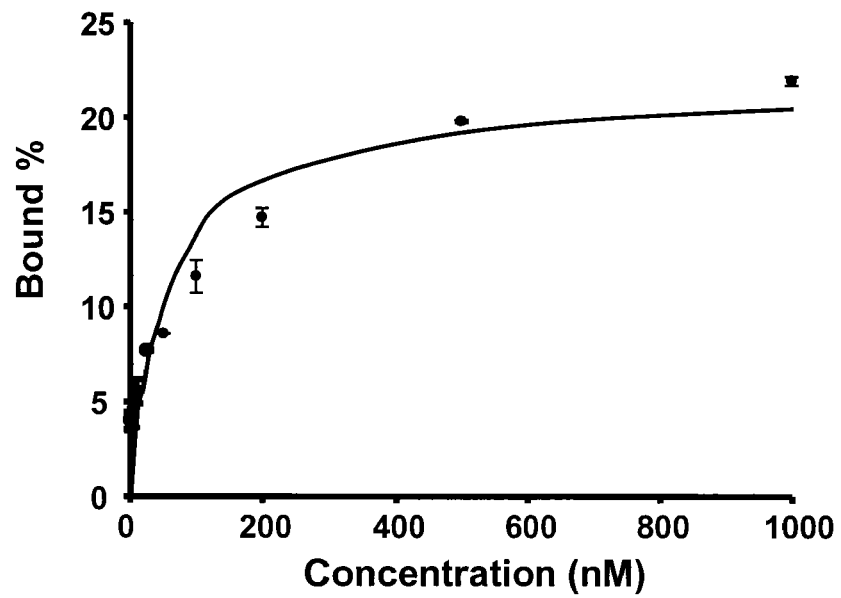
FIG. 13B is a binding curve of TTP-85B aptamer with fibrinogen.
Figure 14A:
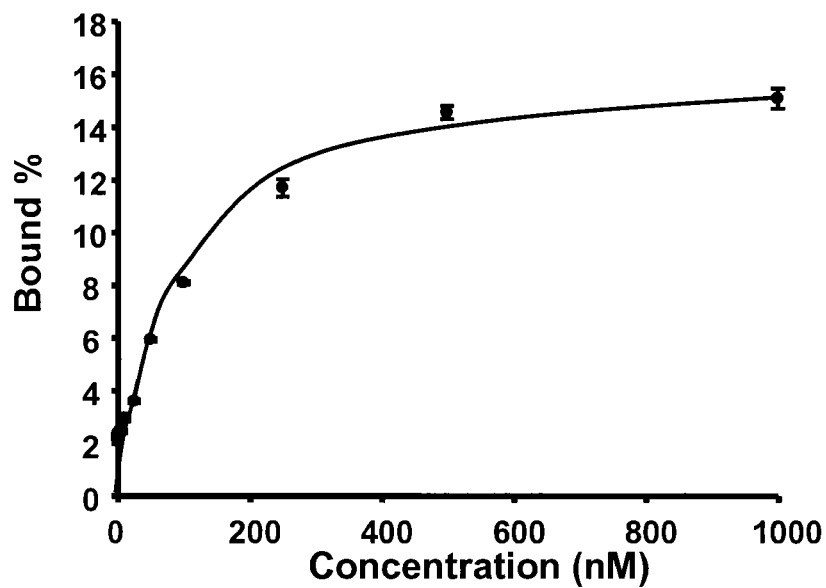
FIG. 14A is a binding curve of B-TTP-labeled 85B aptamer with deglycosylated fibrinogen.
Figure 14B:
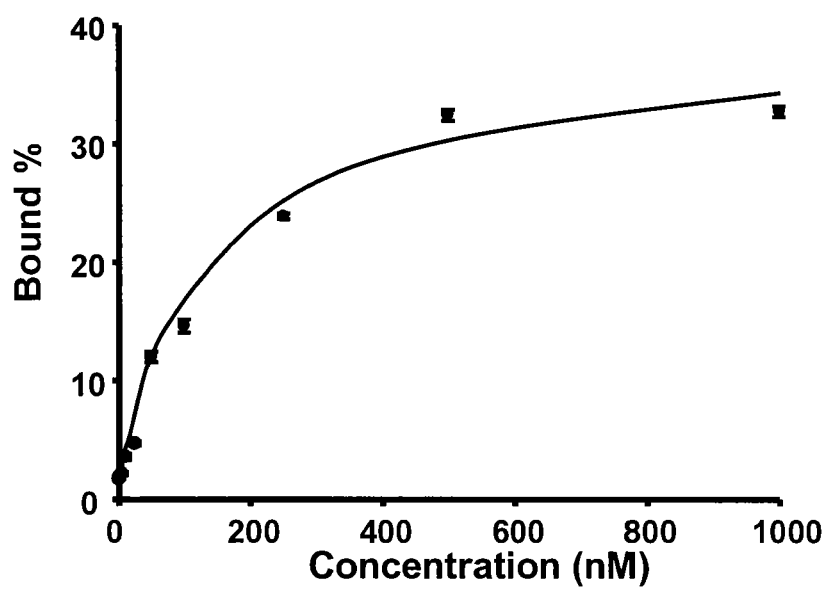
FIG. 14B is a binding curve of TTP-85B aptamer with deglycosylated fibrinogen.
Figure 15A:
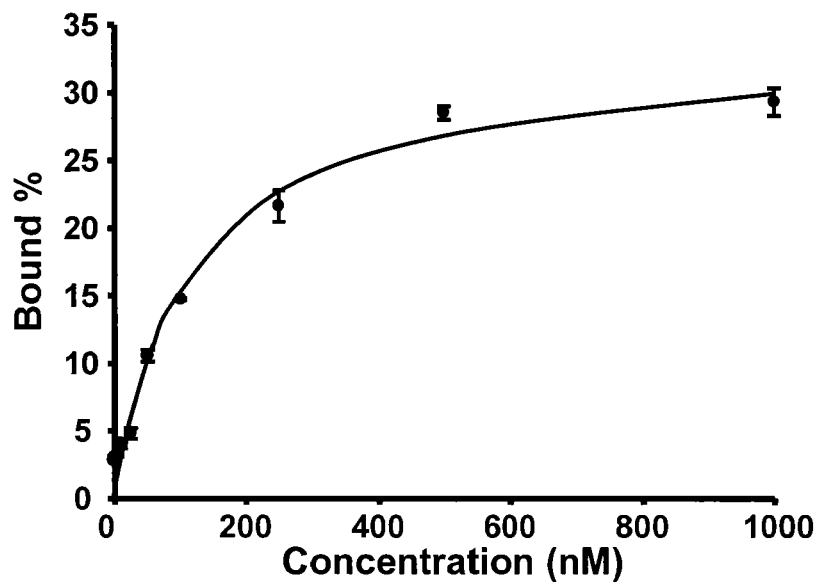
FIG. 15A is a binding curve of B-TTP-labeled 85B aptamer with periodated fibrinogen.
Figure 15B:
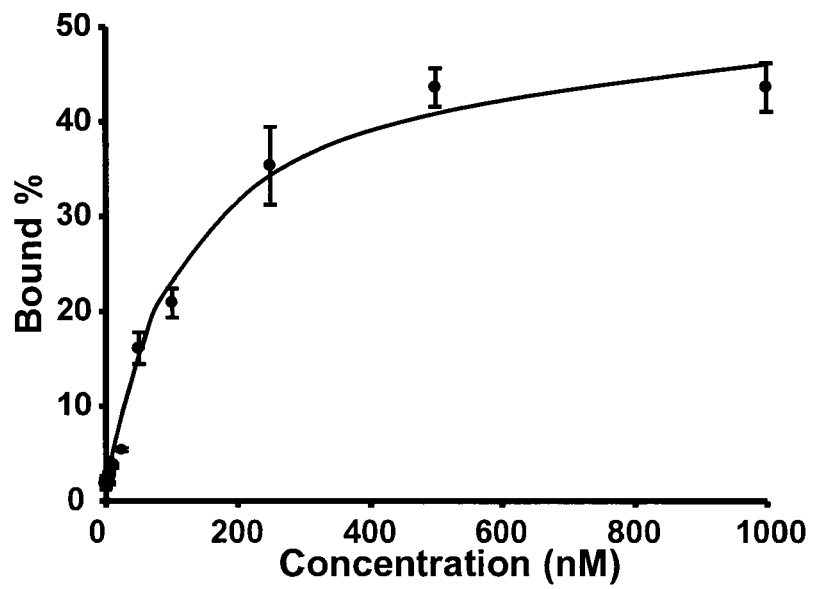
FIG. 15B is a binding curve of TTP-85B aptamer with periodated fibrinogen.
Figure 16A:
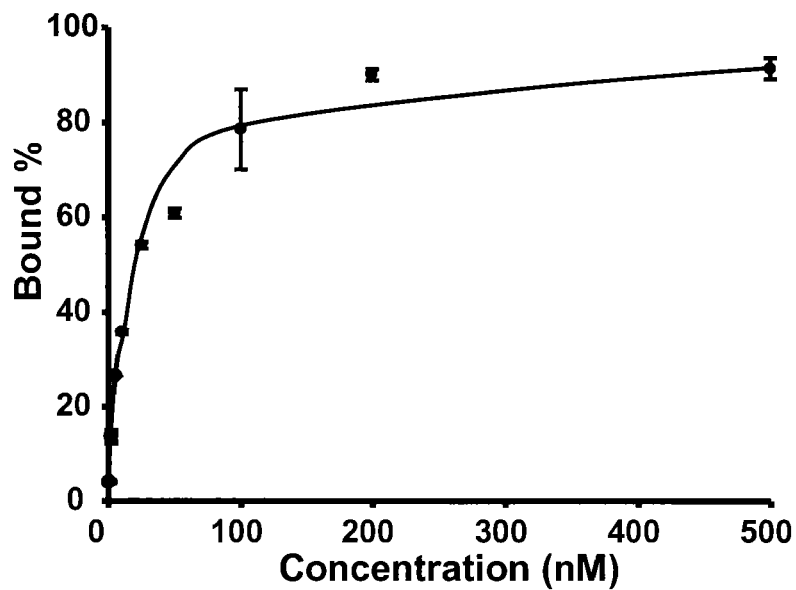
FIG. 16A is a binding curve of B-TTP-labeled 85C aptamer (SEQ ID NO.: 15) with fibrinogen
Figure 16B:
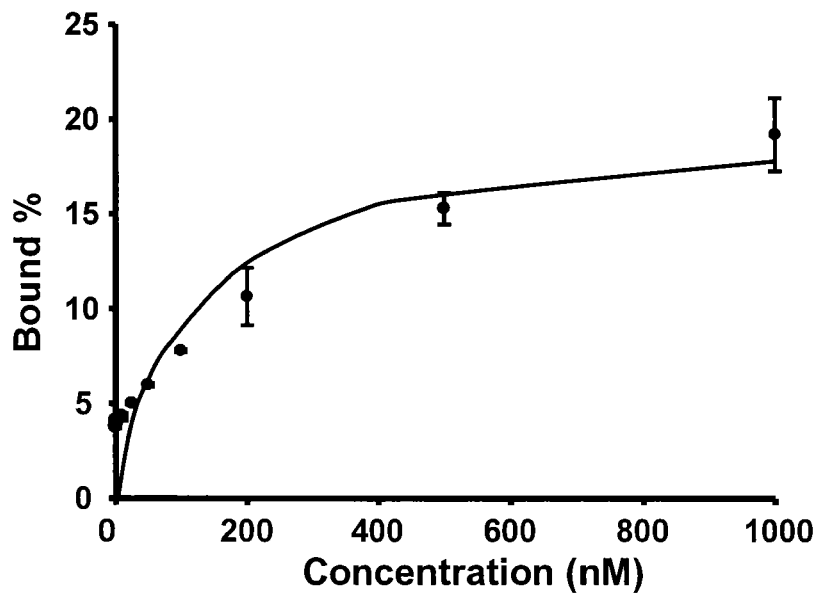
FIG. 16B is a binding curve of TTP-85C aptamer with fibrinogen
Figure 17A:
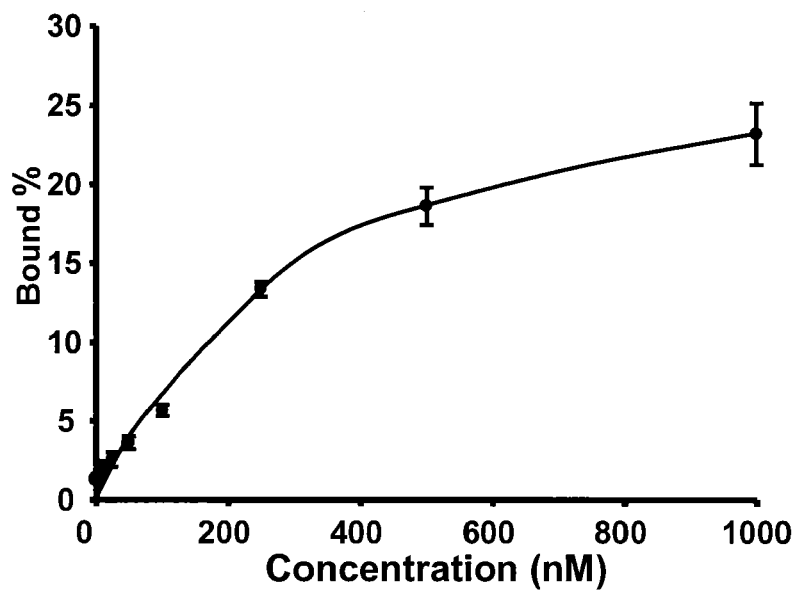
FIG. 17A is a binding curve of B-TTP-labeled 85C aptamer with deglycosylated fibrinogen.
Figure 17B:
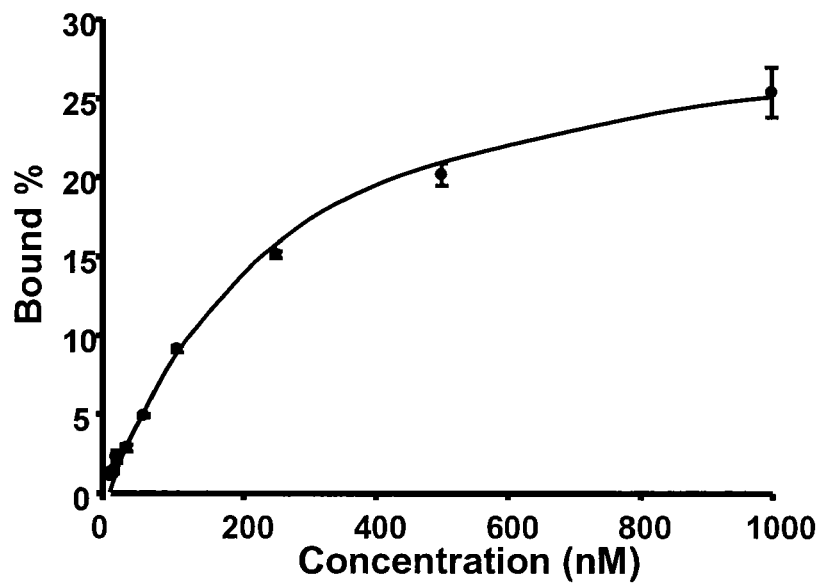
FIG. 17B is a binding curve of TTP-85C aptamer with deglycosylated fibrinogen.
Figure 18A:
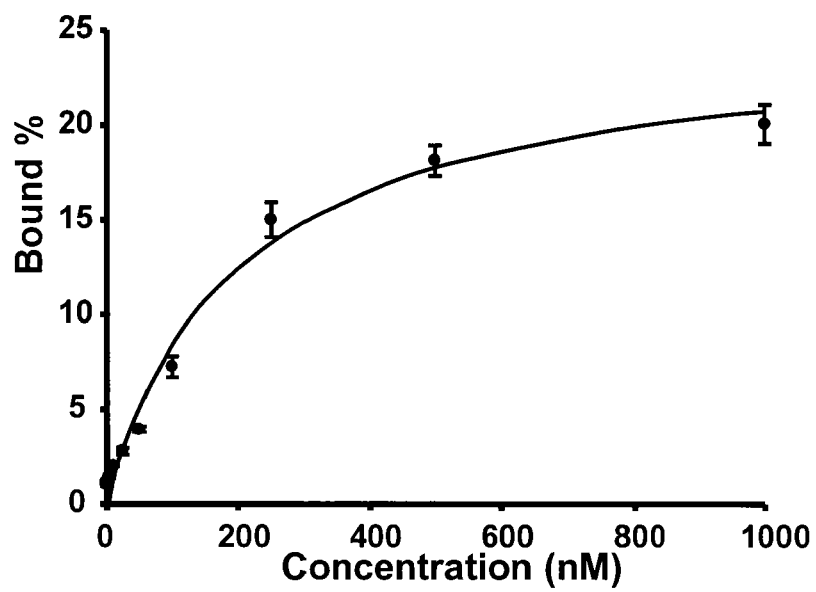
FIG. 18A is a binding curve of B-TTP-labeled 85C aptamer with periodated fibrinogen.
Figure 18B:
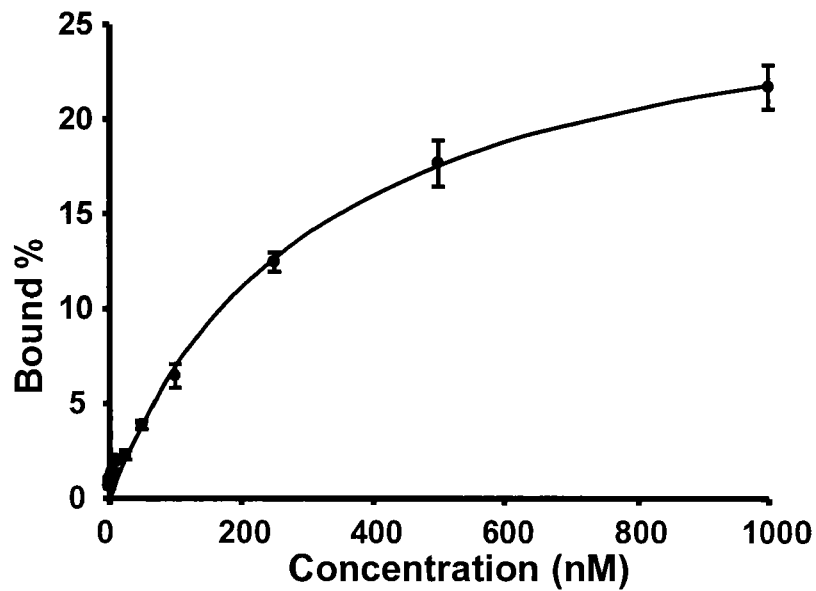
FIG. 18B is a binding curve of TTP-85C aptamer with periodated fibrinogen.

To determine the extent to which the aptamers 85A (SEQ ID NO.: 13), 85B (SEQ ID NO.: 14), and 85C (SEQ ID NO.: 15) bind specifically to fibrinogen, their dissociation constants ($K_d$) were measured using the equilibrium filtration method with radiolabeled $\alpha$-$^{32}$P-dATP. The binding curves for aptamer 85A (SEQ ID NO.: 13) incorporating TTP, B-TTP, or M-TTP are shown in FIGS. 12A-12C. The target substrate to which the aptamer was binding was fibrinogen (FIG. 12A), deglycosylated fibrinogen (FIG. 12B) and periodated fibrinogen (FIG. 12C). The results are listed in Tables 1 and 2. For aptamers 85B and 85C, the binding curves are shown in FIGS. 13A-19B.

TABLE 1

Binding constants of aptamers with fibrinogen

| Aptamer | Kd (nM) | |
|---|---|---|
| | BTTP- | dTTP- |
| 114A (87J) | 30 | 80 |
| 114H (85A) | 6.3 | 102 |
| 114O (85B) | 5.8 | 64 |
| 114F (85C) | 16 | 193 |
| 114N (85E) | 5.9 | 87 |

TABLE 2

Calculated dissociation constants (nM) of aptamers with different fibrinogens

| Aptamer | Fibrinogen | | Deglycosylated Fibrinogen | | Periodate-treated Fibrinogen | |
| --- | --- | --- | --- | --- | --- | --- |
| | B-TTP | TTP | B-TTP | TTP | B-TTP | TTP |
| 85A | 6.17 ± 1.35 | 101.55 ± 39.71 | 390.14 ± 144.84 | 60.22 ± 17.95 | 70.70 ± 18.40 | 67.43 ± 24.95 |
| 85B | 6.44 ± 0.81 | 63.81 ± 16.88 | 86.17 ± 16.40 | 139.58 ± 15.89 | 117.98 ± 16.97 | 130.18 ± 18.67 |
| 85C | 17.11 ± 2.08 | 122.15 ± 43.71 | 371.10 ± 61.87 | 256.39 ± 28.90 | 202.72 ± 28.05 | 321.02 ± 39.73 |

TABLE 3

Comparison of aptamer 85A binding (Kd (nM)) when labeled with a B-TTP, unlabeled (TTP) or when the B-TTP is pretreated with peroxide

| Aptamer | BTTP | TTP | MTTP | $H_2O_2$-treated |
| --- | --- | --- | --- | --- |
| 85A | 6.2 ± 1.4 | 102 ± 40 | 138 ± 36 | 173 ± 30 |

TABLE 4

Specificity of binding of aptamer 85A with different glycoproteins

| 85A | fibrinogen | fetuin | Alpha-1 acid |
| --- | --- | --- | --- |
| BTTP | 6.2 ± 1.4 nM | 2200 nM | 700 nM |
| TTP | 102 ± 40 nM | 1600 nM | 600 nM |

All boronic acid-labeled aptamers (B-TTP aptamers) bind fibrinogen with $K_d$ values in the low nM range. In contrast, the DNA pool after the 13$^{th}$ round of selection showed an average $K_d$ of about 5 μM. The same aptamers prepared using all natural dNTPs (TTP aptamers) were also tested. These TTP aptamers showed $K_d$ values that were 10-20 fold higher than that of B-TTP aptamers. For example, with aptamer 85A the $K_d$ of B-TTP aptamer for fibrinogen is 6 nM, while the $K_d$ for the corresponding unlabeled TTP aptamer is 101 nM (Table 3), thereby showing that boronic acid was indeed involved in binding.

The binding constants of a phenylboronic acid against a variety of diol sugars both shows the selective binding of a boronic acid to diols, and that binding is minimal to glucose itself, as shown in Table 5.

TABLE 5

Apparent binding constants of phenyboronic acid at pH 7.4, 0.10 M phosphate

| Diol | $K_{eq}$ | Diol | $K_{eq}$ |
| --- | --- | --- | --- |
| Alizarin Red S. | 1298 | Cis-1,2-cyclopentane diol | 20 |
| catechol | 828 | Sialic acid | 21 |
| D-sorbitol | 440 | Glucuronic acid | 16 |
| D-fructose | 162 | D-galactose | 15 |
| D-tagatose | 130 | D-xylose | 14 |
| D-mannitol | 118 | D-mannose | 13 |
| L-sorbose | 115 | D-glucose | 5 |
| 1,4 anhydroerythritol | 106 | Diethyl tartrate | 4 |
| D-erythronic-γ-lactone | 30 | maltose | 3 |
| L-arabinose | 25 | lactose | 2 |
| D-ribose | 24 | sucrose | 1 |

Example 13

PSA-glycosylation Specific Aptamers

Both high PI and low PI fractions of PSA from Lee Bio-Solutions were used. The major difference between the high and low PI fractions of PSA is their glycosylation patterns. The pI difference mostly reflects a different degree terminal sialylation. Sialic acid is acidic and lowers the pI of a glycoprotein. It has been suggested that high pI fractions tend to be more correlated with prostate cancer than low pI fractions (in each fraction separated by pI, there is still heterogeneity).

Using the same approach as described in Examples 10 and 11 above, PSA aptamers specific for the high pI fraction of PSA were selected.

Twenty clones selected according to the protocols described in Examples 10 and 11 were isolated and sequenced. FIG. 26 shows the sequences of 10 selected aptamers (SEQ ID NO.: 62-71). There is a sequence, 5'-TATCGGTTTGCCATCG-3' (SEQ ID NO.: 71, shown in FIG. 26) common to all the aptamers specific for the high PI PSA. However, the position of the common sequence SEQ ID NO.: 72) within each aptamer varied.

The binding properties of five clones were studied further. FIGS. 30A-30E show the binding curves for five such aptamers (aptamers 5A-5E, SEQ ID NOs.: 59-68) with high and low PI PSA. Table 6 presents the numerical binding (dissociation constants) results.

TABLE 6

PSA aptamer binding and selectivity results

| | $K_d$ (nM) | | |
| --- | --- | --- | --- |
| Aptamer | High-pI PSA | Low-pI PSA | Selectivity |
| 5A | 7 ± 1 | 190 ± 50 | 27 |
| 5B | 8 ± 1 | 830 ± 240 | 100 |
| 5C | 16 ± 2 | 670 ± 210 | 42 |
| 5D | 19 ± 2 | 750 ± 250 | 40 |
| 5E | 34 ± 2 | 820 ± 250 | 24 |

Most aptamers had $K_d$ values in the range of 7-35 nM, comparable to that of antibodies to their respective antigens. The aptamers showed high selectivity, between about 24 to 100 fold, for the high pI fraction versus the low pI fraction, showing that the selected aptamers can distinguish between two glycoforms of a glycoprotein.

Example 14

Synthesis of the Napthalimide-based Boronic Acid-modified Thymidine Triphosphate (B-TTP)

As illustrated in the scheme shown in FIG. 27, the steps of the synthesis are:

(i) 4-Aminomethylbenzyl alcohol preparation 4-(Hydroxymethyl)benzonitrile (1.0 g, 7.5 mmol) dissolved in dry tetrahydrofuran (20 ml) was added slowly into a suspension of LiAlH$_4$ (866 mg, 22.8 mmol) in tetrahydrofuran (20 ml) at room temperature. Foaming with bubble formation was observed while stirring. The light yellow-green suspension was refluxed under N$_2$ overnight. After cooling down to room temperature, methanol (5 ml) was added to the suspension to quench the reaction. The suspension was foaming while stirring and cooling down in ice-bath. When no more bubble formation was observed, sodium hydroxide (20%, 15 ml) solution was added into the suspension. The solution became colorless while white precipitate was observed. The solution was concentrated in vacuo and the residue was suction filtered. The solid was repeatedly washed with methylene dichloride. The filtrate was combined and washed with water. The organic phase was separated and concentrated by a rotavapor. White solid was obtained as product (1.0 g, yield 98%). The product underwent prolonged drying in vacuo to remove residue solvent before the next step reaction. $^1$H-NMR (CDCl$_3$): δ7.31 (m, 4H), 4.67 (s, 2H), 3.85 (s, 2H), 1.76 (s broad, 3H); $^{13}$C-NMR (CDCl$_3$): δ142.7, 139.9, 127.5, 127.5, 65.2, 46.4

4-Boc-aminomethylbenzyl alcohol

Into the solution of 4-aminomethylbenzyl alcohol (444 mg, 3.2 mmol) and triethylamine (0.47 ml, 3.3 mmol) in dry tetrahydrofuran (5 ml) was added dropwise di-t-butyl dicarbonate (750 mg, 3.4 mmol) in dry tetrahydrofuran (3 ml). The mixture was stirred at room temperature overnight. The solution was concentrated on a rotavapor and the residue was dissolved in ethyl acetate (20 ml). The solution was sequentially washed with sodium bisulfate solution (5%, ×1), saturated sodium bicarbonate solution (×1) and brine (×1), and then dried over magnesium sulfate. The solution was filtered and dried in vacuo. White powder was obtained as product (720 mg, yield 94%). $^1$H-NMR (CDCl$_3$): δ7.27 (m, 4H), 4.92 (s broad, 1H), 4.65 (s, 2H), 4.27 (d, 2H), 2.22 (s broad, 1H), 1.45 (s, 9H); $^{13}$C-NMR (CDCl$_3$): δ156.1, 140.3, 138.4, 127.8, 127.4, 79.7, 65.1, 44.6, 28.6

(iii) (4-Boc-aminomethylbenzyl)methansulfonate

Into the solution of 4-Boc-aminomethylbenzyl alcohol (700 mg, 3.0 mmol) and triethylamine (0.86 ml, 6.2 mmol) in dry tetrahydrofuran (12 ml) cooled down at ice bath, MsCl (0.38 ml, 4.9 mmol) was added dropwise. The mixture was stirred for 1 h in an ice bath. The solution was concentrated on a rotavapor and the residue was dissolved in 25 ml of ethyl acetate. The solution was sequentially washed with sodium bisulfate solution (5%, ×1), saturated NaHCO$_3$ solution (×1) and brine (×1), and then dried over magnesium sulfate The solution was filtered and dried in vacuo. Colorless oil was obtained as product (896 mg, yield 96%), which turned into white crystal after prolonged drying in vacuo. $^1$H-NMR (CDCl$_3$): δ7.35 (m, 4H), 5.22 (s, 2H), 4.95 (s broad, 1H), 4.33 (d, 2H), 2.91 (s, 3H), 1.46 (s, 9H); $^{13}$C-NMR (CDCl$_3$): δ156.1, 140.7, 132.5, 129.4 128.0, 79.9 71.4, 44.4, 38.5, 28.6

(iv) 4-amino-N-(4'-Boc-aminomethylbenzyl)-1,8-naphthalimide

4-Amino-1,8-naphthalimide (820 mg, 3.85 mmol) in dry DMF (20 ml) was treated with 2 M NaOMe in MeOH (3 ml) until it became homogenous solution with a deep red color, which took several minutes. (4-Boc-aminomethylbenzyl) methansulfonate (1.21 g, 3.85 mmol) was added later. The solution was stirred for 3 h and then quenched by adding H$_2$O (100 ml). The suspension was extracted with ethyl acetate (100 ml, ×2). The organic extraction was combined and concentrated into 100 ml. The solution was washed with H$_2$O (25 ml, ×3) and dried over MgSO$_4$. The removal of solvent on a rotavap gave orange solid powder (1.5 g, yield 90%) product. $^1$H-NMR (DMSO): δ8.63 (d, 1H, J=7.6 Hz), 8.44 (dd, 1H, J$_1$=7.2 Hz, J$_2$=0.8 Hz), 8.21 (d, 1H, J=9.2 Hz), 7.66 (t, 1H, J=8.0 Hz,), 7.49 (s broad, 2H), 7.20 (m, 4H), 6.86 (d, 1H, J=8.4 Hz), 5.19 (s, 2H), 4.06 (d, 2H, J=6 Hz), 1.366 (s, 9H); $^{13}$C-NMR (DMSO): 6163.8, 162.9, 155.7, 152.9, 138.8, 136.4, 134.2, 131.2, 129.8, 129.5, 127.4, 126.9, 124.0, 121.7, 119.4, 108.2, 107.3, 77.7, 43.1, 42.2, 28.2.

(v) 4-(2-bromobenzyl)amino-N-(4'-Boc-aminomethylbenzyl)-1,8-naphthalimide

4-Amino-N-(4'-Boc-aminomethylbenzyl)-1,8-naphthalimide (1.50 g, 3.49 mmol) and sodium hydride (60% dispersed in mineral oil, 306 mg, 7.66 mmol) were mixed in dry dimethylformamide (20 ml). The mixture was stirred for 5 min and then 2-bromobenzyl bromide (870 mg, 3.49 mmol) was added. The mixture was stirred for 3 h before quenching with water (150 ml). The suspension was extracted with ethyl acetate (25 ml, ×3). The organic extractions were combined and washed with water (50 ml). After separation, the organic solvent was removed on a rotavap and the residue was purified on a silica gel column. The product was eluted out by ethyl acetate/hexane (1:4). Yellow powder (840 mg, yield 40%) was obtained as product. $^1$H-NMR (DMSO): δ8.58 (d, 1H, J=7.2 Hz), 8.43 (d, 1H, J=8.4 Hz), 8.13 (d, 1H, J=8.4 Hz), 7.64-7.61 (m, 2H), 7.49 (d, 2H, J=8.0 Hz), 7.37 (dd, 1H, J$_1$=7.6 Hz, J$_2$=1.6 Hz), 7.30-7.28 (m, 1H), 7.27-7.18 (m, 2H), 6.68 (d, 1H, J=8.4 Hz), 5.78 (s, 1H), 5.33 (s, 2H), 4.75 (s, 1H), 4.69 (d, 2H, J=5.6 Hz), 4.24 (d, 2H, J=5.6 Hz), 1.43 (s, 9H); $^{13}$C-NMR (DMSO): δ164.8, 164.2, 156.0, 149.1, 138.0, 137.2, 136.1, 134.7, 133.5, 131.6, 130.0, 129.8, 129.5, 129.3, 128.1, 127.8, 126.2, 125.2, 123.8, 123.4, 120.6, 111.3, 105.3, 79.6, 48.3, 44.7, 43.2, 28.6

(vi) 4-(2-dihydroxylboryl-benzyl)-amino-N-(4'-Boc-aminomethylbenzyl)-1,8-naphthalimide 4-(2-bromobenzyl)amino-N-(4'-Boc-aminomethylbenzyl)-1,8-naphthalimide (391 mg, 0.65 mmol), PdCl$_2$(dppf) (160 mg, 0.20 mmol), Bis(neopentyl glycolato)diboron (368 mg, 1.63 mmol) and potassium acetate (198 mg, 2.02 mmol) were mixed in a dry flask full of nitrogen. Anhydrous dimethyl sulfoxide (5 ml) was injected into the mixture. The solution was heated between about 80-85° C. under nitrogen for 5 h. After that, the solution was cooled down to room temperature and then water (25 ml) was added to quench the reaction. The solution was extracted with ethyl acetate (25 ml, ×2). The extractions were combined, washed with water (25 ml, ×2) and concentrated with a rotavap. The residue was purified by silica gel column, and the crude product was eluted out by ethyl acetate/methanol=10:1. The crude product was further purified with 20×20 cm preparatory TLC plate developed by ethyl acetate/methanol=5:1. The orange fluorescent band (Rf=0.1-0.5) was cut out and extracted with methanol. Orange color solid was obtained as product (167 mg, yield 45%) 1H-NMR (MeOD): δ8.22 (d, 1H, J=8.0 Hz), 8.04 (d, 1H, J=8.8 Hz), 7.58 (d, 1H, J=7.2 Hz), 7.42 (d, 2H, J=7.6 Hz), 7.33-7.25 (m, 4H), 7.19-7.16 (m, 3H), 6.17 (d, 1H, J=8.4 Hz), 5.30 (s, 2H), 4.55 (s, 2H), 4.15 (s, 2H), 1.42 (s, 9H); $^{13}$C-NMR (MeOD): δ167.8, 166.2, 164.7, 158.7, 141.6, 139.5, 138.9, 133.6, 130.9, 129.4, 129.1, 129.0, 128.8, 128.3, 127.5, 126.4, 119.6, 104.0, 101.8, 80.3, 47.7, 45.0, 43.8, 30.9, 28.9

(vii) 4-(2-dihydroxylboryl-benzyl)amino-N-(4'-aminomethylbenzyl)-1,8-naphthalimide 4-(2-dihydroxylboryl-benzyl)amino-N-(4'-Boc-aminomethylbenzyl)-1,8-naphthalimide (96 mg, 0.17 mmol) was suspended in CH$_2$Cl$_2$ (1.5 ml) and trifluoroacetic acid (0.15 ml, 2.0 mmol) was added in one-shot. The mixture was stirred at room temperature for 1.5 h and then concentrated by rotavap. The residue was prolonged dried in vacuo and directly used for the next step without any purification. $^1$H-NMR (MeOD): δ8.21 (d, 1H, J=6.8 Hz), 8.03 (t, 1H, J=4 Hz), 7.58 (d, 1H, J=7.2 Hz), 7.44-7.37 (m, 4H), 7.29-7.25 (m, 4H), 7.17 (t, 1H, J=7.2 Hz), 6.16 (d, 1H, J=8.8 Hz), 5.32 (s, 2H), 4.55 (s, 2H), 3.86 (s, 2H); $^{13}$C-NMR (MeOD): δ167.8, 166.1, 141.6, 140.2, 138.8, 133.6, 130.9, 129.4, 129.3, 129.2, 128.9, 127.5, 126.3, 119.4, 103.8, 101.8, 47.9, 45.5, 43.8

(viii) 4-(2-dihydroxylboryl-benzyl)-amino-N-(4'-azidoacetyl-aminomethylbenzyl)-1,8-naphthalimide 4-(2-dihydroxylboryl-benzyl)amino-N-(4'-aminomethyl-benzyl)naphthalimide (30 mg, 0.064 mmol), EDCl (25 mg, 0.13 mmol), HOBut (10 mg, 0.08 mmol) and azidoacetic acid (8 mg, 0.08 mmol) were mixed in dimethylformamide (1.5 ml). The mixture was stirred at room temperature under nitrogen overnight. The mixture was washed with saturated $K_2CO_3$(aq) solution to remove DMF and impurities. After that, the mixture was loaded on 20×20 cm preparatory TLC plate. Ethyl acetate/methanol (4:1) was used to develop the plate. The orange fluorescent band (Rf=0.2-0.3) was cut out and extracted with MeOH. Orange color solid was obtained as product (13 mg, yield 37%). $^1$H-NMR (MeOD): δ8.23 (d, 1H, J=7.2 Hz), 8.06 (d, 1H, J=8.4 Hz), 7.59 (d, 1H, J=6.8 Hz), 7.42 (d, 2H, J=7.6 Hz), 7.33 (d, 2H, J=8.0 Hz), 7.27 (t, 2H, J=7.6 Hz), 7.21~7.17 (m, 3H), 6.19 (d, 1H, J=8.8 Hz), 5.30 (s, 2H), 4.55 (s, 2H), 4.34 (s, 2H), 3.88 (s, 2H); $^{13}$C-NMR (MeOD): δ170.1, 167.8, 164.6, 141.5, 139.3, 138.9, 138.2, 133.6, 130.9, 129.4, 129.2, 128.9, 128.8, 127.6, 126.5, 119.8, 104.3, 101.8, 53.1, 47.5, 44.2, 44.0, 43.8, 30.9, 18.5

Example 15

Synthesis of N-TTP

As shown in the scheme illustrated in FIG. 28, 4-(2-dihydroxylboryl-benzyl)amino-N-(4'-azidoacetyl-aminomethylbenzyl)-1,8-naphthalimide (14 mg, 0.025 mmol), M-TTP (16 mg, 0.027 mmol) were mixed in a flask full of nitrogen. Tris(triazolyl)amine (2.7 mg, 0.0051 mmol), CuBr (0.37 mg, 0.0025 mmol) were mixed in another 200 μl of ethanol/water (1:1), which was added later into the flask. The entire mixture was sonicated for several minutes and then stirred at room temperature under nitrogen for 4 h. The mixture was concentrated in vacuo and the residue was repeated extracted with water until the aqueous extraction was no longer deep red. The aqueous extractions were combined and centrifuged to remove insoluble solid. After lyophilization, the extracted product was purified by HPLC (C18 RP preparatory column). Elution conditions: Water/$CH_3CN$ (5 ml/min), 0-30 min ($CH_3CN$ 25%), Rt=14 min. The collected fraction was lyophilized into orange color powder (1 mg, yield 5%). $^{11}$B-NMR ($D_2O$, internal standard: 15% $BF_3$ in ether): δ29.9; $^{31}$P-NMR ($D_2O$, internal standard: 85% $H_3PO_4$): δ-5.55, -10.54, -21.60; MS (ESI-): m/z 1032.3 (100) [M–H–$2H_2O$—$HPO_3$]$^-$, 1112.3 (20) [M–H–$2H_2O$]$^-$, 1134.3 [M–H–$3H_2O$+$HOCH_3$]$^-$, 1054.3 [M–H–$3H_2O$+$HOCH_3$—$HPO_3$]$^-$; MS (MALDI linear): m/z 1112.57 (100) [M–H–$2H_2O$]$^-$, 1032.97 (45) [M–H–$2H_2O$—$HPO_3$]$^-$

Example 16

Fluorescence Binding Test

Solutions of N-TTP (1×10 M) and N-TTP (1×10$^{-6}$ M) with D-fructose (0.1 M) were prepared in 0.1 M phosphate buffer at pH 7.4, respectively. These two solutions were mixed in a ration of D-fructose concentration increasing from 10$^{-3}$ to 0.1 M. 3 ml of each mixed solution was used to test the fluorescence intensity several minutes after mixing. Eight points were collected for the calculation of apparent binding constant Ka assuming a 1:1 complex formation mechanism. The test has been repeated three times.

Figure 29A:
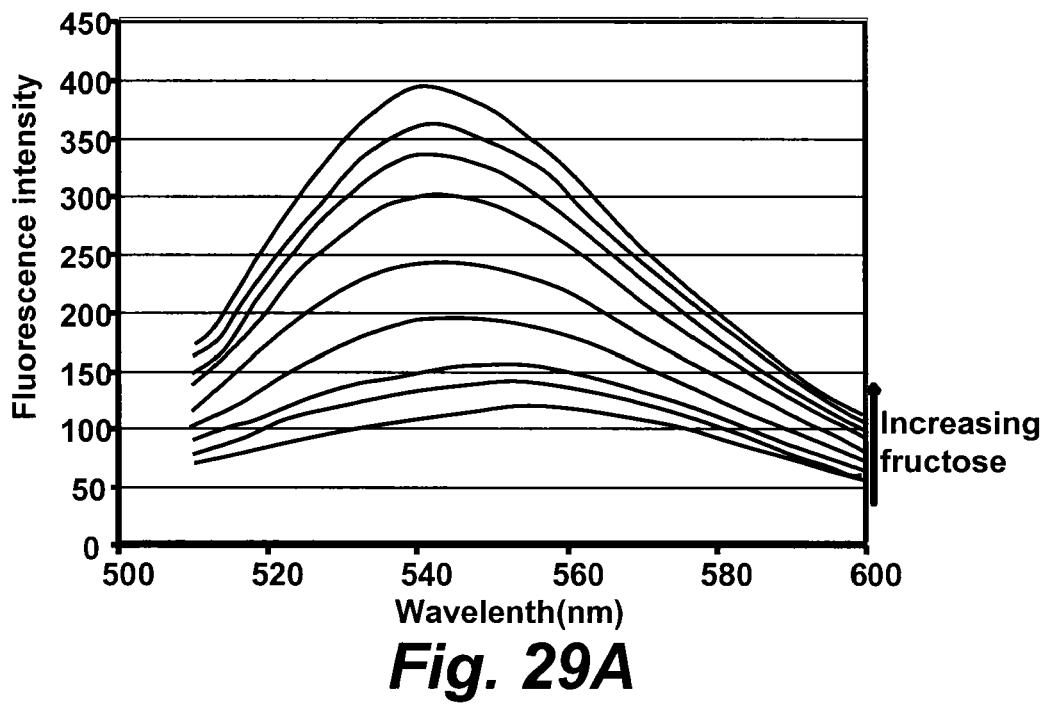
FIG. 29A is a graph showing the increase in the intensity of N-TTP fluorescence with increasing levels of fructose.
Figure 29B:
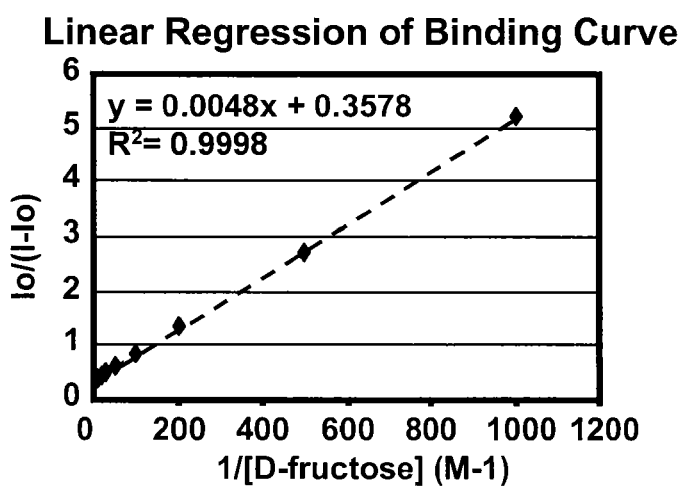
FIG. 29B is the linear regression curve for the binding of fructose to N-TTP.
Figure 30A:
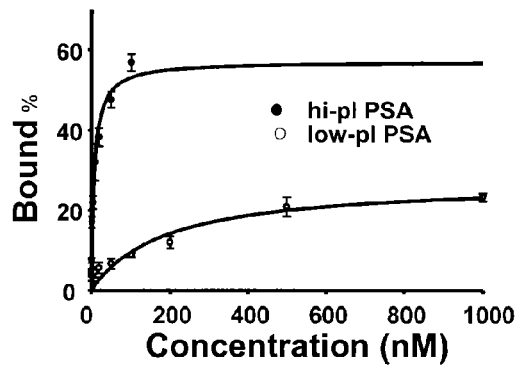
FIGS. 30A-30E are graphs showing the binding curves of the B-TTP aptamers 5A-5E (SEQ ID NOs.: 59-63) with hi-pI and low-pI PSA.
Figure 30B:
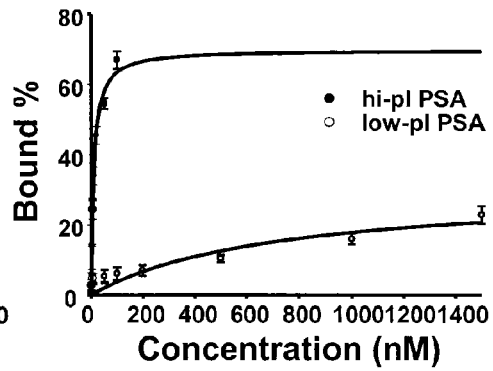
Figure 30C:
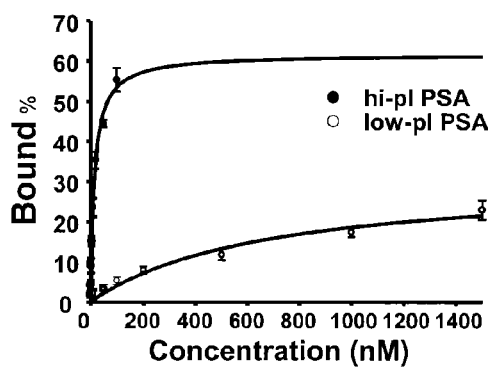
Figure 30D:
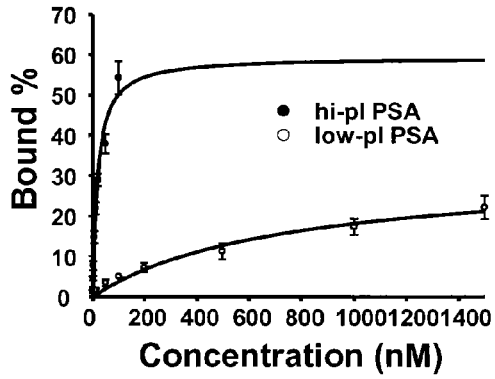
Figure 30E:
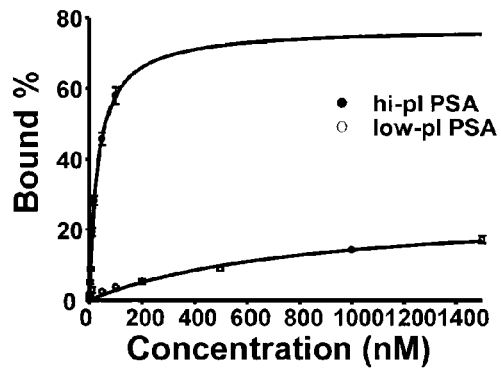

As shown in FIGS. 29A and 29B, the fluorescence intensity of N-TTP increased upon D-fructose addition in a concentration dependent fashion. The binding constants were determined using the following equation:

$$I_0/(I-I_0)=(\epsilon_B/\epsilon_{B-S}K_a)*1/[sugar]+\epsilon_B/\epsilon_{B-S}$$

where $I_0$ is fluorescence intensity of boronic acid solution; I: fluorescence intensity upon adding sugar, $\epsilon_B$: fluorescence correlation factor of boronic acid; $\epsilon_B$-s is the fluorescence correlation factor of boronic acid-sugar complex; $K_a$ is the binding constant; [sugar] is the sugar concentration.

By plotting (Io/(I-Io) vs. 1/[D-fructose], the intercept is $\epsilon_B/\epsilon_{B-S}$ and slope is ($\epsilon_B/\epsilon_{B-S}K_a$). Thus, the binding constant $K_a$ is intercept/slope, as shown in FIG. 29B. The binding constant (Ka) was determined to be 84±9 M$^{-1}$ from triplicate experiments.

We claim the following:

1. A nucleotide monomer having the formula:

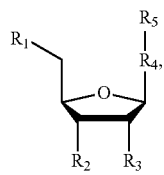

wherein $R_1$ is selected from the group consisting of: a monophosphate ester, a diphosphate ester, and a triphosphate ester;

wherein $R_2$ and $R_3$ are each individually selected from H, or OH;

wherein $R_4$ is a base selected from the group consisting of: adenine, cytosine, guanine, thymine, hypoxanthine and uracil; and wherein $R_5$ is a boronic acid other than an unsubstituted phenylboronic acid having the structure:

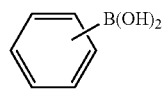

wherein $R_4$ and $R_5$ are linked by a a spacer, wherein said spacer is the product of a Click chemistry reaction between an azide group of a linker covalently attached to the boronic acid ($R_5$) and a reactive alkynyl group of a tether which has a second alkynyl group conjugated to the base ($R_4$).

2. The nucleotide monomer of claim 1, wherein the second alkynyl group is an ethynyl group.

3. The nucleotide monomer of claim 1, wherein the tether has the formula

—C≡C—CH$_2$—CH$_2$—CO—NH—CH$_2$—C≡C—.

4. The nucleotide monomer of claim 1, wherein $R_4$ is uracil, $R_2$ is OH, and $R_3$ is H.

5. The nucleotide monomer of claim 1, wherein $R_5$ is a boronic acid selected from the group consisting of: a substituted phenylboronic acid, a naphthalenylboronic acid, a quinolinylboronic acid, a pyridinylboronic acid, a furanylboronic acid, a thiophenylboronic acid, an indolylboronic acid a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

6. The nucleotide monomer of claim 5, wherein $R_5$ is selected from the group consisting of the structures:

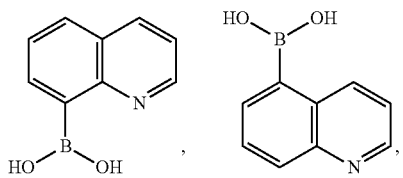

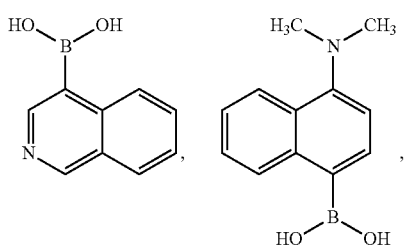

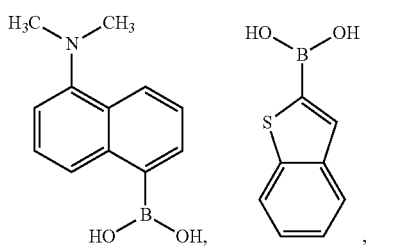

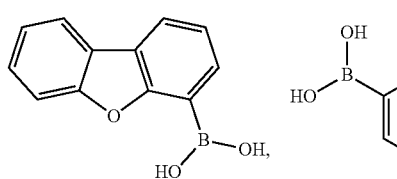

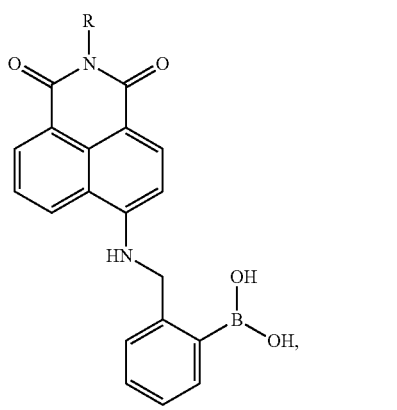

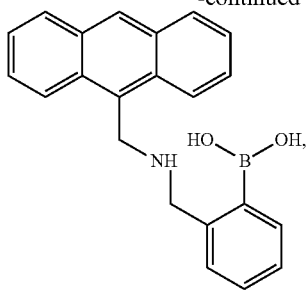
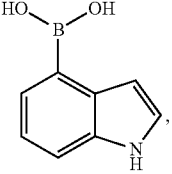
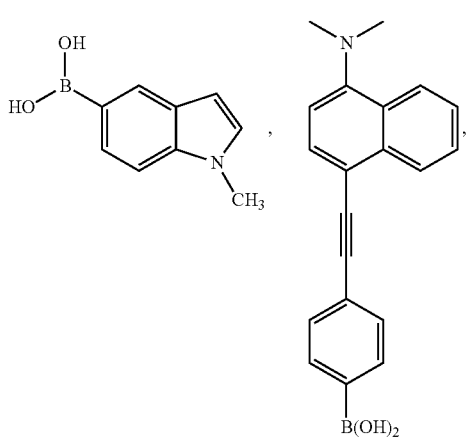
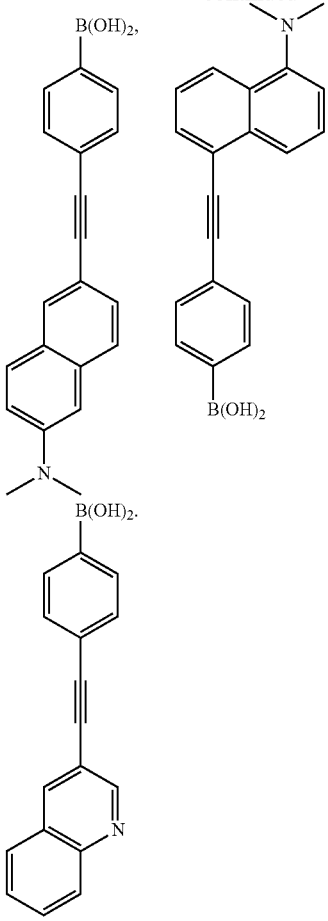
7. A nucleotide monomer having the formula:
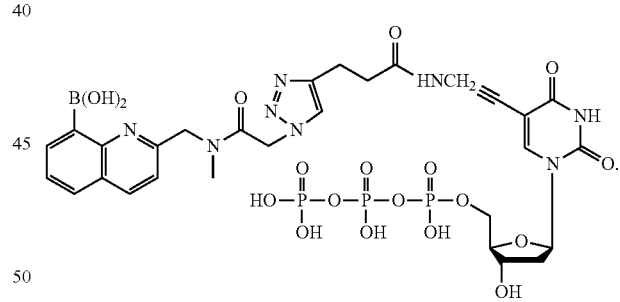
8. An oligonucleotide comprising at least one nucleotide monomer having the formula:
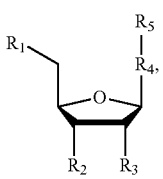
wherein $R_1$ is a monophosphate ester;
wherein $R_2$ and $R_3$ are each individually selected from H, or OH;

wherein R₄ is a base selected from the group consisting of: adenine, cytosine, guanine, thymine, inosine and uracil;

wherein R₅ is a boronic acid other than an unsubstituted phenylboronic acid having the structure:

wherein R₄ and R₅ are linked by a spacer, wherein said spacer is the product of a Click chemistry reaction between an azide group of a linker covalently attached to the boronic acid (R₅) and a reactive alkynyl group of a tether which has a second alkynyl group conjugated to the base (R₄).

9. The oligonucleotide of claim 8, wherein R₄ is uracil, R₂ is OH, and R₃ is H.

10. The oligonucleotide of claim 8, wherein R₅ is a boronic acid selected from the group consisting of: a substituted phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

11. The oligonucleotide of claim 8, wherein the boronic acid is a fluorescent boronic acid.

12. The oligonucleotide of claim 11, wherein the fluorescent boronic acid is selected from the group consisting of the structures:

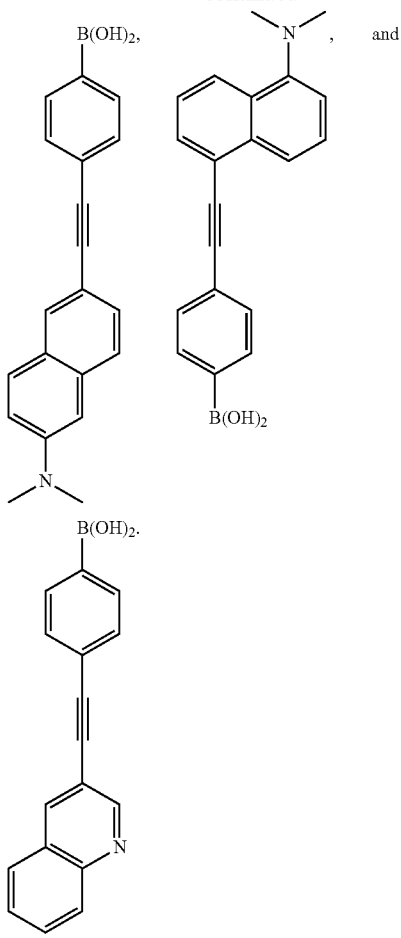

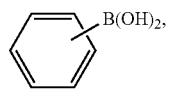

wherein $R_4$ and $R_5$ are linked by a spacer, wherein said spacer is the product of a Click chemistry reaction between an azide group of a linker covalently attached to the boronic acid ($R_5$) and a reactive alkynyl group of a tether which has a second alkynyl group conjugated to the base ($R_4$), and wherein the aptamer has selective affinity for a target polypeptide and a glycosylation chain thereon;

(b) amplifying the first subpopulation of aptamers without using boronic acid-modified TTP, and selecting from the amplification products thereof a second subpopulation of aptamers not binding to a glycosylated species of the target polypeptide or protein; and (c) amplifying the second subpopulation of aptamers using boronic acid-modified TTP, thereby providing a population of boronic acid-modified aptamers capable of selectively binding to a glycosylation site of a target polypeptide or protein.

14. The method of claim 13, further comprising a counter-selection step, wherein the counter-selection step comprises identifying aptamers capable of selectively binding to a solid support not having a target polypeptide bound thereto, a deglycosylated target polypeptide or protein, or a cross-reacting non-targeted polypeptide or proteins.

15. The method of claim 13, wherein step (a) comprises:
(a1) amplifying a library of randomized oligonucleotides, wherein each oligonucleotide includes at least one nucleotide having a boronic acid label linked to a base thereon;
(a2) contacting the library with a glycosylated target polypeptide or protein under conditions whereby a subpopulation of the library of aptamers selectively binds to a glycosylation site of the target polypeptide;
(a3) isolating target polypeptides or proteins having the subpopulation of aptamers bound thereto, and eluting the subpopulation of aptamers from the target polypeptide;
(a4) amplifying the eluted subpopulation of aptamers; and
(a5) repeating steps (a2)-(a4), thereby isolating a first subpopulation of aptamers from the amplified library from step (a1), wherein the aptamers are capable of binding a glycosylation site of the target polypeptide.

16. The method of claim 13, further comprising:
(i) inserting a population of aptamers isolated in step c into a vector, and isolating clones thereof;
(ii) identifying a plurality of aptamer clones, wherein each aptamer has a nucleotide sequence differing from the sequences of the other aptamers;
(iii) determining the dissociation constants of the individual selected aptamers and the target glycosylated polypeptide;
(iv) comparing the dissociation constants of the aptamer sequences to the dissociation constants of a control aptamer not having a boronic acid thereon; and
(v) selecting one or more aptamers having a lower dissociation constant than the control, whereby the selected aptamers have enhanced selective affinity for a glycosylated site of the target polypeptide compared to control aptamers having an identical nucleotide sequence to that of the selected aptamers but not having a boronic acid group thereon.

13. A method of isolating an aptamer having selective affinity for a target polypeptide and a glycan thereon, comprising:
(a) selecting a first subpopulation of aptamers binding to a target glycosylated polypeptide or protein from a population of randomized oligonucleotides, wherein each oligonucleotide of the population of randomized oligonucleotides includes at least one nucleotide having a boronic acid label linked to a base thereon, wherein said at least one nucleotide monomer has the formula:

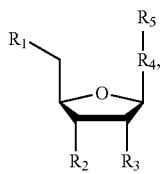

wherein $R_1$ is a monophosphate ester;

wherein $R_2$ and $R_3$ are each individually selected from H, or OH;

wherein $R_4$ is a base selected from the group consisting of: adenine, cytosine, guanine, thymine, inosine and uracil;

wherein $R_5$ is a boronic acid other than an unsubstituted phenylboronic acid having the structure:

17. The method of claim 13, wherein the target polypeptide is immobilized on a solid support.

18. The method of claim 13, wherein $R_4$ is uracil, $R_2$ is OH, and $R_3$ is H.

19. The method of claim 13, wherein $R_5$ is a boronic acid selected from the group consisting of: a substituted phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

20. The method of claim 13, wherein the at least one nucleotide having a boronic acid label modified base thereon comprises a fluorescent boronic acid selected from the group having the formulas:

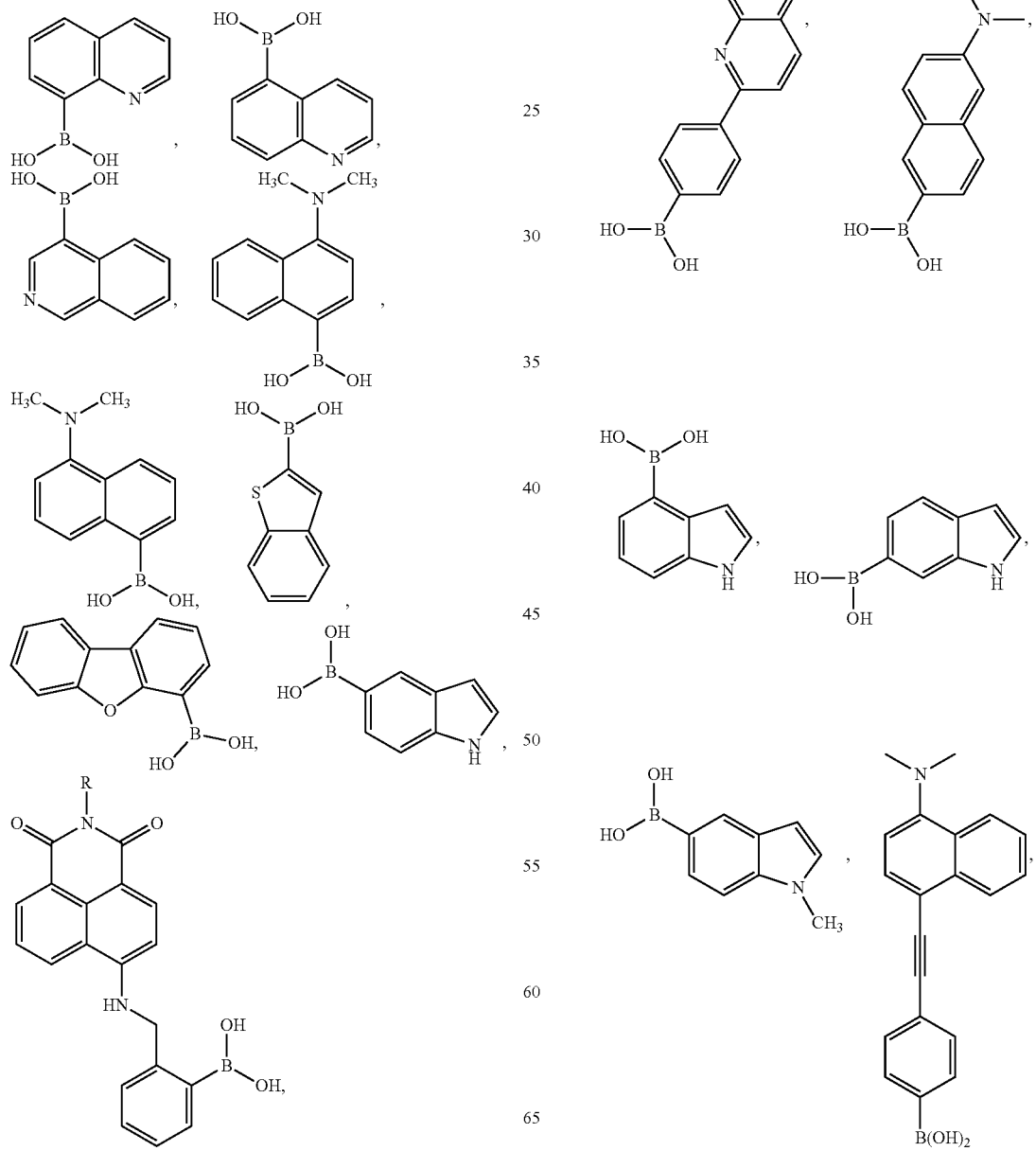

-continued

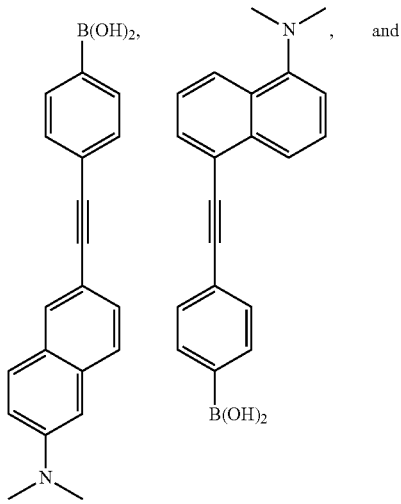

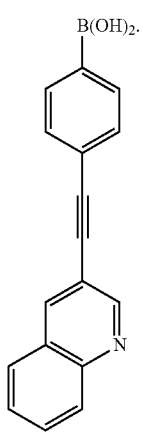

21. A method of detecting a glycosylated species of a target polypeptide, comprising:
(a) providing a target polypeptide;
(b) contacting the target polypeptide with a first aptamer comprising at least one nucleotide having a boronic acid label linked to a base thereon, wherein the at least one nucleotide monomer has the formula:

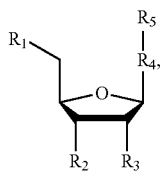

wherein $R_1$ is a monophosphate ester;
wherein $R_2$ and $R_3$ are each individually selected from H, or OH;
wherein $R_4$ is a base selected from the group consisting of: adenine, cytosine, guanine, thymine, inosine and uracil;
wherein $R_5$ is a boronic acid other than an unsubstituted phenylboronic acid having the structure:

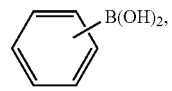

wherein $R_4$ and $R_5$ are linked by a spacer, wherein said spacer is the product of a Click chemistry reaction between an azide group of a linker covalently attached to the boronic acid ($R_5$) and a reactive alkynyl group of a tether which has a second alkynyl group conjugated to the base ($R_4$), wherein the first aptamer has enhanced selective affinity for a glycosylated site of the target polypeptide compared to a second aptamer having an identical nucleotide sequence to that of the first aptamer but not having a boronic acid group thereon;
(c) providing conditions suitable for selective binding of the first aptamer to the glycosylated site of the target polypeptide; and
(d) detecting a population of bound first aptamers, thereby indicating the presence of the glycosylation site of the target polypeptide.

22. The method of claim 21, wherein the glycosylation site of the target polypeptide comprises a region of a glycosylation chain and a region of the polypeptide.

23. The method of claim 21, wherein $R_4$ is uracil, $R_2$ is OH, and $R_3$ is H.

24. The method of claim 21, wherein $R_5$ is a boronic acid selected from the group consisting of: a substituted phenylboronic acid, a naphthalenylboronic acid, a quinolinylboronic acid, a pyridinylboronic acid, a furanylboronic acid, a thiophenylboronic acid, an indolylboronic acid, a 1,8-naphthalimide-based boronic acid, an α-acetaminoalkylboronic acid, a quinolin-4-ylboronic acid, a quinolin-5-ylboronic acid, a quinolin-8-ylboronic acid, a pyridinylboronic acid, a furan-2-ylboronic acid, and a thiophen-2-ylboronic acid.

25. The method of claim 21, wherein the boronic acid is a fluorescent boronic acid selected from the group consisting of the structures:

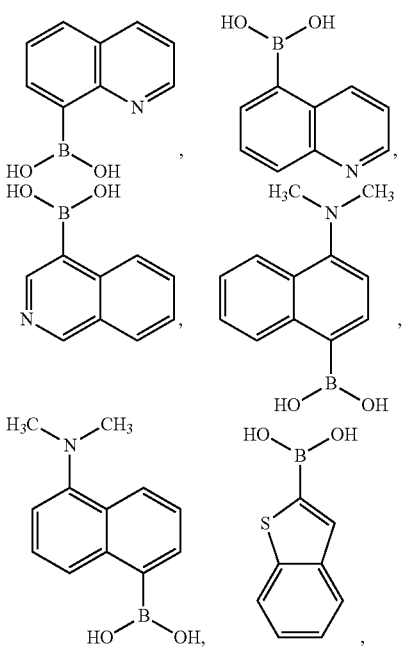

-continued

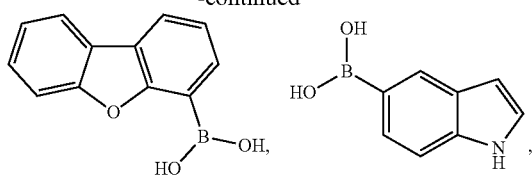
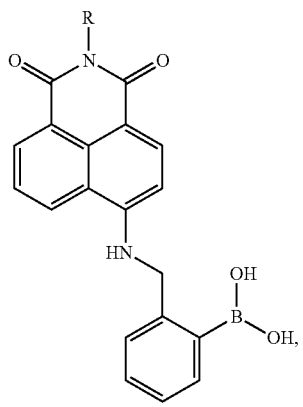
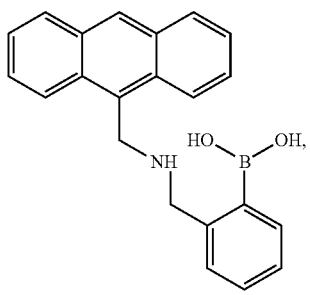
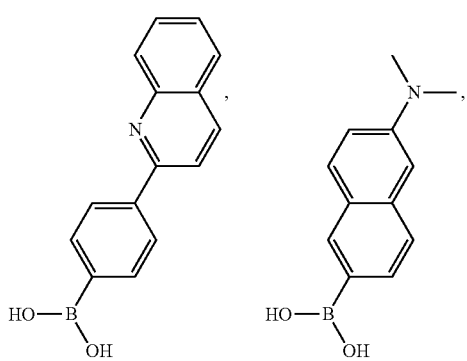
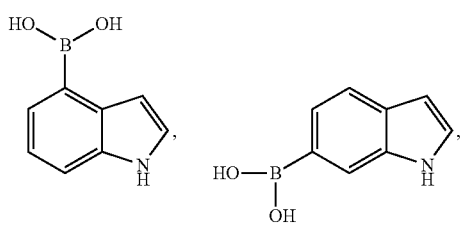

-continued

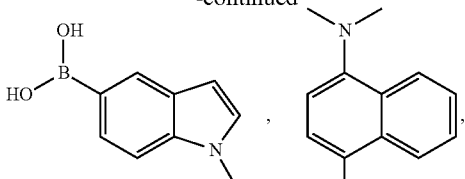
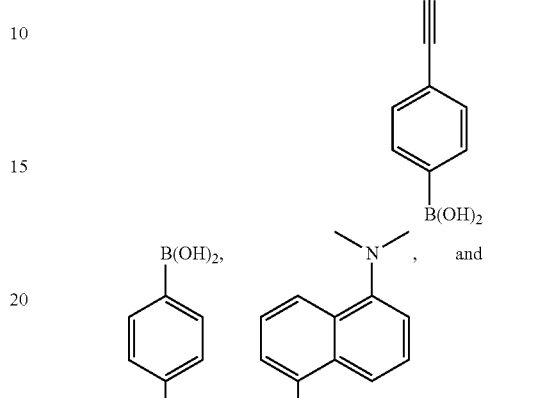
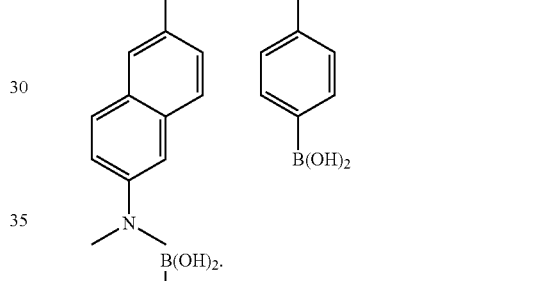
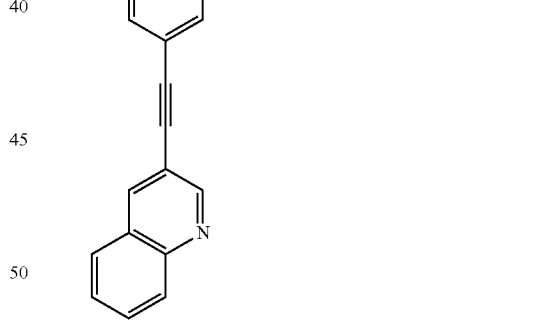

26. The method of claim 21, wherein the target polypeptide is selected from the group consisting of: an isolated polypeptide or a fragment thereof, a polypeptide in a cell or tissue of an animal or plant, or a cultured cell.

27. The method of claim 21, wherein the target polypeptide is Prostate Serum Antigen (PSA) or fibrinogen.

28. The method of claim 27, wherein the first aptamer selectively binds to high pI PSA, low pI PSA, or both high and low pI PSA.

29. The method of claim 27, wherein the aptamer selectively binds to a glycosylated species of fibrinogen.

* * * * *

SEQUENCE LISTING

<160> NUMBER OF SEQ ID NOS: 69

<210> SEQ ID NO 1
<211> LENGTH: 21
<212> TYPE: DNA
<213> ORGANISM: Artificial sequence
<220> FEATURE:
<223> OTHER INFORMATION: PCR Primer

<400> SEQUENCE: 1
gcgtaatacg actcactata g                                      21

<210> SEQ ID NO 2
<211> LENGTH: 20
<212> TYPE: DNA
<213> ORGANISM: Artificial sequence
<220> FEATURE:
<223> OTHER INFORMATION: PCR Primer

<400> SEQUENCE: 2
gcgtaatacg actcactata                                        20

```
<210> SEQ ID NO 3
<211> LENGTH: 20
<212> TYPE: DNA
<213> ORGANISM: Artificial sequence
<220> FEATURE:
<223> OTHER INFORMATION: PCR Primer

<400> SEQUENCE: 3
tgtacgtttc ggcctttcgg                                                  20

<210> SEQ ID NO 4
<211> LENGTH: 55
<212> TYPE: DNA
<213> ORGANISM: Artificial sequence
<220> FEATURE:
<223> OTHER INFORMATION: PCR Template

<400> SEQUENCE: 4
tgtacgtttc ggcctttcgg cctcatcagg ttgcctatag tgagtcgtat tacgc          55

<210> SEQ ID NO 5
<211> LENGTH: 16
<212> TYPE: DNA
<213> ORGANISM: Artificial sequence
<220> FEATURE:
<223> OTHER INFORMATION: PCR Primer

<400> SEQUENCE: 5
cgccgccccc gccgcg                                                      16

<210> SEQ ID NO 6
<211> LENGTH: 16
<212> TYPE: DNA
<213> ORGANISM: Artificial sequence
<220> FEATURE:
<223> OTHER INFORMATION: PCR Primer

<400> SEQUENCE: 6
cggcggcccg cgggcg                                                      16

<210> SEQ ID NO 7
<211> LENGTH: 72
<212> TYPE: DNA
<213> ORGANISM: Artificial sequence
<220> FEATURE:
<223> OTHER INFORMATION: Aptamer
<220> FEATURE:
<221> NAME/KEY: misc_feature
<222> LOCATION: (17)..(56)
<223> OTHER INFORMATION: n is a, c, g, or t

<400> SEQUENCE: 7
cgccgccccc gccgcgnnnn nnnnnnnnnn nnnnnnnnnn nnnnnnnnnn nnnnncgcc      60 cgcgggccgc cg                                                          72

<210> SEQ ID NO 8
<211> LENGTH: 21
<212> TYPE: DNA
<213> ORGANISM: Artificial sequence
<220> FEATURE:
<223> OTHER INFORMATION: PCR Template

<400> SEQUENCE: 8
ggttccacca gcaacccgct a                                                21
```

```
<210> SEQ ID NO 9
<211> LENGTH: 14
<212> TYPE: DNA
<213> ORGANISM: Artificial sequence
<220> FEATURE:
<223> OTHER INFORMATION: PCR Primer

<400> SEQUENCE: 9
tagcgggttg ctgg                                                        14

<210> SEQ ID NO 10
<211> LENGTH: 90
<212> TYPE: DNA
<213> ORGANISM: Artificial sequence
<220> FEATURE:
<223> OTHER INFORMATION: PCR Template
<220> FEATURE:
<221> NAME/KEY: misc_feature
<222> LOCATION: (21)..(70)
<223> OTHER INFORMATION: n is a, c, g, or t

<400> SEQUENCE: 10
ccttcgttgt ctgccttcgt nnnnnnnnnn nnnnnnnnnn nnnnnnnnnn nnnnnnnnnn      60
nnnnnnnnnn acccttcaga attcgcacca                                       90

<210> SEQ ID NO 11
<211> LENGTH: 20
<212> TYPE: DNA
<213> ORGANISM: Artificial sequence
<220> FEATURE:
<223> OTHER INFORMATION: PCR Primer

<400> SEQUENCE: 11
ccttcgttgt ctgccttcgt                                                  20

<210> SEQ ID NO 12
<211> LENGTH: 20
<212> TYPE: DNA
<213> ORGANISM: Artificial sequence
<220> FEATURE:
<223> OTHER INFORMATION: PCR Primer

<400> SEQUENCE: 12
tggtgcgaat tctgaagggt                                                  20

<210> SEQ ID NO 13
<211> LENGTH: 90
<212> TYPE: DNA
<213> ORGANISM: Artificial sequence
<220> FEATURE:
<223> OTHER INFORMATION: Aptamer

<400> SEQUENCE: 13
ccttcgttgt ctgccttcgt agcggatcga attacgcgtt aacggcaacc gataacggga      60
ccgattgcac acccttcaga attcgcacca                                       90

<210> SEQ ID NO 14
<211> LENGTH: 90
<212> TYPE: DNA
<213> ORGANISM: Artificial sequence
<220> FEATURE:
<223> OTHER INFORMATION: Aptamer
```

-continued

```
<400> SEQUENCE: 14
ccttcgttgt ctgccttcgt aggaccgcag acatcgacgc agggaaattc cgcaagtcca      60
gccaaatgcc acccttcaga attcgcacca                                      90

<210> SEQ ID NO 15
<211> LENGTH: 90
<212> TYPE: DNA
<213> ORGANISM: Artificial sequence
<220> FEATURE:
<223> OTHER INFORMATION: Aptamer

<400> SEQUENCE: 15
ccttcgttgt ctgccttcgt agtcgactct gacgcatgga cgtatcctgt gcgtatgcat      60
tatgaagcac acccttcaga attcgcacca                                      90

<210> SEQ ID NO 16
<211> LENGTH: 90
<212> TYPE: DNA
<213> ORGANISM: Artificial sequence
<220> FEATURE:
<223> OTHER INFORMATION: Aptamer

<400> SEQUENCE: 16
ccttcgttgt ctgccttcgt gagcggagtc agacgcacgc tcgtacctgt gcgcaagcac      60
tatgacggac acccttcaga attcgcacca                                      90

<210> SEQ ID NO 17
<211> LENGTH: 90
<212> TYPE: DNA
<213> ORGANISM: Artificial sequence
<220> FEATURE:
<223> OTHER INFORMATION: Aptamer

<400> SEQUENCE: 17
ccttcgttgt ctgccttcgt agccttaagc tccctatgat tggccggatc gtaagtacgt      60
tgggatcgag acccttcaga attcgcacca                                      90

<210> SEQ ID NO 18
<211> LENGTH: 90
<212> TYPE: DNA
<213> ORGANISM: Artificial sequence
<220> FEATURE:
<223> OTHER INFORMATION: Aptamer

<400> SEQUENCE: 18
ccttcgttgt ctgccttcgt accggttccg atatgaagca aagtccacag gccaataagc      60
aggagcgcag acccttcaga attcgcacca                                      90

<210> SEQ ID NO 19
<211> LENGTH: 90
<212> TYPE: DNA
<213> ORGANISM: Artificial sequence
<220> FEATURE:
<223> OTHER INFORMATION: Aptamer

<400> SEQUENCE: 19
ccttcgttgt ctgccttcgt accatggctg tcaacggccg tccggtaccg ggcttgacga      60
gtatccggac acccttcaga attcgcacca                                      90
```

```
<210> SEQ ID NO 20
<211> LENGTH: 90
<212> TYPE: DNA
<213> ORGANISM: Artificial sequence
<220> FEATURE:
<223> OTHER INFORMATION: Aptamer

<400> SEQUENCE: 20
ccttcgttgt ctgccttcgt ataggtctgt gctgcgctat cgtgcgcacc tcttcagata      60
tgtcgcacgc acccttcaga attcgcacca                                       90

<210> SEQ ID NO 21
<211> LENGTH: 90
<212> TYPE: DNA
<213> ORGANISM: Artificial sequence
<220> FEATURE:
<223> OTHER INFORMATION: Aptamer

<400> SEQUENCE: 21
ccttcgttgt ctgccttcgt acggccggct ggtagccacg ccgggcttgc ttgaggtcag      60
cctatggcgc acccttcaga attcgcacca                                       90

<210> SEQ ID NO 22
<211> LENGTH: 90
<212> TYPE: DNA
<213> ORGANISM: Artificial sequence
<220> FEATURE:
<223> OTHER INFORMATION: Aptamer

<400> SEQUENCE: 22
ccttcgttgt ctgccttcgt gcgcgcatag accgagtggc atgacgccta tctcgtgata      60
gaggactccg acccttcaga attcgcacca                                       90

<210> SEQ ID NO 23
<211> LENGTH: 90
<212> TYPE: DNA
<213> ORGANISM: Artificial sequence
<220> FEATURE:
<223> OTHER INFORMATION: Aptamer

<400> SEQUENCE: 23
ccttcgttgt ctgccttcgt atatctggac aagggaattc gcaagcgcga agtgaacgca      60
ggtagctcgc acccttcaga attcgcacca                                       90

<210> SEQ ID NO 24
<211> LENGTH: 90
<212> TYPE: DNA
<213> ORGANISM: Artificial sequence
<220> FEATURE:
<223> OTHER INFORMATION: Aptamer

<400> SEQUENCE: 24
ccttcgttgt ctgccttcgt agcagtatgg tccgaaagat cggcgctaag gctcgtacta      60
ggcgtatgcc acccttcaga attcgcacca                                       90

<210> SEQ ID NO 25
<211> LENGTH: 90
<212> TYPE: DNA
<213> ORGANISM: Artificial sequence
<220> FEATURE:
<223> OTHER INFORMATION: Aptamer
```

<400> SEQUENCE: 25
ccttcgttgt ctgccttcgt ccgtgtcccg ctatgatgct acttgcattc gcggaattga    60
accgtcgcgc acccttcaga attcgcacca    90

<210> SEQ ID NO 26
<211> LENGTH: 90
<212> TYPE: DNA
<213> ORGANISM: Artificial sequence
<220> FEATURE:
<223> OTHER INFORMATION: Aptamer

<400> SEQUENCE: 26
ccttcgttgt ctgccttcgt agcccttgca cctatgaggt atgatcttcg ttggacgcag    60
ttactacgcc acccttcaga attcgcacca    90

<210> SEQ ID NO 27
<211> LENGTH: 90
<212> TYPE: DNA
<213> ORGANISM: Artificial sequence
<220> FEATURE:
<223> OTHER INFORMATION: Aptamer

<400> SEQUENCE: 27
ccttcgttgt ctgccttcgt tggacaacgt cggactcgat agcgtagacg gaagcctggt    60
ctggtcgcgc acccttcaga attcgcacca    90

<210> SEQ ID NO 28
<211> LENGTH: 90
<212> TYPE: DNA
<213> ORGANISM: Artificial sequence
<220> FEATURE:
<223> OTHER INFORMATION: Aptamer

<400> SEQUENCE: 28
ccttcgttgt ctgccttcgt cagctactgg gctatctgga cttggcaatc tcgcttgcag    60
cattgagcgc acccttcaga attcgcacca    90

<210> SEQ ID NO 29
<211> LENGTH: 90
<212> TYPE: DNA
<213> ORGANISM: Artificial sequence
<220> FEATURE:
<223> OTHER INFORMATION: Aptamer

<400> SEQUENCE: 29
ccttcgttgt ctgccttcgt agtcgactct gacgcatgga cgtatcctgt gcgtatgcat    60
tatgaagcac acccttcaga attcgcacca    90

<210> SEQ ID NO 30
<211> LENGTH: 90
<212> TYPE: DNA
<213> ORGANISM: Artificial sequence
<220> FEATURE:
<223> OTHER INFORMATION: Aptamer

<400> SEQUENCE: 30
ccttcgttgt ctgccttcgt agcggatcga attacgcgtt aacggcaacc gataacggga    60
ccgattgcac acccttcaga attcgcacca    90

```
<210> SEQ ID NO 31
<211> LENGTH: 90
<212> TYPE: DNA
<213> ORGANISM: Artificial sequence
<220> FEATURE:
<223> OTHER INFORMATION: Aptamer

<400> SEQUENCE: 31
ccttcgttgt ctgccttcgt acgaacgctg acatcgacgg tcggcaattc cgcaagtcca      60
gcctaatgac acccttcaga attcgcacca                                      90

<210> SEQ ID NO 32
<211> LENGTH: 90
<212> TYPE: DNA
<213> ORGANISM: Artificial sequence
<220> FEATURE:
<223> OTHER INFORMATION: Aptamer

<400> SEQUENCE: 32
ccttcgttgt ctgccttcgt agcgctagga cgtaagatgc atgccctaga ttcgaagctg      60
atgccatgag acccttcaga attcgcacca                                      90

<210> SEQ ID NO 33
<211> LENGTH: 90
<212> TYPE: DNA
<213> ORGANISM: Artificial sequence
<220> FEATURE:
<223> OTHER INFORMATION: Aptamer

<400> SEQUENCE: 33
ccttcgttgt ctgccttcgt acggctaacg gaatcaagct tagaggataa gccgataagc      60
acgatagcac acccttcaga attcgcacca                                      90

<210> SEQ ID NO 34
<211> LENGTH: 90
<212> TYPE: DNA
<213> ORGANISM: Artificial sequence
<220> FEATURE:
<223> OTHER INFORMATION: Aptamer

<400> SEQUENCE: 34
ccttcgttgt ctgccttcgt tgcaataagg tcggattgat tggcccgaac gttagaaccc      60
ggggaacgac acccttcaga attcgcacca                                      90

<210> SEQ ID NO 35
<211> LENGTH: 90
<212> TYPE: DNA
<213> ORGANISM: Artificial sequence
<220> FEATURE:
<223> OTHER INFORMATION: Aptamer

<400> SEQUENCE: 35
ccttcgttgt ctgccttcgt agcgctaaga gggtgcggat tgaggcggat cgcgggcttg      60
accgattgcc acccttcaga attcgcacca                                      90

<210> SEQ ID NO 36
<211> LENGTH: 90
<212> TYPE: DNA
<213> ORGANISM: Artificial sequence
<220> FEATURE:
<223> OTHER INFORMATION: Aptamer
```

<400> SEQUENCE: 36
ccttcgttgt ctgccttcgt agcggcggga gggagttagg cgaggcgagc ccgagcttag    60
gcttaggccg acccttcaga attcgcacca    90

<210> SEQ ID NO 37
<211> LENGTH: 90
<212> TYPE: DNA
<213> ORGANISM: Artificial sequence
<220> FEATURE:
<223> OTHER INFORMATION: Aptamer

<400> SEQUENCE: 37
ccttcgttgt ctgccttcgt aggaccgcag acatcgacgc agggaaattc cgcaagtcca    60
gccaaatgcc acccttcaga attcgcacca    90

<210> SEQ ID NO 38
<211> LENGTH: 90
<212> TYPE: DNA
<213> ORGANISM: Artificial sequence
<220> FEATURE:
<223> OTHER INFORMATION: Aptamer

<400> SEQUENCE: 38
ccttcgttgt ctgccttcgt agcctgctct ggcgcatgta cgcatcgcgt tcgtatgcaa    60
tatgacgcat acccttcaga attcgcacca    90

<210> SEQ ID NO 39
<211> LENGTH: 90
<212> TYPE: DNA
<213> ORGANISM: Artificial sequence
<220> FEATURE:
<223> OTHER INFORMATION: Aptamer

<400> SEQUENCE: 39
ccttcgttgt ctgccttcgt acagggtagc gctacgctag actaggtacg tatcctgata    60
tgacgctcgc acccttcaga attcgcacca    90

<210> SEQ ID NO 40
<211> LENGTH: 90
<212> TYPE: DNA
<213> ORGANISM: Artificial sequence
<220> FEATURE:
<223> OTHER INFORMATION: Aptamer

<400> SEQUENCE: 40
ccttcgttgt ctgccttcgt acggcggctg gagcaacgcc tggcatgggt gcggtcagaa    60
gtattgcgca acccttcaga attcgcacca    90

<210> SEQ ID NO 41
<211> LENGTH: 90
<212> TYPE: DNA
<213> ORGANISM: Artificial sequence
<220> FEATURE:
<223> OTHER INFORMATION: Aptamer

<400> SEQUENCE: 41
ccttcgttgt ctgccttcgt aaccggcgtg agcgagtcag tcgaggcgag ctacgagctt    60
agctcaggtc acccttcaga attcgcacca    90

<210> SEQ ID NO 42
<211> LENGTH: 90
<212> TYPE: DNA
<213> ORGANISM: Artificial sequence
<220> FEATURE:
<223> OTHER INFORMATION: Aptamer

<400> SEQUENCE: 42
ccttcgttgt ctgccttcgt aacgtctaac ggtatcaagc ttagaggata cgctgatcac    60
taccatagta acccttcaga attcgcacca                                    90

<210> SEQ ID NO 43
<211> LENGTH: 90
<212> TYPE: DNA
<213> ORGANISM: Artificial sequence
<220> FEATURE:
<223> OTHER INFORMATION: Aptamer

<400> SEQUENCE: 43
ccttcgttgt ctgccttcgt aacggcgggc ttgatagtct cgcaggccat actcgagctc    60
tcgtatgacg acccttcaga attcgcacca                                    90

<210> SEQ ID NO 44
<211> LENGTH: 90
<212> TYPE: DNA
<213> ORGANISM: Artificial sequence
<220> FEATURE:
<223> OTHER INFORMATION: Aptamer

<400> SEQUENCE: 44
ccttcgttgt ctgccttcgt agtgctacga ctatgacgca tatcgctcga ttcgtggcag    60
gttctcatac acccttcaga attcgcacca                                    90

<210> SEQ ID NO 45
<211> LENGTH: 90
<212> TYPE: DNA
<213> ORGANISM: Artificial sequence
<220> FEATURE:
<223> OTHER INFORMATION: Aptamer

<400> SEQUENCE: 45
ccttcgttgt ctgccttcgt acgcgcgcat agtccgagta gtatgacgca tatgtgctac    60
tgagtcctac acccttcaga attcgcacca                                    90

<210> SEQ ID NO 46
<211> LENGTH: 90
<212> TYPE: DNA
<213> ORGANISM: Artificial sequence
<220> FEATURE:
<223> OTHER INFORMATION: Aptamer

<400> SEQUENCE: 46
ccttcgttgt ctgccttcgt acagatagcg agagctacga tgctgcgaat agagcgtacg    60
gcgggcttga acccttcaga attcgcacca                                    90

<210> SEQ ID NO 47
<211> LENGTH: 90
<212> TYPE: DNA
<213> ORGANISM: Artificial sequence
<220> FEATURE:
<223> OTHER INFORMATION: Aptamer

```
<400> SEQUENCE: 47
ccttcgttgt ctgccttcgt acagcagtat cgtgcgaaag atcgtcgcta tgagtcctac      60
agtcttacgc acccttcaga attcgcacca                                      90

<210> SEQ ID NO 48
<211> LENGTH: 90
<212> TYPE: DNA
<213> ORGANISM: Artificial sequence
<220> FEATURE:
<223> OTHER INFORMATION: Aptamer

<400> SEQUENCE: 48
ccttcgttgt ctgccttcgt agccgttgca cggtatgagg catagaccta cgtatgaggc      60
taacttcggc acccttcaga attcgcacca                                      90

<210> SEQ ID NO 49
<211> LENGTH: 90
<212> TYPE: DNA
<213> ORGANISM: Artificial sequence
<220> FEATURE:
<223> OTHER INFORMATION: Aptamer

<400> SEQUENCE: 49
ccttcgttgt ctgccttcgt gctatgtctg agcagtgcgt atggtacctc gtatcagcca      60
tatgacgcaa acccttcaga attcgcacca                                      90

<210> SEQ ID NO 50
<211> LENGTH: 90
<212> TYPE: DNA
<213> ORGANISM: Artificial sequence
<220> FEATURE:
<223> OTHER INFORMATION: Aptamer

<400> SEQUENCE: 50
ccttcgttgt ctgccttcgt acagctctat gagtacgcat cgagatcaga accgcgggct     60
tgaacgtcag acccttcaga attcgcacca                                      90

<210> SEQ ID NO 51
<211> LENGTH: 90
<212> TYPE: DNA
<213> ORGANISM: Artificial sequence
<220> FEATURE:
<223> OTHER INFORMATION: Aptamer

<400> SEQUENCE: 51
ccttcgttgt ctgccttcgt tatgacgcaa ctgtgcacaa tgcgactcag gacgtgtacg     60
agcgagtgta acccttcaga attcgcacca                                      90

<210> SEQ ID NO 52
<211> LENGTH: 90
<212> TYPE: DNA
<213> ORGANISM: Artificial sequence
<220> FEATURE:
<223> OTHER INFORMATION: Aptamer

<400> SEQUENCE: 52
ccttcgttgt ctgccttcgt cgtgaccagg acatatgagg catagcgctt gactctaccg     60
ctgctagcac acccttcaga attcgcacca                                      90
```

```
<210> SEQ ID NO 53
<211> LENGTH: 90
<212> TYPE: DNA
<213> ORGANISM: Artificial sequence
<220> FEATURE:
<223> OTHER INFORMATION: Aptamer

<400> SEQUENCE: 53
ccttcgttgt ctgccttcgt tagactatca cggatggacg tatcctgtgc gtatgacgca    60
tgaagcacta acccttcaga attcgcacca                                    90

<210> SEQ ID NO 54
<211> LENGTH: 90
<212> TYPE: DNA
<213> ORGANISM: Artificial sequence
<220> FEATURE:
<223> OTHER INFORMATION: Aptamer

<400> SEQUENCE: 54
ccttcgttgt ctgccttcgt atatgacgca tgcctagacc tccctatgat agcctggatc    60
gtacgtacgt acccttcaga attcgcacca                                    90

<210> SEQ ID NO 55
<211> LENGTH: 90
<212> TYPE: DNA
<213> ORGANISM: Artificial sequence
<220> FEATURE:
<223> OTHER INFORMATION: Aptamer

<400> SEQUENCE: 55
ccttcgttgt ctgccttcgt aggaccgcag acatcgacgc agggaaattc cgcaagtcca    60
gccaaatgcc acccttcaga attcgcacca                                    90

<210> SEQ ID NO 56
<211> LENGTH: 90
<212> TYPE: DNA
<213> ORGANISM: Artificial sequence
<220> FEATURE:
<223> OTHER INFORMATION: Aptamer

<400> SEQUENCE: 56
ccttcgttgt ctgccttcgt gagcagcgta gctctaagcc agactagtaa cgtatcctga    60
tatgacgcat acccttcaga attcgcacca                                    90

<210> SEQ ID NO 57
<211> LENGTH: 90
<212> TYPE: DNA
<213> ORGANISM: Artificial sequence
<220> FEATURE:
<223> OTHER INFORMATION: Aptamer

<400> SEQUENCE: 57
ccttcgttgt ctgccttcgt tcaggctgct atatgacgca tatcgacaga cgagtcagta    60
gctgcacaca acccttcaga attcgcacca                                    90

<210> SEQ ID NO 58
<211> LENGTH: 90
<212> TYPE: DNA
<213> ORGANISM: Artificial sequence
<220> FEATURE:
<223> OTHER INFORMATION: Aptamer
```

<400> SEQUENCE: 58
ccttcgttgt ctgccttcgg catcactacg gtcgagatac atagtcgcta tgacgcatca    60
gtcttacgct acccttcaga attcgcacca                                      90

<210> SEQ ID NO 59
<211> LENGTH: 90
<212> TYPE: DNA
<213> ORGANISM: Artificial sequence
<220> FEATURE:
<223> OTHER INFORMATION: Aptamer

<400> SEQUENCE: 59
ccttcgttgt ctgccttcgt tatcggtttg ccatcgacgg tcggcacttc cgctaccatc    60
tggcctaatg acccttcaga attcgcacca                                      90

<210> SEQ ID NO 60
<211> LENGTH: 90
<212> TYPE: DNA
<213> ORGANISM: Artificial sequence
<220> FEATURE:
<223> OTHER INFORMATION: Aptamer

<400> SEQUENCE: 60
ccttcgttgt ctgccttcgt ctaggcatat cggtttgcca tcgtcgagca cttccgctac    60
gtaagattcc acccttcaga attcgcacca                                      90

<210> SEQ ID NO 61
<211> LENGTH: 90
<212> TYPE: DNA
<213> ORGANISM: Artificial sequence
<220> FEATURE:
<223> OTHER INFORMATION: Aptamer

<400> SEQUENCE: 61
ccttcgttgt ctgccttcgt ttctacggta accttatcgg tttgccatcg acggccgtaa    60
ttcggcatcg acccttcaga attcgcacca                                      90

<210> SEQ ID NO 62
<211> LENGTH: 90
<212> TYPE: DNA
<213> ORGANISM: Artificial sequence
<220> FEATURE:
<223> OTHER INFORMATION: Aptamer

<400> SEQUENCE: 62
ccttcgttgt ctgccttcgt actctagcct acgtaatcac gattacggat atcggtttgc    60
catcgtcatg acccttcaga attcgcacca                                      90

<210> SEQ ID NO 63
<211> LENGTH: 90
<212> TYPE: DNA
<213> ORGANISM: Artificial sequence
<220> FEATURE:
<223> OTHER INFORMATION: Aptamer

<400> SEQUENCE: 63
ccttcgttgt ctgccttcgt atattcggcg tagccattag cttagcgatt agcctatcgg    60
tttgccatcg acccttcaga attcgcacca                                      90

```
<210> SEQ ID NO 64
<211> LENGTH: 90
<212> TYPE: DNA
<213> ORGANISM: Artificial sequence
<220> FEATURE:
<223> OTHER INFORMATION: Aptamer

<400> SEQUENCE: 64
ccttcgttgt ctgccttcgt tccgtggccg attacgggtc tatcggtttg ccatcgtacg    60
atgcggatca acccttcaga attcgcacca                                     90

<210> SEQ ID NO 65
<211> LENGTH: 90
<212> TYPE: DNA
<213> ORGANISM: Artificial sequence
<220> FEATURE:
<223> OTHER INFORMATION: Aptamer

<400> SEQUENCE: 65
ccttcgttgt ctgccttcgt cggcatgatc gtacgctatc ggtttgccat cgtaccgcta    60
gttcggtagc acccttcaga attcgcacca                                     90

<210> SEQ ID NO 66
<211> LENGTH: 90
<212> TYPE: DNA
<213> ORGANISM: Artificial sequence
<220> FEATURE:
<223> OTHER INFORMATION: Aptamer

<400> SEQUENCE: 66
ccttcgttgt ctgccttcgt taacctggcg atgcgaccgt gatgccgtat cggtttgcca    60
tcgatacgcc acccttcaga attcgcacca                                     90

<210> SEQ ID NO 67
<211> LENGTH: 90
<212> TYPE: DNA
<213> ORGANISM: Artificial sequence
<220> FEATURE:
<223> OTHER INFORMATION: Aptamer

<400> SEQUENCE: 67
ccttcgttgt ctgccttcgt taaacttcta aacctgccgg atactctata tcggtttgcc    60
atcgattaac acccttcaga attcgcacca                                     90

<210> SEQ ID NO 68
<211> LENGTH: 90
<212> TYPE: DNA
<213> ORGANISM: Artificial sequence
<220> FEATURE:
<223> OTHER INFORMATION: Aptamer

<400> SEQUENCE: 68
ccttcgttgt ctgccttcgt tatcgattag cggacgatta ggccatgagc gatatcggtt    60
tgccatcgcg acccttcaga attcgcacca                                     90

<210> SEQ ID NO 69
<211> LENGTH: 16
<212> TYPE: DNA
<213> ORGANISM: Artificial sequence
<220> FEATURE:
<223> OTHER INFORMATION: Aptamer
```

```
<400> SEQUENCE: 69
tatcggtttg ccatcg                                                   16
```